(12) United States Patent
Urano et al.

(10) Patent No.: US 9,891,231 B2
(45) Date of Patent: Feb. 13, 2018

(54) SOLUBLE MANF IN PANCREATIC β-CELL DISORDERS

(71) Applicant: University of Massachusetts, Boston, MA (US)

(72) Inventors: Fumihiko Urano, Saint Louis, MO (US); Kohsuke Kanekura, Brentwood, MO (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/374,190

(22) PCT Filed: Jan. 23, 2013

(86) PCT No.: PCT/US2013/022768
§ 371 (c)(1),
(2) Date: Jul. 23, 2014

(87) PCT Pub. No.: WO2013/112602
PCT Pub. Date: Aug. 1, 2013

(65) Prior Publication Data
US 2015/0198613 A1 Jul. 16, 2015

Related U.S. Application Data

(60) Provisional application No. 61/590,021, filed on Jan. 24, 2012.

(51) Int. Cl.
*A61K 38/00* (2006.01)
*G01N 33/68* (2006.01)
*A61K 38/18* (2006.01)
*A61K 38/28* (2006.01)
*A61K 45/06* (2006.01)
*A61K 31/473* (2006.01)
*A61K 38/17* (2006.01)
*C07K 14/47* (2006.01)
*G01N 33/50* (2006.01)
*C12N 15/113* (2010.01)

(52) U.S. Cl.
CPC ....... *G01N 33/6872* (2013.01); *A61K 31/473* (2013.01); *A61K 38/1709* (2013.01); *A61K 38/185* (2013.01); *A61K 38/28* (2013.01); *A61K 45/06* (2013.01); *C07K 14/47* (2013.01); *C12N 15/1136* (2013.01); *G01N 33/507* (2013.01); *G01N 33/5038* (2013.01); *G01N 33/6893* (2013.01); *C12N 2310/14* (2013.01); *G01N 2333/475* (2013.01); *G01N 2500/10* (2013.01); *G01N 2800/04* (2013.01); *G01N 2800/042* (2013.01); *G01N 2800/50* (2013.01)

(58) Field of Classification Search
CPC .......................... A61K 38/1709; A61K 38/00
See application file for complete search history.

(56) References Cited

U.S. PATENT DOCUMENTS

| 5,574,010 A | * | 11/1996 | McFadden | A61K 38/22 514/19.3 |
| 2001/0056116 A1 | * | 12/2001 | Shashoua | A61K 31/135 514/437 |
| 2002/0182198 A1 | | 12/2002 | Commissiong et al. | |
| 2003/0125242 A1 | * | 7/2003 | Rosenecker | A61K 47/48276 514/1.2 |
| 2005/0215558 A1 | * | 9/2005 | Cincotta | A61K 31/498 514/250 |
| 2009/0282495 A1 | | 11/2009 | Saarma et al. | |
| 2011/0123443 A1 | | 5/2011 | Zhou et al. | |
| 2011/0212055 A1 | | 9/2011 | Commissiong | |
| 2011/0212465 A1 | * | 9/2011 | Roessler | G01N 33/57423 435/7.4 |

FOREIGN PATENT DOCUMENTS

| CN | 102083456 | 6/2011 |
| EP | 2322147 A1 | 5/2011 |

(Continued)

OTHER PUBLICATIONS

Laybutt DR et al. 2007. Endoplasmic reticulum stress contributes to beta cell apoptosis in type 2 diabetes. Diabetologia 50: 752-763.*
Parkash V et al. 2009. The structure of the conserved neurotrophic factors MANF and CDNF explains why they are bifunctional. Prot Eng Des Select 22: 233-241.*
Cnop M et al. 2005. Mechanisms of Pancreatic Beta-Cell Death in Type 1 and Type 2 Diabetes: Many Differences, Few Similarities. Diabetes 54 (Suppl 2): S97-S107.*
NCBI Protein database. "Chain A, Human Mesencephalic Astrocyte-Derived Neurotrophic Factor (Manf)." PDB No. 2W51_A. Available online at <http://www.ncbi.nlm.nih.gov/protein/2W51_A>. Accessed Aug. 2, 2016. 2 pages.*

(Continued)

*Primary Examiner* — Gyan Chandra
(74) *Attorney, Agent, or Firm* — Fish & Richardson P.C.

(57) ABSTRACT

The invention provides, in part, methods for diagnosing a pancreatic β-cell disorder, predicting a subject's risk of developing a pancreatic β-cell disorder, monitoring pancreatic β-cell function or pancreatic β-cell mass in a subject at risk of developing a pancreatic β-cell disorder, monitoring efficacy of a treatment of a pancreatic β-cell disorder in a subject, identifying a subject having an increased risk of developing a pancreatic β-cell disorder, selecting a subject for treatment of a pancreatic β-cell disorder, selecting a subject for participation in a clinical study, and detecting endoplasmic reticulum stress in a pancreatic β-cell. These methods include determining at least one level of soluble mesencephalic astrocyte-derived neurotrophic factor (MANF) in a biological sample from the subject. Also provided are pharmaceutical compositions containing a soluble MANF protein and kits containing an antibody or an antigen-binding antibod fragment that binds specifically to a soluble MANF.

17 Claims, 25 Drawing Sheets

(56) References Cited

FOREIGN PATENT DOCUMENTS

| WO | WO 2005/005472 | 1/2005 |
|---|---|---|
| WO | WO 2010/072383 | 7/2010 |
| WO | WO 2011/143788 | 11/2011 |
| WO | WO 2011/152658 | 12/2011 |
| WO | WO 2013/034805 | 3/2013 |

OTHER PUBLICATIONS

Mizobuchi N et al. 2007. ARMET is a soluble ER protein induced by the unfolded protein response via ERSE-II element. Cell Struct Funct 32: 41-50.*
Hohmeier H et al. 2000. Isolation of INS-1—Derived Cell Lines With Robust ATP-Sensitive K+ Channel-Dependent and -Independent Glucose-Stimulated Insulin Secretion. Diabetes 49: 424-430.*
Hectors TLM et al. 2013. Evaluation of the INS-1 832/13 Cell Line as a Beta-Cell Based Screening System to Assess Pollutant Effects on Beta-Cell Function. PLoS ONE 8(3): e60030. 10 pages.*
The State Intellectual Property Office of P.R. China, Notification of First Office Action issued in Patent No. 201380016366.1 dated Jul. 2, 2015 (w/English Translation), 9 pages.
Partial Supplementary European Search Report, Communication pursuant to Rule 164(1) EPC dated Jun. 23, 2015 for corresponding EP Application No. 13741203.7, 8 pages.
Lindahl et al., "MANF is Indispensable for the Proliferation and Survival of Pancreatic β Cells", Cell Reports 7:366-375 (Apr. 24, 2014).
New Zealand Intellectual Property Office, First Examination Report issued in related Application No. 627538 dated Apr. 21, 2015, 3 pages.
Notification of Transmittal of the International Search Report and the Written Opinion of the International Searching Authority, or the Declaration, Int. Appl. No. PCT/US2013/022768, dated May 15, 2013, 13 pages.
Notification Concerning Transmittal of International Preliminary Report on Patentability (Chapter I of the Patent Cooperation Treaty), Int. Appl. No. PCT/US2013/022768, dated Aug. 7, 2014, 8 pages.
Fonseca et al., "Endoplasmic reticulum stress and pancreatic beta cell death," Trends Endocrinol. Metab. 22:266-274, 2011.
Oslowski et al., "The binary switch between life and death of ER stressed beta cells," Curr. Opin. Endocrinol. Diabetes Obes. 17:107-112, 2010.
Oslowski et al., "The binary switch that controls the life and death decisions of ER stressed beta cells," Curr. Opin. Cell Biol. 23:207-215, 2011.
Riggs et al., "Mice conditionally lacking the Wolfram gene in pancreatic islet beta cells exhibit diabetes as a result of enhanced endoplasmic reticulum stress and apoptosis," Diabetologia 48:2313-2321, 2005.
Tadimalla et al., "Mesencephalic Astrocyte-derived Neurotrophic Factor (MANF) is an Ischemia-inducible Secreted Endoplasmic Reticulum (ER) Stress Response Protein in the Heart," Circulation Res. 103:1249-1258, 2008.
Voutilainen et al., "Mesencephalic Astrocyte-Derived Neurotrophic Factor is Neurorestorative in Rat Model of Parkinson's Disease," J. Neurosci. 29:9651-9659, 2009.
Apostolou, A. et al., "Armet, a UPR-upregulated protein, inhibits cell proliferation and ER stress-induced cell death", Exp Cell Res., vol. 14(13):2454-67 (2008).
English translation of the Second Office Action for corresponding CN Appl. No. 201380016366.1 dated Feb. 19, 2016, 5 pp.
Japanese Office Action in Japanese Application No. 2014-554800, dated Oct. 25, 2016, 5 pages (English translation).

* cited by examiner

IP: rabbit anti-MANF (Proteintech)
IB: rabbit anti-MANF (Proteintech)

| Gene | Average Reduced (log2) | Average Oxidized (log2) | Difference (Reduced-Oxidized) (log2) | p-value |
|---|---|---|---|---|
| Derlin3 | 8.92297307 | 8.43722219 | 0.48575088 | 0.0002205 |
| BiP | 13.6816986 | 13.5347029 | 0.14699569 | 0.02232816 |
| Herp | 10.9968278 | 10.6206649 | 0.37616266 | 0.00079626 |
| PDIa5 | 7.68002865 | 7.49100064 | 0.18902801 | 0.00776143 |

DNA microarray

SOLUBLE MANF IN PANCREATIC β-CELL DISORDERS

CLAIM OF PRIORITY

This application is a national stage application under 35 U.S.C. § 371 of International Patent Application No. PCT/US2013/022768, filed on Jan. 23, 2013, which claims priority to U.S. Provisional Patent Application Ser. No. 61/590,021, filed on Jan. 24, 2012, each of these applications are hereby incorporated by reference in their entirety.

BACKGROUND OF THE INVENTION

Loss of the function or number of pancreatic β-cells in a subject contributes to the pathogenesis of several diseases, including type 1 diabetes (diabetes mellitus), type 2 diabetes, and Wolfram syndrome. In type 1 diabetes, the patient has high blood glucose levels because of insulin deficiency. Generally speaking, absolute deficiency of insulin occurs in patients with type 1 diabetes, whereas relative deficiency of insulin occurs in patients with type 2 diabetes. Increasing evidence indicates that reduced functional pancreatic β-cell mass is a common feature of both type 1 and type 2 diabetes, as well as genetic forms of diabetes such as Wolfram syndrome (Pipeleers et al., *Novartis Found Symp.* 292:19-24, 2008). During the progression of type 1 or type 2 diabetes, pancreatic β-cell function and mass gradually decline, eventually leading to insulin deficiency and hyperglycemia. Recent findings indicate that "stressed" pancreatic β-cells are susceptible to dysfunction and death (Oslowski et al., *Curr. Opin. Endocrinol. Diabetes Obes.* 17:107-112, 2010; Oslowski et al., *Curr. Opin. Cell Biol.* 23:207-215, 2011; Fonseca et al., *Trends Endocrinol. Metab.* 22:266-274, 2011). Diagnostic markers that aid in predicting the susceptibility of a subject to develop pancreatic β-cell dysfunction and death will be helpful for treating or delaying the progression of pancreatic β-cell disorders (e.g., type 1 or type 2 diabetes) in subjects.

SUMMARY OF THE INVENTION

The invention is based, in part, on the discovery that stressed pancreatic β-cells produce and secrete soluble mesencephalic astrocyte-derived neurotrophic factor (MANF), soluble MANF protects pancreatic β-cells from endoplasmic reticulum stress-induced apoptosis, and soluble MANF maintains endoplasmic reticulum redox homeostasis in pancreatic β-cells.

In view of these discoveries, provided herein are methods (e.g., in vitro methods) of diagnosing a pancreatic β-cell disorder in a subject, predicting a subject's risk of developing a pancreatic β-cell disorder, monitoring pancreatic β-cell function or pancreatic β-cell mass in a subject (e.g., a subject at risk of developing a pancreatic β-cell disorder), identifying a subject having an increased risk of developing a pancreatic β-cell disorder, selecting a subject for treatment of pancreatic β-cell disorder, selecting a subject for participation in a clinical study, and detecting endoplasmic reticulum stress in a pancreatic β-cell. These methods include determining at least one level of soluble MANF (e.g., endogenous levels of soluble MANF in a biological sample from the subject or in a culture medium).

Also provided herein are methods (e.g., in vitro methods) of diagnosing a pancreatic β-cell disorder in a subject that include determining a level of soluble mesencephalic astrocyte-derived neurotrophic factor (MANF) in a biological sample from a subject; comparing the level of soluble MANF in the biological sample to a reference level of soluble MANF; and identifying a subject having an elevated level of soluble MANF in the biological sample as compared to the reference level as having a pancreatic β-cell disorder.

Also provided herein are methods (e.g., in vitro methods) of predicting a subject's risk of developing a pancreatic β-cell disorder that include: determining a level of soluble mesencephalic astrocyte-derived neurotrophic factor (MANF) in a biological sample from a subject; comparing the level of soluble MANF in the biological sample to a reference level of soluble MANF; and identifying a subject having an elevated level of soluble MANF in the biological sample compared to the reference level as having an increased risk of developing a pancreatic β-cell disorder, or identifying a subject that has a decrease or no significant difference in the level of soluble MANF in the biological sample as compared to the reference level as having a normal or decreased risk of developing a pancreatic β-cell disorder.

Also provided herein are methods (e.g., in vitro methods) of monitoring pancreatic β-cell function or pancreatic β-cell mass in a subject that include: determining a level of soluble mesencephalic astrocyte-derived neurotrophic factor (MANF) in a biological sample from the subject at a first time point; determining a level of soluble MANF in a biological sample from the subject at a second time point; comparing the level of soluble MANF in the biological sample at the second time point to the level of soluble MANF in the biological sample at the first time point; and identifying a subject having an elevated level of soluble MANF in the biological sample at the second time point compared to the level of soluble MANF in the biological sample at the first time point as having a decrease in pancreatic β-cell function or a decrease in pancreatic β-cell, or identifying a subject having a decrease or no significant change in the level of soluble MANF in the biological sample at the second time point compared to the level of soluble MANF in the biological sample at the first time point as having no change or an increase in pancreatic β-cell function, or no change or an increase in pancreatic β-cell mass in the subject.

Also provided are methods (e.g., in vitro methods) of monitoring the efficacy of treatment of a pancreatic β-cell disorder in a subject. These methods include determining a level of soluble MANF in a biological sample from the subject at a first time point, determining a level of soluble MANF in a biological sample from the subject at a second time point, and comparing the level of soluble MANF in the biological sample at the second time point to the level of soluble MANF in the biological sample at the first time point, where (i) the first time point is prior to treatment and the second time point is any time point following the initiation of treatment, or (ii) the first time point is following the initiation of treatment and the second time point is at a later time point during or after treatment; and a decreased level of soluble MANF in the biological sample at the second time point compared to the level of soluble MANF in the biological sample at the first time point indicates that the treatment was effective in the subject.

Also provided are methods of treating or delaying the onset of a pancreatic β-cell disorder in a subject, methods (e.g., in vitro methods) of reducing endoplasmic reticulum stress in a pancreatic β-cell, or methods (e.g., in vitro methods) of reducing or delaying endoplasmic reticulum stress-induced apoptotic cell death in a population of two or more pancreatic β-cells. These methods include the administration of an effective amount of a soluble MANF or apomorphine to a subject, or contacting the pancreatic β-cell or the population of pancreatic β-cells with a soluble MANF or apomorphine. In some embodiments, the soluble MANF contains a sequence that is at least 80% (e.g., 85%, 90%, 91%, 92%, 93%, 94%, 95%, 96%, 97%, 98%, 99%, or 100%) identical to a mammalian soluble MANF protein sequence (e.g., any one of SEQ ID NOS: 2 and 4-7). In some embodiments, e.g., wherein the method includes administering apomorpine, the subject does not have erectile dysfunction or Parkinson's disease.

Also provided herein are methods of methods of using any of the soluble MANF described herein (e.g., a soluble MANF comprising a sequence that is at least 80% identical to SEQ ID NO: 2) or apomorphine in the manufacture of a medicament for treating or delaying the onset of a pancreatic β-cell disorder in a subject. Also provided herein are isolated soluble MANF (e.g., an isolated soluble MANF comprising a sequence that is at least 80% identical to SEQ ID NO: 2) or apomorphine for use in treating or delaying the onset of a pancreatic β-cell disorder in a subject.

Also provided herein are methods (e.g., in vitro methods) of screening for a candidate compound useful for treating or delaying the onset of a pancreatic β-cell disorder in a subject, methods (e.g., in vitro methods) for decreasing endoplasmic reticulum stress in a pancreatic β-cell, and methods (e.g., in vitro methods) for reducing or delaying endoplasmic reticulum stress-induced apoptotic cell death in pancreatic β-cells. These methods include providing a pancreatic β-cell, contacting the pancreatic β-cell with a candidate compound, determining the level of soluble MANF produced by the pancreatic β-cell in the presence of the candidate compound, comparing the level of soluble MANF produced by the pancreatic β-cell to a reference level of soluble MANF, and selecting a compound that is associated with an elevated level of soluble MANF being produced by the pancreatic β-cell compared to the reference level as a candidate compound for treating or delaying the onset of a pancreatic β-cell disorder in a subject. In these methods, an elevated level of soluble MANF produced by the pancreatic β-cell compared to the reference level indicates that the candidate compound may be useful for treating or delaying the onset of a pancreatic β-cell disorder in a subject, decreasing endoplasmic reticulum stress in a pancreatic β-cell, or reducing or delaying endoplasmic reticulum stress-induced apoptotic cell death in pancreatic β-cells.

Also provided are methods (e.g., in vitro methods) of screening for a candidate compound useful for treating or delaying the onset of a pancreatic β-cell disorder in a subject, decreasing endoplasmic reticulum stress in a pancreatic β-cell, or reducing or delaying endoplasmic reticulum stress-induced apoptotic cell death in pancreatic β-cells. These methods include providing a mammalian cell (e.g., a pancreatic β-cell) expressing a reporter protein containing a BiP signal sequence, a redox-sensitive fluorescent protein (e.g., a redox-sensitive green fluorescent protein), and the amino acid sequence of KDEL; contacting the cell with a test compound; determining the amount of oxidized reporter protein present in the cell; and comparing the amount of oxidized reporter protein present in the cell to a reference level; where an elevated level of oxidized reporter protein in the cell compared to the reference level indicates that the candidate compound may be useful for treating or delaying the onset of a pancreatic β-cell disorder in a subject. In some embodiments, the reference level is the amount of oxidized reporter protein present in a mammalian cell in the absence of the candidate agent. In some embodiments, the reference level is a threshold level of oxidized reporter protein.

Also provided are methods (e.g., in vitro methods) of screening for a candidate compound useful for treating or delaying the onset of a pancreatic β-cell disorder in a subject, decreasing endoplasmic reticulum stress in a pancreatic β-cell, or reducing or delaying endoplasmic reticulum stress-induced apoptotic cell death in pancreatic β-cells. These methods include providing a mammalian cell (e.g., a pancreatic β-cell) expressing a reporter protein containing a BiP signal sequence, a redox-sensitive fluorescent protein (e.g., a green fluorescent protein), and the amino acid sequence of KDEL; contacting the cell with a test compound; determining the amount of reduced reporter protein present in the cell; and comparing the amount of reduced reporter protein present in the cell to a reference level; where a decreased level of reduced reporter protein in the cell compared to the reference level indicates that the candidate compound may be useful for treating or delaying the onset of a pancreatic β-cell disorder in a subject. In some embodiments, the reference level is the amount of reduced reporter protein present in a mammalian cell in the absence of the candidate agent. In some embodiments, the reference level is a threshold level of reduced reporter protein.

Also provided are kits including an antibody or antigen-binding antibody fragment that binds specifically to a soluble MANF (e.g., a human soluble MANF), and at least one antibody or antigen-binding antibody fragment that binds to a protein selected from insulin, C-protein, and islet amyloid polypeptide (IAPP). Also provided are pharmaceutical compositions that contain a soluble MANF protein (e.g., a soluble MANF protein containing a sequence at least 80% identical to SEQ ID NO: 2) and/or apomorphine, and at least one additional agent for treating a pancreatic β-cell disorder (e.g., pioglitazone, TUDCA, GLP-1, or a DPP-4 inhibitor (e.g., sitagliptin, vildagliptin, saxagliptin, linagliptin, dutogliptin, gemigliptin, and alogliptin)).

By the term "pancreatic β-cell disorder" is meant a disease that includes, as part of its pathogenesis, a decrease in pancreatic β-cell function (e.g., insulin secretion) or a decrease in the number of viable insulin-secreting pancreatic β-cells present in a subject (pancreatic β-cell mass). In some embodiments, a pancreatic β-cell disorder can be further characterized by an increase in the endoplasmic reticulum stress in a population of pancreatic β-cells (e.g., two or more pancreatic β-cells) in the subject. As described herein a decrease in pancreatic β-cell function, a decrease in the number of viable pancreatic β-cells (pancreatic β-cell mass), or an increase in the endoplasmic reticulum stress in pancreatic β-cells present in a subject can be detected indirectly using the methods described herein or other methods known in the art. Non-limiting examples of pancreatic β-cell disorders include type 1 diabetes (diabetes mellitus), type 2 diabetes, and Wolfram syndrome.

By the term "pancreatic β-cell function" is meant a biological activity that is used to describe a mammalian (e.g., human) pancreatic β-cell (e.g., an activity that is specifically unique to a pancreatic β-cell). Non-limiting examples of pancreatic β-cell function include the synthesis and secretion of insulin, the synthesis and secretion of islet amyloid polypeptide (LAPP), and the synthesis and section of C-peptide. Methods for detecting the synthesis and secretion of insulin, IAPP, and C-peptide are known in the art. Pancreatic β-cell function can also be detected indirectly using the methods described herein, as well as methods known in the art (e.g., determining blood glucose levels and determining glycated hemoglobin A1C levels).

By the term "pancreatic β-cell mass" is meant the total number of viable insulin-secreting pancreatic β-cells in a mammal (e.g., a human). Methods for indirectly determining the pancreatic β-cell mass in a subject are described herein. Additional methods for indirectly determining the pancreatic β-cell mass in a subject are known in the art (e.g., determining blood glucose levels and determining glycated hemoglobin A1C levels).

The pancreatic β-cell mass may represent the total number of endogenous viable pancreatic β-cells in a subject or may represent the sum of the number of endogenous viable pancreatic β-cells in a subject plus the number of viable pancreatic β-cells transplanted into the subject (e.g., autograft, homograft, or xenografted viable pancreatic β-cells).

By the term "soluble MANF" is meant a protein containing a sequence that is at least 80% identical to a sequence of a soluble mammalian form of mesencephalic astrocyte-derived neutrophic factor (MANF). For example, a soluble MANF can be protein containing a sequence that is at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOS: 2 and 4-7, i.e., to the full length of SEQ ID NOs: 2 or 4-7. In some embodiments, a soluble MANF can be a wildtype mammalian soluble MANF (e.g., SEQ ID NO: 2 and 4-7).

A soluble MANF protein can be administered as a therapeutic treatment (e.g., as a recombinant or purified endogenous protein using any of the methods described herein). A purified soluble MANF protein can be, e.g., at least 80% (e.g., at least 85%, 90%, 95%, or 99%) pure by dry weight. Additional modified forms of soluble MANF are described herein.

By the term "increase" or "elevated" is meant an observable, detectable, or significant increase in a level as compared to a reference level or a level measured at an earlier or later time point in the same subject (e.g., in a biological sample from the same subject).

By the term "decrease" is meant an observable, detectable, or significant decrease in a level as compared to a reference level or a level measured at an earlier or later time point in the same subject (e.g., in a biological sample from the same subject).

By the phrase "a compound that is associated with an elevated level of soluble MANF" is meant a compound that induces or results in an elevated level of soluble MANF (e.g., protein or mRNA) present, produced by, or secreted by a mammalian cell that is contacted with the compound, as compared to the level of soluble MANF (e.g., protein or mRNA) present, produced by, or secreted by a control mammalian cell (e.g., the same or the same type of mammalian cell) in the absence of the compound.

By the phrase "risk of developing disease" is meant the relative probability that a subject will develop a pancreatic β-cell disorder in the future as compared to a control subject or population (e.g., a healthy subject or population, or a subject or population with no family history of a pancreatic β-cell disorder). Provided herein are methods for determining a subject's risk of developing a pancreatic β-cell disorder (in the future) that include determining a level of soluble MANF.

The term "treating" includes reducing the number of symptoms or reducing the severity, duration, or frequency of one or more symptoms of disease (e.g., a pancreatic β-cell disorder) in a subject. The term treating can also include reducing the risk of developing a pancreatic β-cell disorder in a subject (in the future) or delaying the onset of one or more symptoms of a pancreatic β-cell disorder in a subject.

By the phrase "delaying the onset of a pancreatic β-cell disorder" is meant an increase in the length of time before one or more symptoms of a pancreatic β-cell disorder are observed in a subject. In some embodiments, the subject can be previously identified as having an increased risk of developing a pancreatic β-cell disorder. As described herein, a subject can be identified as having an increased risk of developing a pancreatic β-cell disorder using the methods described herein or by the observation of a family history of a pancreatic β-cell disorder (e.g., type 2 diabetes).

The term "biological sample" includes any sample collected from a subject that includes a biological fluid. In non-limiting samples, the biological sample can include blood, serum, plasma, urine, cerebrospinal fluid, saliva, bile, gastric juice, or breast milk.

By the phrase "endoplasmic reticulum stress" is meant an imbalance the endoplasmic reticulum between the production of reactive oxygen species (pro-oxidant species) and the cell's or cellular organelle's ability to detoxify (remove) the reactive oxygen species (or their intermediates) that results in a shift in the redox potential of the lumen of the endoplasmic reticulum and/or an accumulation of misfolded or unfolded proteins within the lumen of the endoplasmic reticulum. Endoplasmic reticulum stress triggers a unique stress pathway termed the unfolded protein response (UPR) (further described herein).

Endoplasmic reticulum stress in a pancreatic β-cell can be caused by a number of molecular events (e.g., an increased level of free fatty acids in the endoplasmic reticulum, hyperinsulemia, hyper-production of VEGF, hypoxia, glucose deprivation, mutant islet amyloid polypeptide, mutant insulin, increased levels of IL-1, increased levels of IFN-γ, or virus infection). A variety of different chemical agents can also be used to induce endoplasmic reticulum stress (e.g., thapsigargin or tunicamycin). Endoplasmic reticulum stress has been shown to shift the endoplasmic reticulum from an oxidizing environment towards a more reducing environment. In some embodiments, agents that have the ability to shift the endoplasmic reticulum from a reducing toward an oxidizing environment under ER stress conditions will help reduce ER stress and/or may reduce or prevent ER stress-induced apoptotic cell death.

Endoplasmic reticulum stress can be detected using a variety of different methods known in the art. Exemplary methods for detecting, reducing, or delaying the onset of endoplasmic reticulum stress in pancreatic β-cells are described herein.

By the phrase "population of pancreatic β-cells" is meant two or more pancreatic ≠-cells. In some embodiments, a population of pancreatic β-cells may be present in a mammalian (e.g., human) subject (e.g., a subject's endogenous pancreatic β-cells, an autograft, homograft, or xenograft of pancreatic β-cells). In some embodiments, a population of pancreatic β-cells can be cultured in vitro (tissue culture). In some embodiments, a population of pancreatic β-cells is pancreatic β-cell line (e.g., those pancreatic β-cell lines described herein). In some embodiments, a pancreatic β-cell can be derived from any mammalian species (e.g., human, monkey (e.g., chimpanzee), mouse, pig, rat, or ape). In some embodiments, a pancreatic β-cell population can be a primary cell line or an immortalized cell line.

By the term "pancreatic β-cell" is meant an insulin-producing cell that is normally present in the pancreas of a mammal in the islet of Langerhans. As used herein, the term pancreatic β-cell encompasses a pancreatic β-cell present in the body of a mammal (e.g., endogenous pancreatic β-cells, or autograft, homograft, or xenograft pancreatic β-cells) or a pancreatic β-cell cultured in vitro (e.g., an ex vivo (e.g., primary) culture of pancreatic β-cells from any mammalian species described herein or a pancreatic β-cell line (e.g., a primary or immortalized cell line). In some embodiments, the pancreatic β-cell present in a mammal is present in the pancreas. In some embodiments, the pancreatic β-cell present in a mammal is located in a tissue other than the pancreas (e.g., in liver tissue). In other embodiments, the pancreatic β-cell is encapsulated in a device (e.g., a biocompatible polymer) that is implanted in the subject. The term pancreatic β-cell also encompasses a pancreatic β-cell in a mammalian (e.g., human, pig, rat, and mouse) cell line or a primary mammalian (e.g., human, pig, rat, and mouse) cell culture. In some embodiments, the pancreatic β-cell can be genetically manipulated using molecular biology techniques to express one or more recombinant proteins (e.g., an insulin) and/or decrease the expression of one or more endogenous proteins.

By the term "endoplasmic reticulum-induced apoptotic cell death" is meant programmed cell death that is triggered by stress in the endoplasmic reticulum of a cell (e.g., a pancreatic β-cell). In some embodiments, the endoplasmic reticulum stress that induces apoptotic cell death induces the unfolded protein response (UPR) pathway in the cell (e.g., a pancreatic β-cell). Exemplary components of the UPR pathway are described herein. As described herein, endoplasmic reticulum stress can be caused by a number of agents (e.g., biological and chemical agents). Methods for detecting, measuring, decreasing, and delaying the onset of endoplasmic reticulum-induced apoptotic cell death in pancreatic β-cells are described herein. Additional methods for detecting and measuring endoplasmic reticulum-induced apoptotic cell death are known in the art.

By the term "determining a level" is meant the use of one or more scientific techniques (e.g., molecular biology, molecular genetics, immunological, and biochemical methods or assays) to assess the level of a particular molecule (e.g., in a biological sample or cell culture medium). The phrase determining a level includes the physical contacting of one or more reagents that specifically bind to a particular molecule (e.g., an antibody or antigen-binding fragment of an antibody) to a sample (e.g., a biological sample or cell culture medium).

By the term "second time point" generally means any point in time that occurs after a first time point (e.g., time of admission). A second time point can occur, e.g., at least 6 hours, 12 hours, 24 hours, 1 day, 2 days, 3 days, 4 days, 5 days, 6 days, 1 week, 2 weeks, 3 weeks, 4 weeks, 6 weeks, 2 months, 6 months, 1 year, or 2 years after the first time point. In some embodiments, a subject can be administered a treatment between the first time point and the second time point.

By the term "redox-sensitive fluorescent protein" is a protein that changes its fluorescence properties (e.g., change in excitation and/or emission spectrum (e.g., peak excitation or emission wavelengths) upon a change in its redox environment (e.g., a change in the redox environment of the endoplasmic reticulum). In some embodiments, this change in the fluorescence properties of the protein can occur, e.g., as a result of the formation and/or breakage of one or more disulfide bonds. Non-limiting examples of redox-sensitive fluorescent proteins include redox-oxidation sensitive green fluorescent protein (roGFP) and redox-sensitive yellow fluorescent protein (rxYFP). Additional redox-sensitive fluorescent proteins are known in the art.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Figure 1:
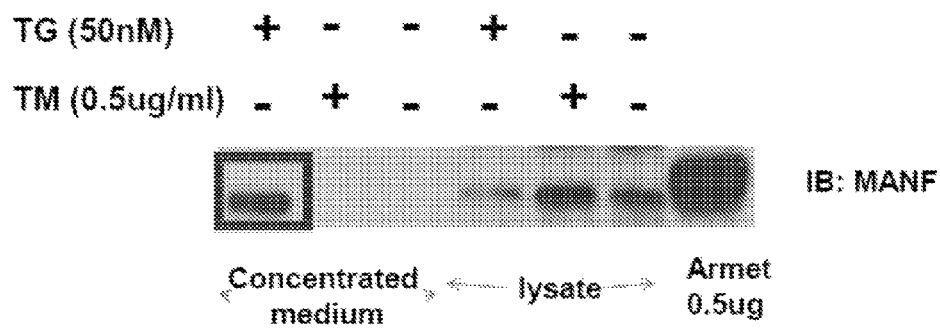
FIG. 1 is an immunoblot showing the levels of MANF protein in concentrated medium from a culture of a rat pancreatic β-cell line (INS-1 832/13) or in lysate from the rat pancreatic β-cell line (INS-1 832/13) after no treatment or treatment with thapsigargin (50 nM) or tunicamycin (0.5 μg/mL) for 24 hours.

The invention is based, at least in part, on the discovery that soluble MANF is secreted by stressed pancreatic β-cells, and that soluble MANF delays endoplasmic reticulum stress-induced pancreatic β-cell apoptotic cell death and reduces fluctuation in the redox state of the endoplasmic reticulum in pancreatic β-cells exposed to agents or conditions that induce endoplasmic reticulum stress. In view of these discoveries, methods for diagnosing a pancreatic β-cell disorder, predicting a subject's risk of developing a pancreatic β-cell disorder, monitoring pancreatic β-cell function and pancreatic β-cell mass in a subject (e.g., a subject at risk of developing a pancreatic β-cell disorder), monitoring the efficacy of treatment of a pancreatic β-cell disorder in a subject, identifying a subject having an increased risk of developing a pancreatic β-cell disorder, selecting a subject for treatment of pancreatic β-cell disorder, selecting a subject for participation in a clinical study, and detecting endoplasmic reticulum stress in a pancreatic β-cell are provided. These methods include determining at least one level of soluble MANF (e.g., in a biological sample from the subject or in a culture medium).

Methods of treating or delaying the onset of a pancreatic β-cell disorder in a subject, reducing endoplasmic reticulum stress in a pancreatic β-cell, and reducing or delaying endoplasmic reticulum stress-induced apoptotic cell death in a population of two or more pancreatic β-cells are also provided. These methods include the administration of an effective amount of a soluble MANF or apomorphine to a subject, or contacting a pancreatic β-cell or a population of pancreatic β-cells with a soluble MANF. In some embodiments, e.g., wherein the method includes administering apomorpine, the subject does not have erectile dysfunction or Parkinson's disease.

Also provided are methods of screening for a candidate compound useful for treating or delaying the onset of a pancreatic β-cell disorder in a subject, decreasing endoplasmic reticulum stress in a pancreatic β-cell, or reducing or delaying endoplasmic reticulum stress-induced apoptotic cell death in pancreatic β-cells. In some embodiments, these methods include providing a pancreatic β-cell, contacting the pancreatic β-cell with a candidate compound, determining the level of soluble MANF produced by the pancreatic β-cell in the presence of the candidate compound, and comparing the level of soluble MANF produced by the pancreatic β-cell to a reference level of soluble MANF. In some embodiments, these methods include providing a mammalian cell (e.g., a pancreatic β-cell) expressing a reporter protein containing a BiP signal sequence, a redox-sensitive fluorescent protein (e.g., a redox-sensitive green fluorescent protein or redox-sensitive yellow fluorescent protein), and the amino acid sequence of KDEL; contacting the cell with a test compound; determining the amount of oxidized reporter protein present in the cell; and comparing the amount of oxidized reporter protein present in the cell to a reference level; where an elevated level of oxidized reporter protein in the cell compared to the reference level indicates that the candidate compound may be useful for treating or delaying the onset of a pancreatic β-cell disorder in a subject, decreasing endoplasmic reticulum stress in a pancreatic β-cell, and/or reducing or delaying endoplasmic reticulum stress-induced apoptotic cell death in pancreatic β-cells. In some embodiments, these methods include providing a mammalian cell (e.g., a pancreatic β-cell) expressing a reporter protein containing a BiP signal sequence, a redox-sensitive fluorescent protein (e.g., a redox-sensitive green fluorescent protein or redox-sensitive yellow fluorescent protein), and the amino acid sequence of KDEL; contacting the cell with a test compound; determining the amount of reduced reporter protein present in the cell; and comparing the amount of reduced reporter protein present in the cell to a reference level; where a decreased level of reduced reporter protein in the cell compared to the reference level indicates that the candidate compound may be useful for treating or delaying the onset of a pancreatic β-cell disorder in a subject, decreasing endoplasmic reticulum stress in a pancreatic β-cell, and/or reducing or delaying endoplasmic reticulum stress-induced apoptotic cell death in pancreatic β-cells.

Pancreatic β-Cell Disorders

Pancreatic β-cell disorders are a class of diseases that are characterized by a progressive decrease in pancreatic β-cell dysfunction or pancreatic β-cell mass in the subject. Pancreatic β-cell functions that can be decreased in a subject having a pancreatic β-cell disorder include, without limitation, insulin production and secretion, C-peptide production and secretion, and islet amyloid polypeptide (IAPP) production and secretion. Non-limiting examples of pancreatic β-cell disorders include type 1 diabetes (diabetes mellitus), type 2 diabetes, and Wolfram syndrome. Pancreatic β-cell disorders can occur in humans at any age, e.g., in infants, children, adults, and elderly subjects. For example, a pancreatic β-cell disorder can occur in a subject having an age of greater than 35, 40, 45, 50, 55, 60, 65, 70, 75, 80, 85, or 90.

A health care professional (e.g., a physician, nurse, physician's assistant, nurse's assistant, or laboratory technician) may diagnose a subject as having a pancreatic β-cell disorder by the assessment of one or more (e.g., two, three, four, or five) symptoms of a pancreatic β-cell disorder in the subject. Non-limiting symptoms of a pancreatic β-cell disorder in a subject include a significant increase in blood glucose levels (e.g., fasting blood glucose levels) compared to a healthy individual or population (e.g., a fasting blood glucose level of greater than 100 mg/dL or greater than 120 mg/dL), a significant increase in glycated hemoglobin levels (hemoglobin A1C level) compared to a healthy individual or population (e.g., a hemoglobin A1C level greater than 6.5%, greater than 7.0%, or greater than 8.0%), increased thirst, frequent urination, extreme hunger, unexplained weight loss, presence of ketones in the urine, fatigue, blurred vision, slow-healing sores, mild high blood pressure, and frequent infections. A health care professional may also base a diagnosis, in part, on the subject's family history of a pancreatic β-cell disorder. A health care professional may diagnose a subject as having a pancreatic β-cell disorder upon presentation of a subject to a health care facility (e.g., a clinic or a hospital). In some instances, a health care professional may diagnose a subject as having a pancreatic β-cell disorder while the subject is admitted in an assisted care facility. Typically, a physician diagnoses a pancreatic β-cell disorder in a subject after the observation or detection of one or more symptoms in the subject.

A health care professional may also identify a subject as having an increased risk of developing a pancreatic β-cell disorder based on one of more of the following factors: increased weight (e.g., a body mass index of >25 or >30), inactivity, family history of a pancreatic β-cell disorder, race, age, diagnosis with polycystic ovary syndrome, high blood pressure, decreased high-density lipoprotein levels (e.g., below 35 mg/dL), and high levels of triglycerides (e.g., above 250 mg/dL).

Provided herein are additional methods for diagnosing a pancreatic β-cell disorder in a subject (e.g., a subject presenting with one or more symptoms of a pancreatic β-cell disorder or a subject not presenting with a symptom of a pancreatic β-cell disorder (e.g., an undiagnosed and/or asymptomatic subject). Also provided are additional methods of identifying a subject having an increased risk of developing a pancreatic β-cell disorder. Also provided herein are methods of treating a pancreatic β-cell disorder in a subject.

Mesencephalic Astrocyte-Derived Neurotrophic Factor (MANF)

An endogenous level of soluble MANF protein, as described herein, can be detected in any of the methods described herein, e.g., as a marker for diagnosing a pancreatic β-cell disorder, predicting a subject's risk of developing a pancreatic β-cell disorder, monitoring pancreatic β-cell function and pancreatic β-cell mass in a subject (e.g., a subject at risk of developing a pancreatic β-cell disorder), identifying a subject having an increased risk of developing a pancreatic β-cell disorder, selecting a subject for treatment of pancreatic β-cell disorder, selecting a subject for participation in a clinical study, and detecting endoplasmic reticulum stress in a pancreatic β-cell. A purified, isolated, and/or recombinant soluble MANF protein can also be used in methods of treating or delaying the onset of a pancreatic β-cell disorder in a subject, reducing endoplasmic reticulum stress in a pancreatic β-cell, and reducing or delaying endoplasmic reticulum stress-induced apoptotic cell death in a population of two or more pancreatic β-cells.

MANF protein is translated as a precursor protein that is subsequently cleaved and released as a soluble protein from a cell (e.g., a pancreatic β-cell). The full-length (precursor) human MANF protein and the human soluble MANF protein are shown below. The 25-amino acid signal sequence in the precursor human MANF protein is underlined below. Also shown below is the mRNA encoding the human precursor MANF protein.

```
Human precursor MANF Protein
                                             (SEQ ID NO: 1)
MRRMWATQGLAVALALSVLPGSRALRPGDCEVCISYLGRFYQDLKDRDVT

FSPATIENELIKFCREARGKENRLCYYIGATDDAATKIINEVSKPLAHHI

PVEKICEKLKKKDSQICELKYDKQIDLSTVDLKKLRVKELKKILDDWGET

CKGCAEKSDYIRKINELMPKYAPKAASARTDL

Human soluble MANF Protein
                                             (SEQ ID NO: 2)
LRPGDCEVCISYLGRFYQDLKDRDVTFSPATIENELIKFCREARGKENRL

CYYIGATDDAATKIINEVSKPLAHHIPVEKICEKLKKKDSQICELKYDKQ

IDLSTVDLKKLRVKELKKILDDWGETCKGCAEKSDYIRKINELMPKYAPK

AASARTDL

Human MANF mRNA
                                             (SEQ ID NO: 3)
ggaggaggag cggcgcggcg ggtgcggttc agtcggtcgg cggcggcagc ggaggaggag gaggaggagg aggaggagga ggatgaggag gatgtgggcc acgcagggc tggcggtggc gctggctctg agcgtgctgc cgggcagccg ggcgctgcgg ccgggcgact gcgaagtttg tatttcttat ctgggaagat tttaccagga cctcaaagac agagatgtca cattctcacc agccactatt gaaaacgaac ttataaagtt ctgccgggaa gcaagaggca aagagaatcg gttgtgctac tatatcgggg ccacagatga tgcagccacc aaaatcatca atgaggtatc aaagcctctg gcccaccaca tccctgtgga aagatctgt gagaagctta agaagaagga cagccagata tgtgagctta agtatgacaa gcagatcgac ctgagcacag tggacctgaa gaagctccga gttaaagagc tgaagaagat tctggatgac tggggggaga catgcaaagg ctgtgcagaa aagtctgact acatccggaa gataaatgaa ctgatgccta aatatgcccc caaggcagcc agtgcacgga ccgatttgta gtctgctcaa tctctgttgc acctgagggg gaaaaaacag ttcaactgct tactcccaaa acagccttt tgtaatttat tttttaagtg ggctcctgac aatactgtat cagatgtgaa gcctggagct ttcctgatga tgctggccct acagtacccc catgagggga ttcccttcct tctgttgctg gtgtactcta ggacttcaaa gtgtgtctgg gattttttta ttaaagaaaa aaaatttcta gctgtccttg cagaattata gtgaatacca aaatggggtt ttgccccagg aggctcctaa aaaaaaaaaa aaaaaaaaaa aaaaaaaaa
```

Cow, rat, mouse, pig, fly, and zebrafish soluble MANF protein sequences have also been described, and are shown below.

```
Cow soluble MANF
                                             (SEQ ID NO: 4)
LRQGDCEVCISYLGRFYQDLKDRDVTFSPASIEKELIKFCREARGKENRL

CYYIGATEDAATKIINEVSKPLSHHIPVEKICEKLKKKDSQICELKYDKQ

IDLSTVDLKKLRVKELKKILDDWGETCKGCAEKSDYIRKINELMPKYAPK

AASSRTDL

Rat soluble MANF
                                             (SEQ ID NO: 5)
LRPGDCEVCISYLGRFYQDLKDRDVTFSPATIEEELIKFCREARGKENRL

CYYIGATDDAATKIINEVSKPLAHHIPVE KICEKLKKKDSQICELKYGE

CD

Mouse soluble MANF
                                             (SEQ ID NO: 6)
LRPGDCEVCISYLGRFYQDLKDRDVTFSPATIEEELIKFCREARGKENRL

CYYIGATDDAATKIINEVSKPLAHHIPVEKICEKLKKKDSQICELKYDKQ

IDLSTVDLKKLRVKELKKI LDDWGEMCKGCAEKSDYIRK INELMPKYA

PKAASARTDL

Pig soluble MANF
                                             (SEQ ID NO: 7)
LRPGDCEVCISYLGRFYQDLKDRDVTFSPASIEKELTKFCREARGKENRL

CYYIGATDDAATKIINEVSKPLAHHIPVEKICEKLKKKDSQICELKYDKQ

IDLSTVDLKKLRVKELKKILDDWGETCKGCAEKSDYIRKINELMPKYAPK

AASSRTD

Drosophila melanogaster soluble MANF
                                             (SEQ ID NO: 8)
LKEEDCEVCVKTVRRFADSLDDSTKKDYKQIETAFKKFCKAQKNKEHRFC

YYLGGLEESATGILNELSKPLSWSMPAEKICEKLKKKDAQICDLRYEKQI

DLNSVDLKKLKVRDLKKILNDWDESCDGCLEKGDFIKRIEELKPKYSR

SEL

Zebrafish soluble MANF
                                             (SEQ ID NO: 9)
LKDGECEVCVGFLQRLYQTIQENNVKFDSDSIEKALLKSCKDAKGKENRF

CYYIGATSDAATKITNEVSKPMSYHVPVEKICEKLKKKDSQICELKYDKQ

VDLSSVDLKKLKVKDLKKILEEWGESCKGCVEKSDFIRKINELMPKYAPS

AAKARTDL
```

Mammalian soluble MANF proteins are highly conserved, with human and cow soluble MANF proteins having 96% identity, human and mouse soluble MANF proteins having 99% identity, and human and pig soluble MANF proteins having 97% identity. Human soluble MANF protein also shares 72% identity and 88% similarity with zebrafish soluble MANF protein.

Diagnostic Methods

Provided herein are methods of diagnosing a pancreatic β-cell disorder in a subject. These methods include determining (assaying) a level of soluble MANF in a biological sample from a subject, and comparing the level of soluble MANF in the biological sample to a reference level of soluble MANF. In these methods, an elevated level of soluble MANF in the biological sample as compared to the reference level of soluble MANF indicates that the subject has a pancreatic β-cell disorder, and a decrease or no significant change in the level of soluble MANF in the biological sample as compared to the reference level of soluble MANF indicates that the subject does not have a pancreatic β-cell disorder.

As referred to anywhere herein, a "reference level of soluble MANF" can be a threshold level of soluble MANF, a level of soluble MANF present in a control subject or population (e.g., a subject or population that is not diagnosed as having a disease (a healthy subject or population), does not have one or more symptoms of a pancreatic β-cell disorder, and/or does not have a family history of a pancreatic β-cell disorder), or a level of soluble MANF in the same subject at an earlier time point.

The levels of soluble MANF can be determined using methods known in the art. For example, the levels of soluble MANF can be detected using a number of techniques known in the art that utilize antibodies that specifically bind to a soluble MANF (e.g., enzyme-linked immunosorbent assay). A number of antibodies that specifically bind to human soluble MANF are commercially available (e.g., rabbit anti-human soluble MANF antibodies available from Sigma-Aldrich and Proteintech).

Any of the methods described herein may further include obtaining or collecting a sample from a subject (e.g., a biological sample containing a biological fluid, e.g., urine, blood, plasma, serum, or cerebrospinal fluid). In any of the methods described herein, the biological sample can be stored for a period of time (e.g., at least one hour or at least 24 hours) before a level of soluble MANF is determined (e.g., storage at or below 10° C.).

Any of the methods described herein can be performed on patients presenting to a health care facility (e.g., a hospital, clinic, or an assisted care facility). The subjects may present with one or more symptoms of a pancreatic β-cell disorder (e.g., any of the symptoms of a pancreatic β-cell disorder described herein). The subject may be suspected of having a pancreatic β-cell disorder. The subject can also present with no symptoms (an asymptomatic subject) or just one symptom of a pancreatic β-cell disorder. The subject can have a family history of a pancreatic β-cell disorder (e.g., type 2 diabetes). The subject can also have an increased risk of developing a pancreatic β-cell disorder. The subject can be an infant, a child, a teenager, an adult, or an elderly person.

In some embodiments, the methods are performed on a subject that has a detectable or observable pancreatic β-cell mass and/or has detectable or observable amount pancreatic β-cell function (e.g., a subject that does not have a complete loss of pancreatic β-cell mass or pancreatic β-cell function). Methods of detecting pancreatic β-cell function are described herein. Pancreatic β-cell mass can be detected indirectly by observing pancreatic β-cell function in a subject or using methods known in the art (e.g., the methods described in U.S. Patent Application Publication No. 20110123443).

The diagnostic methods described herein can be performed by any health care professional (e.g., a physician, a laboratory technician, a nurse, a physician's assistant, and a nurse's assistant). The diagnostic methods described herein can be used in combination with one or more additional diagnostic testing methods known in the art or described herein (e.g., the observation or assessment of one or more symptoms of a pancreatic β-cell disorder in a subject, e.g., blood glucose monitoring, glycated hemoglobin analysis, level of insulin, level of IAPP, level of C-peptide, or ketones in the urine). The diagnostic methods described herein can be performed on a subject identified as having an increased risk of developing a pancreatic β-cell disorder (e.g., a subject identified as having an increased risk of developing a pancreatic β-cell disorder using any of the methods described herein). In some embodiments, the diagnostic methods described herein can be performed periodically (e.g., at least once every month, two months, six months, or year) for a subject that has been identified as having an increased risk of developing a pancreatic β-cell disorder. Some embodiments further include collecting the biological sample from the subject.

Some embodiments further include administering to the subject identified as having, or at risk of developing, a pancreatic β-cell disorder a treatment for a pancreatic β-cell disorder (e.g., an isolated, purified, or recombinant soluble MANF protein, pioglitazone, GLP-1, or a DPP-4 inhibitor (e.g., sitagliptin, vildagliptin, saxagliptin, linagliptin, dutogliptin, gemigliptin, and alogliptin), or any of the compositions described herein, e.g., an therapeutically effective dose of a soluble MANF protein containing a sequence at least 90% identical to SEQ ID NO: 2 and/or apomorphine). Some embodiments further include performing additional tests to confirm the diagnosis of a pancreatic β-cell disorder in the subject. Some embodiments include selecting the subject for periodic glucose monitoring (e.g., periodic self-glucose monitoring using a glucometer) or any of the monitoring methods described herein. Some embodiments further include selecting the subject for periodic medical evaluation by a physician or a health care professional (e.g., periodic visits of at least once every year, at least once every six months, at least once every three months, at least once every two months, or at least once a month). Some embodiments further include recording the results of the diagnostic test in the subject's medical records, or performing a diagnostic test for a pancreatic β-cell disorder on one or more lineal family members of a subject diagnosed as having a pancreatic β-cell disorder using the methods described herein.

Methods of Predicting the Risk of Developing a Pancreatic β-Cell Disorder

Also provided are methods of predicting a subject's risk of developing a pancreatic β-cell disorder. These methods include determining (assaying) a level of soluble MANF in a biological sample from the subject and comparing the level of the soluble MANF in the biological sample to a reference level of soluble MANF. An elevated level of soluble MANF in the biological sample as compared to the reference level of soluble MANF indicates that the subject has an increased risk of developing a pancreatic β-cell disorder, and a decrease or no significant change in the level of soluble MANF in the biological sample compared to the reference level indicates that the subject has a decreased or no significant risk of developing a pancreatic β-cell disorder. Any of the reference levels of soluble MANF described herein can be used in these methods. Some embodiments further include obtaining the biological sample from the subject.

The levels of soluble MANF can be determined using methods known in the art. For example, the levels of soluble MANF can be detected using a number of techniques known in the art that utilize antibodies that specifically bind to soluble MANF (e.g., enzyme-linked immunosorbent assay). In some embodiments, the methods further include obtaining or collecting a sample from a subject (e.g., a biological sample containing a biological fluid, e.g., urine, blood, plasma, serum, or cerebrospinal fluid).

Any of the methods described herein can be performed on patients presenting to a health care facility (e.g., a hospital, clinic, or an assisted care facility). In some embodiments, the methods are performed on a subject as part of a periodic physical examination by a health care professional. The subjects may present with one or more symptoms of a pancreatic β-cell disorder (e.g., any of the symptoms of a pancreatic β-cell disorder described herein). The subject may be suspected of having a pancreatic β-cell disorder. The subject can also present with no symptoms (an asymptomatic subject) or just one symptom of a pancreatic β-cell disorder. The subject can have a family history of a pancreatic β-cell disorder (e.g., type 2 diabetes). The subject can be an infant, a child, a teenager, an adult, or an elderly person.

These methods described herein can be performed by any health care professional (e.g., a physician, a laboratory technician, a nurse, a physician's assistant, and a nurse's assistant). These methods can be used in combination with any additional methods known in the art for identifying a subject at risk of developing a pancreatic β-cell disorder (e.g., assessment of one of more of the following factors: increased weight, inactivity, family history of a pancreatic β-cell disorder, race, age, diagnosis with polycystic ovary syndrome, high blood pressure, decreased high-density lipoprotein levels (e.g., below 35 mg/dL), and high levels of triglycerides (e.g., above 250 mg/dL)). A subject identified as having an increased risk of developing a pancreatic β-cell disorder can be monitored using any of the methods described herein (see, e.g., the next section).

Some embodiments further include administering to a subject identified as having an increased risk of developing a pancreatic β-cell disorder a treatment for a pancreatic β-cell disorder (e.g., an isolated, purified, or recombinant soluble MANF protein, pioglitazone, GLP-1, or a DPP-4 inhibitor (e.g., sitagliptin, vildagliptin, saxagliptin, linagliptin, dutogliptin, gemigliptin, and alogliptin), or any of the compositions described herein, e.g., a therapeutically effective dose of a soluble MANF protein containing a sequence at least 90% identical to SEQ ID NO: 2 and/or apomorphine). Some embodiments include selecting the subject identified as having an increased risk of developing a pancreatic β-cell disorder for periodic glucose monitoring (e.g., periodic self-glucose monitoring using a glucometer). Some embodiments further include selecting a subject identified as having an increased risk of developing a pancreatic β-cell disorder for periodic medical evaluation by a physician or a health care professional (e.g., periodic visits of at least once every year, at least once every six months, at least once every three months, at least once every two months, or at least once a month). Some embodiments further include recording the results of the test in the subject's medical records, or performing a similar test or any art-known test to determine the risk of developing a pancreatic β-cell disorder in one or more lineal family members of a subject identified as having an increased risk of developing a pancreatic β-cell disorder using any of the methods described herein.

Methods of Monitoring Pancreatic β-Cell Dysfunction and Pancreatic β-Cell Mass

Also provided are methods of monitoring pancreatic β-cell dysfunction in a subject (e.g., a subject at risk of developing a pancreatic β-cell disorder, a subject having a pancreatic β-cell disorder, or a subject that has received a pancreatic β-cell transplant). These methods include determining (assaying) a level of soluble MANF in a biological sample from the subject at a first time point, determining (assaying) a level of soluble MANF in a biological sample from the subject at a second time point, and comparing the level of soluble MANF in the biological sample at the second time point to the level of soluble MANF in the biological sample at the first time point. An elevated level of soluble MANF in the biological sample at the second time point compared to the level of soluble MANF at the first time point indicates a decrease (e.g., a significant, observable, or detectable decrease) in pancreatic β-cell function or a decrease in pancreatic β-cell mass in the subject. A decrease or no significant change in the level of soluble MANF in the biological sample at the second time point compared to the level of soluble MANF in the biological sample at the first time point indicates no change or an increase in pancreatic β-cell function or pancreatic β-cell mass in the subject.

In some embodiments, the methods are performed on a subject that has a detectable or observable pancreatic β-cell mass and/or has detectable or observable amount pancreatic β-cell function at the first and the second time point (e.g., a subject that does not have a complete loss of pancreatic β-cell mass or pancreatic β-cell function at the first and the second time point).

In some embodiments, the second time point can be at least 6 hours (e.g., at least 12 hours, 18 hours, 24 hours, 1 day, 2 days, 3 days, 4 days, 5 days, 6 days, 1 week, 2 weeks, 3 weeks, 1 month, 2 months, 3 months, 6 months, 1 year, 2 years, 3 years, 4 years, or 5 years) after the first time point. In some embodiments, the first time point can be the time of admittance into a medical facility or within 1 week of the first presentation of at least one symptom of a pancreatic β-cell disorder.

In some embodiments, the methods can further include determining (assaying) a level of soluble MANF in a biological sample from the subject at one or more additional, later time points. In these methods, an elevated level of soluble MANF in a later sample (collected later in chronological time) compared to the level of soluble MANF in an earlier (e.g., immediately prior) sample (collected earlier in chronological time) indicates a decrease (e.g., a significant, observable, or detectable decrease) in pancreatic β-cell function or a decrease in pancreatic β-cell mass in the subject. Likewise, a decrease or no significant change in the level of soluble MANF in a later sample (collected later in chronological time) compared to the level of soluble MANF in an earlier (e.g., immediately prior) sample (collected earlier in chronological time) indicates no change or an increase in pancreatic β-cell function or pancreatic β-cell mass in the subject. In some embodiments, these methods are performed on a subject that has a detectable or observable pancreatic β-cell mass and/or has detectable or observable amount pancreatic β-cell function at the first, the second, and the one or more additional time points (e.g., a subject that does not have a complete loss of pancreatic β-cell mass or pancreatic β-cell function at the first, the second, and the one or more additional time points).

In some embodiments, the subject can have previously received a pancreatic β-cell transplant, such that these methods monitor, in part, the pancreatic β-cell function and the pancreatic β-cell mass of the pancreatic β-cell transplanted into the subject. In some embodiments, the transplanted pancreatic β-cells are autografted, homografted, or xenografted pancreatic β-cells. In some embodiments, the transplanted pancreatic β-cells are present within a device, or are surrounded by or placed within a biocompatible polymer. In some embodiments, the transplanted pancreatic β-cells are present within a tissue other than the pancreas (e.g., liver tissue). In some embodiments, these methods are performed in a subject within 1 week, 2 weeks, 3 weeks, 1 month, 2 months, 3 months, 4 months, 5 months, 6 months, or 1 year of pancreatic β-cell transplantation. In some embodiments, the first time point is shortly after (e.g., within 1 week or 2 weeks) of the transplantation procedure.

The levels of soluble MANF can be determined using methods known in the art. For example, the levels of soluble MANF can be detected using a number of techniques known in the art that utilize antibodies that specifically bind to soluble MANF (e.g., enzyme-linked immunosorbent assay). In some embodiments, the methods further include obtaining or collecting a sample or at least two samples from a subject (e.g., a biological sample containing a biological fluid, e.g., urine, blood, plasma, serum, or cerebrospinal fluid).

Any of the methods described herein can be performed on patients presenting to a health care facility (e.g., a hospital, clinic, or an assisted care facility). In some embodiments, the methods are performed on a subject as part of a periodic examination by a health care professional. The subjects may present with one or more symptoms of a pancreatic β-cell disorder (e.g., any of the symptoms of a pancreatic β-cell disorder described herein). The subject can also present with no symptoms (an asymptomatic subject) or just one symptom of a pancreatic β-cell disorder. The subject can have a family history of a pancreatic β-cell disorder (e.g., type 2 diabetes). The subject can be an infant, a child, a teenager, an adult, or an elderly person.

These methods can be performed by any health care professional (e.g., a physician, a laboratory technician, a nurse, a physician's assistant, and a nurse's assistant). A subject identified as having a decrease (e.g., a significant, observable, or detectable decrease) in pancreatic β-cell function or a decrease in pancreatic β-cell mass can be administered a treatment for a pancreatic β-cell disorder (e.g., an isolated, purified, or recombinant soluble MANF protein, pioglitazone, GLP-1, or a DPP-4 inhibitor (e.g., sitagliptin, vildagliptin, saxagliptin, linagliptin, dutogliptin, gemigliptin, and alogliptin), or any of the compositions described herein, e.g., an therapeutically effective dose of a soluble MANF protein containing a sequence at least 90% identical to SEQ ID NO: 2 and/or apomorphine). In some embodiments, e.g., wherein the method includes administering apomorpine, the subject does not have erectile dysfunction or Parkinson's disease.

Some embodiments, further include the additional detection or assessment of one or more (e.g., two, three, or four) other markers of pancreatic β-cell dysfunction in the subject (e.g., decreased C-peptide production and secretion, decreased insulin production and secretion, decreased IAPP production and secretion, increased blood glucose levels, increased glycated hemoglobin levels, and the presence of ketones in a biological fluid of the subject (e.g., in the urine)). Methods for detecting one or more additional markers of a pancreatic β-cell dysfunction are known in the art.

Some embodiments further include administering to a subject identified as having an a decrease in pancreatic β-cell function or a decrease in pancreatic β-cell mass a treatment for a pancreatic β-cell disorder (e.g., an isolated, purified, or recombinant soluble MANF protein, pioglitazone, GLP-1, or a DPP-4 inhibitor (e.g., sitagliptin, vildagliptin, saxagliptin, linagliptin, dutogliptin, gemigliptin, and alogliptin), or any of the compositions described herein, e.g., an therapeutically effective dose of a soluble MANF protein containing a sequence at least 90% identical to SEQ ID NO: 2 and/or apomorphine). Some embodiments include selecting the subject identified as having a decrease in pancreatic β-cell function or a decrease in pancreatic β-cell mass for periodic glucose monitoring (e.g., periodic self-glucose monitoring using a glucometer). Some embodiments further include selecting a subject identified as having a decrease in pancreatic β-cell function or a decrease in pancreatic β-cell mass for periodic medical evaluation by a physician or a health professional (e.g., periodic visits of at least once every year, at least once every six months, at least once every three months, at least once every two months, at least once a month, or at least once a week). Some embodiments further include recording the results of the test in the subject's medical records, or performing a similar test or any art-known test to monitor pancreatic β-cell function or pancreatic β-cell mass in one or more lineal family members of a subject identified as having a decrease in pancreatic β-cell function or a decrease in pancreatic β-cell mass. Some embodiments further include selecting a subject having a decrease in pancreatic β-cell function or a decrease in pancreatic β-cell mass for pancreatic β-cell transplantation.

Methods of Monitoring Efficacy of Treatment of a Pancreatic β-Cell Disorder

Also provided are methods of monitoring the efficacy of treatment of a pancreatic β-cell dysfunction in a subject (e.g., a subject diagnosed as having a pancreatic β-cell disorder). These methods include determining (assaying) a level of soluble MANF in a biological sample from the subject at a first time point, determining (assaying) a level of soluble MANF in a biological sample from the subject at a second time point, and comparing the level of soluble MANF in the biological sample at the second time point to the level of soluble MANF in the biological sample at the first time point, where (i) the first time point is prior to treatment and the second time point is any time point following the initiation of treatment, or (ii) the first time point is following the initiation of treatment and the second time point is at a later time point during or after treatment; and a decreased level of soluble MANF in the biological sample at the second time point compared to the level of soluble MANF in the biological sample at the first time point indicates that the treatment was effective in the subject. In some embodiments, the treatment of a pancreatic β-cell disorder is the administration of one or more of an insulin (e.g., any of the forms of insulin described herein), pioglitazone, and TUDCA. In some embodiments, the treatment is transplantation of pancreatic β-cells into the subject (e.g., as described herein).

A decreased level of soluble MANF in the biological sample at the second time point compared to the level of soluble MANF at the first time point indicates efficacy of the treatment in the subject. An increased level or no substantial change in the level of soluble MANF in the biological sample at the second time point compared to the level of soluble MANF at the first time point indicates that the treatment was not effective and/or that the present treatment should be terminated and/or an alternate therapy should be administered to the subject. In some embodiments, an increased level or no substantial change in the level of soluble MANF in the biological sample at the second time point compared to the level of soluble MANF at the first time point indicates that an increased dosage of the treatment should be administered to the subject or the treatment should be administered at an increased frequency and/or duration In some embodiments, the methods are performed on a subject that has a detectable or observable pancreatic β-cell mass and/or has detectable or observable amount pancreatic β-cell function at the first and the second time point (e.g., a subject that does not have a complete loss of pancreatic β-cell mass or pancreatic β-cell function at the first and the second time point). In some embodiments, the methods are performed on a subject that has been previously identified or diagnosed as having a pancreatic β-cell disorder. Some embodiments further include selecting a subject that has a pancreatic β-cell disorder. Some embodiments further include obtaining a sample from the subject. Some embodiments further include administering one or more doses of a treatment to the subject.

In some embodiments, the second time point can be at least 6 hours (e.g., at least 12 hours, 18 hours, 24 hours, 1 day, 2 days, 3 days, 4 days, 5 days, 6 days, 1 week, 2 weeks, 3 weeks, 1 month, 2 months, 3 months, 6 months, 1 year, 2 years, 3 years, 4 years, or 5 years) after the first time point. In some embodiments, the first time point can be the time of admittance into a medical facility or within 1 week of the first presentation of at least one symptom of a pancreatic β-cell disorder.

In some embodiments, the methods can further include determining (assaying) a level of soluble MANF in a biological sample from the subject at one or more additional, later time points. In these methods, a decreased level of soluble MANF in a later sample (collected later in chronological time) compared to the level of soluble MANF in an earlier (e.g., immediately prior) sample (collected earlier in chronological time) indicates efficacy of treatment in the subject. Likewise, an increase or no significant change in the level of soluble MANF in a later sample (collected later in chronological time) compared to the level of soluble MANF in an earlier (e.g., immediately prior) sample (collected earlier in chronological time) indicates that the treatment was not effective in the subject. In some embodiments, these methods are performed on a subject that has a detectable or observable pancreatic β-cell mass and/or has detectable or observable amount pancreatic β-cell function at the first, the second, and the one or more additional time points (e.g., a subject that does not have a complete loss of pancreatic β-cell mass or pancreatic β-cell function at the first, the second, and the one or more additional time points).

In some embodiments, the subject can have previously received a pancreatic β-cell transplant, such that these methods monitor, in part, the efficacy of the pancreatic β-cell transplantation in the subject. In some embodiments, the transplanted pancreatic β-cells are autografted, homografted, or xenografted pancreatic β-cells. In some embodiments, the transplanted pancreatic β-cells are present within a device, or are surrounded by or placed within a biocompatible polymer. In some embodiments, the transplanted pancreatic β-cells are present within a tissue other than the pancreas (e.g., liver tissue). In some embodiments, these methods are performed in a subject within 1 week, 2 weeks, 3 weeks, 1 month, 2 months, 3 months, 4 months, 5 months, 6 months, or 1 year of pancreatic β-cell transplantation. In some embodiments, the first time point is shortly after (e.g., within 1 week or 2 weeks) of the transplantation procedure.

The levels of soluble MANF can be determined using methods known in the art. For example, the levels of soluble MANF can be detected using a number of techniques known in the art that utilize antibodies that specifically bind to soluble MANF (e.g., enzyme-linked immunosorbent assay). In some embodiments, the methods further include obtaining or collecting a sample or at least two samples from a subject (e.g., a biological sample containing a biological fluid, e.g., urine, blood, plasma, serum, or cerebrospinal fluid). Any of the methods described herein can be performed on patients presenting to a health care facility (e.g., a hospital, clinic, or an assisted care facility). In some embodiments, the methods are performed on a subject as part of a periodic examination by a health care professional. The subjects may be previously diagnosed with a pancreatic β-cell disorder and/or may present with one or more symptoms of a pancreatic β-cell disorder (e.g., any of the symptoms of a pancreatic β-cell disorder described herein). The subject can be an infant, a child, a teenager, an adult, or an elderly person.

These methods can be performed by any health care professional (e.g., a physician, a laboratory technician, a nurse, a physician's assistant, and a nurse's assistant). Some embodiments, further include the additional detection or assessment of one or more (e.g., two, three, or four) other markers of a pancreatic β-cell disorder in the subject (e.g., where increased C-peptide production and secretion, increased insulin production and secretion, increased IAPP production and secretion, decreased blood glucose levels, decreased glycated hemoglobin levels, and the absence or no significant level of ketones in a biological fluid of the subject (e.g., in the urine) at the second time point as compared to the corresponding levels at the first time point further indicate that the treatment is effective). Methods for detecting one or more additional markers of a pancreatic β-cell disorder are known in the art.

Methods of Selecting a Subject for Treatment

Also provided are methods of selecting a subject for treatment of a pancreatic β-cell disorder. These methods include determining (assaying) a level of soluble MANF in a biological sample from the subject; comparing the level of soluble MANF in the biological sample to a reference level of soluble MANF; and selecting a subject having an elevated level of soluble MANF in the biological sample compared to the reference level for treatment of a pancreatic β-cell disorder. In these methods, subjects having a decrease or no significant change in the level of soluble MANF in the biological sample compared to the reference level are not selected for treatment of a pancreatic β-cell disorder.

Some embodiments can further include assessing or determining the level of one or more additional markers of a pancreatic β-cell disorder, wherein the detection of one or more additional markers of a pancreatic β-cell disorder further indicates that the subject should be selected for treatment of a pancreatic β-cell disorder. These one or more additional markers of a pancreatic β-cell disorder include a decrease in the level of C-peptide in a biological sample from the subject, a decrease in the level of IAPP in a biological sample from the subject, a decrease in the level of insulin in a biological sample from the subject, an increase one or more blood glucose level(s) in the subject, an increase in the glycated hemoglobin level in the subject, or the detection of ketones in a biological sample from the subject (e.g., in the urine). Methods for detecting the levels of C-peptide, IAPP, insulin, blood glucose, glycated hemoglobin, and ketones in a biological sample from the subject are known in the art.

The levels of soluble MANF can be determined using methods known in the art. For example, the levels of soluble MANF can be detected using a number of techniques known in the art that utilize antibodies that specifically bind to soluble MANF (e.g., enzyme-linked immunosorbent assay). In some embodiments, the methods further include obtaining or collecting a sample from a subject (e.g., a biological sample containing a biological fluid, e.g., urine, blood, plasma, serum, or cerebrospinal fluid). The methods can be performed by any health care professional (e.g., a physician, a nurse, a physician's assistant, a laboratory technician, or a nurse's assistant).

The subjects may present with one or more symptoms of a pancreatic β-cell disorder (e.g., any of the symptoms of a pancreatic β-cell disorder described herein). The subject can also present with no symptoms or just one symptom of a pancreatic β-cell disorder. The subject can be suspected of having a pancreatic β-cell disorder or the subject can have an increased risk of developing a pancreatic β-cell disorder. The subject can have a family history of a pancreatic β-cell disorder (e.g., type 2 diabetes). The subject can be previously diagnosed as having a pancreatic β-cell disorder.

In some embodiments, the methods are performed on a subject that has a detectable or observable pancreatic β-cell mass and/or has detectable or observable amount pancreatic β-cell function (e.g., a subject that does not have a complete loss of pancreatic β-cell mass or pancreatic β-cell function).

Treatments of a pancreatic β-cell disorder that can be administered to the subject include, without limitation: a soluble MANF (e.g., a soluble MANF protein that contains a sequence at least 80% identical to SEQ ID NO: 2, i.e., to the full length of SEQ ID NO:2), apomorphine, rapid-acting insulin (e.g., aspart or lispro insulin), short-acting (e.g., regular insulin), intermediate-acting insulin (e.g., neutral protamine Hagedorn or NPH insulin), long-acting insulin (e.g., ultralente insulin), insulin glargine, insulin detemir, pramlintide, incretin mimetics (e.g., exenatide), sulfonylureas (e.g., chorpropamide, glipizide, glyburide, and glimepiride), meglitinides (e.g., repaglinide and nateglinide), biguanides (e.g., metformin), thiazolidinediones (e.g., rosiglitazone and pioglitazone), alpha-glucosidase inhibitors (e.g., acarbose and meglitol), and DPP-4 inhibitors (e.g., sitagliptin and saxagliptin). Treatments of a pancreatic β-cell disorder can include one or more (e.g., two, three, or four) of the above agents used in any combination. In some embodiments, e.g., wherein the method includes administering apomorpine, the subject does not have erectile dysfunction or Parkinson's disease.

Some embodiments of these methods further include administering to the subject at least one (e.g., at two, three, or four) treatment for a pancreatic β-cell disorder (e.g., one or more of the treatments of a pancreatic β-cell disorder described herein or known in the art). For example, some embodiments of these methods further include administering at least one (e.g., at least two, four, six, eight, or ten) dose of any of the pharmaceutical compositions described herein. The treatment of a pancreatic β-cell disorder can continue over a period of time of at least 1 week, 1 month, 6 months, 1 year, 2 years, 3 years, 4 years, 5 years, or 10 years. The treatment can be administered periodically to the subject (e.g., once a day, twice a day, three times a day, four times a day, once a week, twice a week, three times a week, four times a week, once a month, twice a month, three times a month, or four times a month).

In some embodiments, a subject having an elevated level of soluble MANF as compared to the reference level is selected for periodic medical evaluation by a physician or a health professional (e.g., periodic visits of at least once every year, at least once every six months, at least once every three months, at least once every two months, at least once a month, or at least once a week). Some embodiments further include recording in a subject's medical records that the subject should be administered or prescribed one or more treatment of a pancreatic β-cell disorder (e.g., any of the exemplary treatments described herein). In some embodiments, a subject having an elevated level of soluble MANF as compared to the reference level is selected for pancreatic β-cell transplantation.

Methods of Identifying a Subject at Risk of Developing a Pancreatic β-Cell Disorder Also provided are methods of identifying a subject at risk of developing a pancreatic β-cell disorder. These methods include determining a level of soluble MANF in a biological sample from a subject; comparing the level of the soluble MANF in the biological sample from the subject to a reference level of soluble MANF. A subject is identified as having an increased risk of developing a pancreatic β-cell disorder if the level of soluble MANF in the biological sample from the subject is elevated compared to the reference level. A subject is identified as having a decreased risk of developing a pancreatic β-cell disorder if the level of soluble MANF in the biological sample from the subject is decreased or not significantly changed compared to the reference level.

In any of the methods described herein, the increased risk is relative to a subject that does not have a significant or observable elevation in the level of soluble MANF (e.g., a subject that is not diagnosed as having a pancreatic β-cell disorder using any of the methods described herein, a healthy subject is not diagnosed as having a disease, or a subject that does not have a symptom of a pancreatic β-cell disorder or a family history of a pancreatic β-cell disorder).

The levels of soluble MANF may be determined using standard methods (e.g., any of the antibody-based methods known in the art). The methods can be performed by any health care professional (e.g., a physician, a nurse, a physician's assistant, a laboratory technician, or a nurse's assistant).

The subjects may present with one or more symptoms of a pancreatic β-cell disorder (e.g., any of the symptoms of a pancreatic β-cell disorder described herein). The subject can also be suspected of having a pancreatic β-cell disorder. The subject can also present with no symptoms or just one symptom of a pancreatic β-cell disorder. The subject can have a family history of a pancreatic β-cell disorder (e.g., type 2 diabetes).

In some embodiments, the methods are performed on a subject that has a detectable or observable pancreatic β-cell mass and/or has detectable or observable amount pancreatic β-cell function (e.g., a subject that does not have a complete loss of pancreatic β-cell mass or pancreatic β-cell function).

Subjects identified as having an increased risk of developing a pancreatic β-cell disorder may be administered a treatment for a pancreatic β-cell disorder (e.g., any of the treatments described herein) or may be administered a new or alternative treatment for a pancreatic β-cell disorder. Subjects identified as having an increased risk of developing a pancreatic β-cell disorder can also undergo more aggressive therapeutic treatment (e.g., increased periodicity of clinic or hospital visits).

Some embodiments further include administering to a subject identified as having an increased risk of developing a pancreatic β-cell disorder a treatment for a pancreatic β-cell disorder (e.g., an isolated, purified, or recombinant soluble MANF protein, pioglitazone, GLP-1, or a DPP-4 inhibitor (e.g., sitagliptin, vildagliptin, saxagliptin, linagliptin, dutogliptin, gemigliptin, and alogliptin), or any of the compositions described herein, e.g., an therapeutically effective dose of a soluble MANF protein containing a sequence at least 90% identical to SEQ ID NO: 2 and/or apomorphine). Some embodiments include selecting the subject having an increased risk of developing a pancreatic β-cell disorder for glucose monitoring (e.g., self-glucose monitoring using a glucometer). Some embodiments further include selecting the subject for periodic medical evaluation by a physician or a health professional (e.g., periodic visits of at least once every year, at least once every six months, at least once every three months, at least once every two months, or at least once a month). Some embodiments further include recording the results of the test in the subject's medical records, or performing a similar test or any art-known test to determine the risk of developing a pancreatic β-cell disorder in one or more lineal family members of a subject identified as having an increased risk of developing a pancreatic β-cell disorder using the methods described herein.

Methods of Selecting a Subject for Participation in a Clinical Study

Also provided are methods for selecting a subject for participation in a clinical study. These methods include determining a level of soluble MANF in a biological sample from the subject; comparing the level of soluble MANF in the biological sample from the subject to a reference level of soluble MANF, and selecting a subject having an elevation, or a decrease or no significant change in the level of soluble MANF in the biological sample compared to the reference level (e.g., any of the reference levels of soluble MANF described herein) for participation in a clinical study.

The levels of soluble MANF may be determined using standard molecular biology methods (e.g., any of the antibody-based methods described herein). The methods can be performed by any health care professional (e.g., a physician, a nurse, a physician's assistant, a laboratory technician, or a nurse's assistant).

In some embodiments, the subject may present with one or more symptoms of a pancreatic β-cell disorder (e.g., any of the symptoms of a pancreatic β-cell disorder described herein). In some embodiments, the subject can also present with no symptoms or just one symptom of a pancreatic β-cell disorder. In some embodiments, the subject can have a family history of a pancreatic β-cell disorder (e.g., type 2 diabetes). In some embodiments, the subject can already be diagnosed as having a pancreatic β-cell disorder. In some embodiments, the subject is taking a treatment for a pancreatic β-cell disorder. In some embodiments, the subject is administered a new or alternative treatment for a pancreatic β-cell disorder during the clinical study.

Methods of Detecting Endoplasmic Reticulum Stress in a Pancreatic β-Cell

Also provided are methods of detecting endoplasmic reticulum stress in a pancreatic β-cell that include determining a level of soluble MANF produced by a pancreatic β-cell, and comparing the level of soluble MANF produced to a reference level (e.g., any of the reference levels of soluble MANF described herein) of soluble MANF. An elevated level of soluble MANF produced by the pancreatic β-cell compared to the reference level of soluble MANF indicates an increase in endoplasmic reticulum stress in the pancreatic β-cell. A decrease or no significant change in the level of soluble MANF produced by the pancreatic β-cell compared to the reference level of soluble MANF indicates that the pancreatic β-cell has not experienced a detectable level of endoplasmic reticulum stress.

The levels of soluble MANF may be determined using standard molecular biology methods (e.g., any of the antibody-based methods described herein). The methods can be performed by any health care professional (e.g., a physician, a nurse, a physician's assistant, a laboratory technician, or a nurse's assistant) or a scientist.

In some embodiments, the pancreatic β-cell is in a mammal (e.g., a human) and the levels of soluble MANF produced by the pancreatic β-cell can be determined from a biological sample from the mammal (e.g., a sample containing blood, serum, or plasma). In some embodiments, the pancreatic β-cell can be an endogenous pancreatic β-cell or a transplanted pancreatic β-cell (e.g., an autografted, homografted, or xenografted pancreatic β-cell). In some embodiments, the pancreatic β-cell is an autografted pancreatic β-cell that has been genetically modified). In some embodiments, the pancreatic β-cells can be present within a pancreas of the mammal or can be present in a tissue other than the pancreas (e.g., the liver). In some embodiments, the pancreatic β-cells can be present in a device, or a biocompatible material or polymer.

In some embodiments, the pancreatic β-cell is present in vitro (e.g., in a tissue culture). For example, a primary pancreatic β-cell harvested from a mammal can be cultured ex vivo. In some embodiments, the cultured pancreatic β-cell is a primary mammalian (e.g., human, rat, monkey, cow, or pig) pancreatic β-cell line. In some embodiments, the cultured mammalian pancreatic β-cell can be genetically manipulated (e.g., genetically modified to express one or more proteins or genetically modified to decrease the expression of one or more proteins) or chemically treated (e.g., with one or more growth factors). In some embodiments, the pancreatic β-cell can be cultured in the presence of one or more biocompatible polymers or biosynthetic materials (e.g., polymers or materials that aid in the transplantation of the pancreatic β-cells into a mammal (e.g., a human)). A variety of biocompatible polymers and biosynthetic materials are known in the art.

In some embodiments, the detection of endoplasmic reticulum stress in pancreatic β-cells within a subject is followed by one or more of the following: identification of a subject having an increased level of endoplasmic reticulum stress in his or her pancreatic β-cells, administration of a therapeutic agent (e.g., an agent that will decrease endoplasmic reticulum stress in pancreatic β-cells, e.g., any of the soluble MANF proteins described herein and/or apomorphine); monitoring of pancreatic β-cell function (e.g., any of the methods of monitoring pancreatic β-cell function described herein) in the subject; and increasing the frequency of clinical visits or the level of health monitoring (e.g., increased frequency of blood glucose testing) of the subject. In some embodiments, e.g., wherein the method includes administering apomorphine, the subject does not have erectile dysfunction or Parkinson's disease.

In some embodiments, the detection of increased endoplasmic reticulum stress in pancreatic β-cells in vitro is followed by contacting the pancreatic β-cell with a therapeutic agent (e.g., an agent that will decrease endoplasmic reticulum stress in pancreatic β-cells, e.g., any of the soluble MANF proteins described herein or apomorphine) and/or monitoring of pancreatic β-cell function (e.g., any of the methods of monitoring pancreatic β-cell function described herein). In any of the methods described herein, the pancreatic β-cell can be cultured in vitro with at least one other cell type or at least one other cell line (e.g., co-culture or feeder culture).

Methods of Treatment

Also provided are methods of treating or delaying the onset of a pancreatic β-cell disorder in a subject that include administering to a subject an effective amount of a soluble MANF (e.g., a purified, isolated, or recombinant soluble MANF protein (e.g., any of the soluble MANF proteins described herein)) and/or apomorphine. In some embodiments, treating can result in a decrease in the number of symptoms of a pancreatic β-cell disorder (e.g., any of the symptoms described herein) in a subject or a decrease in the severity, intensity, or frequency of one or more symptoms of a pancreatic β-cell disorder (e.g., any of the symptoms described herein). In some embodiments, treating can result in a delay in the onset or one or more symptoms (an increase in the time of actual onset of one or more symptoms in a subject not receiving treatment compared to a subject receiving treatment). For example, treating can result in one or more of the following: a decrease in the blood glucose level(s) in a subject, a decrease in the level of glycated hemoglobin in a subject, a decrease in the rate of loss of the production of insulin in a subject, a decrease in the rate of loss of pancreatic β-cell function in a subject, and a decrease in the rate of loss of pancreatic β-cell mass in a subject. In some embodiments, e.g., wherein the method includes administering apomorphine, the subject does not have erectile dysfunction or Parkinson's disease.

Soluble MANF

For example, in some embodiments that soluble MANF administered to a subject contains a sequence that is at least 80% identical (e.g., at least 85%, 90%, 91%, 92%, 93%, 94%, 95%, 96%, 97%, 98%, 99%, or 100% identical) to any one of SEQ ID NOS: 2 and 4-7, i.e., to the full length of SEQ ID NOs:2 or 4-7, and optionally, has a biological activity of a soluble MANF protein (described herein). In some embodiments, the soluble MANF administered to a subject contains a sequence that is at least 95% identical (e.g., at least 96%, 97%, 98%, 99%, or 100% identical) to SEQ ID NO: 2 (human soluble MANF), i.e., to the full length of SEQ ID NO:2, and optionally, has a biological activity of soluble MANF (described herein). In some embodiments, the soluble MANF administered to a subject is SEQ ID NO: 2 or an endogenous (wildtype) form of soluble MANF. In any of these embodiments, the soluble MANF can be purified or isolated. In any of these embodiments, the soluble MANF can be a recombinant protein.

The comparison of sequences and determination of percent identity between two sequences is accomplished using a mathematical algorithm. The percent identity between two amino acid sequences is determined using the Needleman and Wunsch, J. Mol. Biol., 48:444-453, 1970) algorithm, which has been incorporated into the GAP program in the GCG software package (available on the Internet at gcg.com), using either a Blossum 62 matrix or a PAM250 matrix, and a gap weight of 16 and a length weight of 1. The percent identity between two nucleotide sequences is determined using the GAP program in the GCG software package (also available on the Internet at gcg.com), using a NWSgapdna.CMP matrix, a gap weight of 40, and a length weight of 1.

In general, percent identity between amino acid sequences referred to herein is determined using the BLAST 2.0 program, which is available to the public at the National Center for Biotechnology Information (NCBI) website. Sequence comparison is performed using an ungapped alignment and using the default parameters (Blossum 62 matrix, gap existence cost of 11, per residue gap cost of 1, and a lambda ratio of 0.85). The mathematical algorithm used in BLAST programs is described in Altschul et al., Nucleic Acids Research 25:3389-3402, 1997.

As noted herein, mammalian forms of soluble MANF have a high degree of sequence identity. One skilled in the art would recognize that, generally speaking, in order to obtain variants of soluble MANF that have biological activity (e.g., the ability to treat or delay the onset of a pancreatic β-cell disorder in a subject, reduce endoplasmic reticulum stress in a pancreatic β-cell, or reduce or delay endoplasmic reticulum stress-induced apoptotic cell death in population of two or more pancreatic β-cells), residues that are not conserved between various mammalian species of soluble MANF could be altered or removed, while those residues that are highly conserved should not be altered or removed. As is known in the art, one skilled in the art can align the various sequences for mammalian soluble MANF proteins provided herein to identify those residues that are highly conserved and those residues that are not conserved.

The biological activity of the various forms of soluble MANF can be tested by performing various biological activity assays described herein or those known in the art. For example, the biological activity of a soluble MANF protein can be tested by treating a pancreatic β-cell cultured in the presence or absence of a soluble MANF (e.g., any of the soluble MANF proteins described herein) and challenging the pancreatic β-cells with an agent that induces endoplasmic reticulum stress in the pancreatic β-cells. A soluble MANF having biological activity will reduce the amount of endoplasmic reticulum stress or endoplasmic reticulum stress-induced apoptosis observed in the cells contacted with the soluble MANF and the agent, as compared to the cells not contacted with the soluble MANF and treated with the agent. For example, a soluble MANF having biological activity can reduce one or more markers of endoplasmic reticulum stress in a cell treated with an agent that induces endoplasmic reticulum stress compared to a cell not treated with a soluble MANF and treated with the agent (e.g., reduce the induction of glucose-regulated protein-78 (also known as grp78 or BiP) or bcl-2-associated athanogene-1 (bag-1) expression; reduce activation, Golgi translocation, protease cleavage, or nuclear translocation of activating transcription factor 6 (ATF6); reduce protein kinase RNA-like endoplasmic reticulum kinase (PERK) activation, oligomerization, or autophosphorylation; reduce activation of IRE1; decrease phosphorylation of eIF2α; reduce the intron processing of XBP1 mRNA; reduce activation of a JNK signaling pathway; prevent activation and cleavage of pro-caspase 4; and prevent or decrease the shift in the endoplasmic reticulum redox environment (e.g., measured using the redox sensitive eroGFP protein as described in the Examples)).

A soluble MANF administered to the subject can also contain one or more (e.g., 2, 3, 4, 5, 6, 7, 8, 9, 10, 11, 12, 13, 14, or 15) insertions, additions, deletions, or modifications. For example, a soluble MANF can be covalently attached to a chemical moiety (e.g., a protein (e.g., albumin), a sugar (e.g., N-linked glycans or O-linked glycans, e.g., mannose) (see, e.g., Sola et al., J. Pharm. Sci. 98:1123-1245, 2009), or a polymer (e.g., polyethylene glycol)) that significantly increases the half-life of the soluble MANF in a subject or increases the thermal stability of the soluble MANF (e.g., during storage). The soluble MANF protein used in these methods can also include an HIV tat protein or any other moiety that increases the cellular permeability of the soluble MANF protein.

Several methods are known in the art for the production of a recombinant protein (e.g., a recombinant soluble MANF) using molecular biology and cell culture techniques. For example, a soluble MANF encoded by a mRNA sequence (e.g., an mRNA containing a sequence at least 80% identical (e.g., at least 85%, 90%, 91%, 92%, 93%, 94%, 95%, 96%, 97%, 98%, 99%, or 100% identical) to SEQ ID NO: 3 can be transfected into a bacterial, yeast, or mammalian cell (using a protein expression plasmid or viral vector) that allows for the expression of the soluble MANF by the transfected cell. The transfected cells or the culture medium can be collected, and the recombinant soluble MANF protein purified using methods known in the art. A number of additional nucleic acids (mRNA) encoding other mammalian soluble MANF proteins are known in the art.

In some embodiments, the subject is first identified or selected for treatment using any of the diagnostic methods described herein or any of the methods of predicting a subject at risk of developing a pancreatic β-cell disorder described herein or known in the art.

A subject can be administered at least one (e.g., at least 2, 3, 4, or 5) dose of a soluble MANF (e.g., any of the soluble MANF proteins described herein) and/or apomorphine. The soluble MANF and/or apomorphine can be administered to the subject at least once a day (e.g., twice a day, three times a day, and four times a day), at least once a week (e.g., twice a week, three times a week, four times a week), and/or at least once a month. A subject can be treated (e.g., periodically administered a soluble MANF) for a prolonged period of time (e.g., at least one month, two months, six months, one year, two years, three years, four years, or five years). As described in detail herein, the dosage of the soluble MANF and/or apomorphine to be administered to the subject can be determined by a physician by consideration of a number of physiological factors including, but not limited to, the sex of the subject, the weight of the subject, the age of the subject, and the presence of other medical conditions. The soluble MANF and/or apomorphine can be administered to the subject orally, intravenously, intraarterially, subcutaneously, intramuscularly, intracranially, or via injection into the cerebrospinal fluid. Likewise, the agent may be formulated as a solid (e.g., for oral administration) or a physiologically acceptable liquid carrier (e.g., saline) (e.g., for intravenous, intraarterial, subcutaneous, intramuscular, or cerebrospinal administration).

In some embodiments, the subject is further administered at least one (e.g., two, three, four, or five) other treatment of a pancreatic β-cell disorder (e.g., any of the treatments for a pancreatic β-cell disorder described herein, e.g., any of the insulins described herein). In some embodiments, the soluble MANF and/or apomorphine is formulated together with at least one (e.g., two, three, or four) other treatment of a pancreatic β-cell disorder (e.g., formulated in a physiologically acceptable buffer or medium for systemic administration) (e.g., any of the pharmaceutical compositions described herein).

Methods of Reducing Endoplasmic Reticulum Stress in a Pancreatic β-Cell

Also provided are methods of reducing endoplasmic reticulum stress in a pancreatic β-cell. These methods include contacting the pancreatic β-cell with an effective amount of one or more (e.g., two or three) of soluble MANF (e.g., any of the soluble MANF proteins described herein, e.g., a recombinant, purified, or isolated soluble MANF protein containing a sequence at least 80% identical to SEQ ID NO: 2), apomorphine, and pioglitazone. In some embodiments, the pancreatic β-cell is in vitro (tissue culture). In some embodiments, the pancreatic β-cell can be in a subject. The pancreatic β-cell used in these experiments can be any pancreatic β-cell described herein.

In some embodiments, the pancreatic β-cell can be contacted with one or more (e.g., two or three) of a soluble MANF, apomorphine, and pioglitazone for an extended period of time (e.g., at least 15 minutes, 30 minutes, 1 hour, 2 hours, 6 hours, 8 hours, 10 hours, 12 hours, or 24 hours). In some embodiments, the pancreatic β-cell is contacted with several doses of one or more (e.g., two or three) of a soluble MANF, apomorphine, and pioglitazone (e.g., at least two doses, three doses, four doses, or five doses), e.g., at regular, timed intervals (e.g., approximately once a day, once a week, or once a month).

A reduction in endoplasmic reticulum stress can be determined using any methods known in the art for detecting endoplasmic reticulum stress in a cell (e.g., detecting or assessing any of the markers of endoplasmic reticulum stress described herein). For example, a reduction in endoplasmic reticulum stress can be detected by a reduction in one or more markers of endoplasmic reticulum stress in a cell. In some embodiments, a reduction in endoplasmic reticulum stress can be observed by one or more of the following events: a reduction in the induction of grp78 (BiP) or bag-1 expression; a reduction in the activation, Golgi translocation, protease cleavage, or nuclear translocation of ATF6; a reduction in PERK activation, oligomerization, or autophosphorylation; a reduction in the activation of IRE1; a reduction in phosphorylation of eIF2α; a reduction in the intron processing of XBP1 mRNA; a reduction in the activation of a JNK signaling pathway; a reduction in the activation and cleavage of procaspase 4; and a reduction in the shift in the redox environment of the endoplasmic reticulum induced by exposure to a ER-stress inducing agent (e.g., as compared to a control pancreatic β-cell exposed to a ER-stress inducing agent, but not treated with one or more (e.g., two or three) of soluble MANF, apomorphine, and pioglitazone). A reduction in the shift in the redox environment of the endoplasmic reticulum can be measured using redox-sensitive dyes or proteins, e.g., the reporter protein described in the Examples. In some embodiments, the reduction in endoplasmic reticulum stress in a pancreatic β-cell can be compared to the amount of endoplasmic reticulum stress observed or detected in a pancreatic β-cell not contacted with one or more of soluble MANF, apomorphine, and pioglitazone, respectively (e.g., in vitro or in a subject). In some embodiments, the reduction in endoplasmic reticulum stress in a pancreatic β-cell is relative to a control pancreatic β-cell that is not contacted with a soluble MANF protein, apomorphine, or pioglitazone, but is contacted with an agent that induces endoplasmic reticulum stress (e.g., thapsigargin).

These methods can be performed by a health care professional (e.g., any health care professional described herein) or a scientist.

Methods of Reducing or Delaying Endoplasmic Reticulum Stress-Induced Apoptosis

Pancreatic β-cells having endoplasmic reticulum stress can activate apoptotic pathways within the cell. Also provided herein are methods of reducing or delaying endoplasmic reticulum stress-induced apoptosis in a population of two or more pancreatic β-cells that include contacting the population of pancreatic β-cells with an effective amount of one or more (e.g., two or three) of a soluble MANF (e.g., any of the soluble MANF proteins described herein), apomorphine, and pioglitazone.

In some embodiments, the pancreatic β-cell is in vitro (tissue culture). In some embodiments, the pancreatic β-cell can be in a subject (e.g., in an engrafted biocompatible material or polymer). The pancreatic β-cells used in these methods can be any pancreatic β-cells described herein. In some embodiments, the pancreatic β-cell can be contacted with one or more (e.g., two or three) of a soluble MANF, apomorphine, and pioglitazone for an extended period of time (e.g., at least 15 minutes, 30 minutes, 1 hour, 2 hours, 6 hours, 8 hours, 10 hours, 12 hours, or 24 hours). In some embodiments, the pancreatic β-cell is contacted with several doses of one or more (e.g., two or three) of a soluble MANF, pioglitazone, and apomorphine (e.g., at least two doses, three doses, four doses, or five doses), e.g., at regular timed intervals.

The onset and timing of apoptosis in a pancreatic β-cell population can be determined using any of the methods described herein or those known in the art. Contacting a pancreatic β-cell population with one or more (e.g., two or three) of a soluble MANF, apomorphine, and pioglitazone can mediate a decrease in the percentage of pancreatic β-cells within the population that undergo apoptosis (e.g., endoplasmic reticulum stress-induced apoptosis) or delay the onset of apoptosis within the population of pancreatic β-cells. In some embodiments, the decrease or delay in endoplasmic reticulum stress-induced apoptosis in cells treated with one or more (e.g., two or three) of a soluble MANF, apomorphine, and pioglitazone can be compared to a population of pancreatic β-cells that are not treated with one or more (e.g., two or three) of a soluble MANF, apomorphine, and pioglitazone. In some embodiments, the decrease or delay in endoplasmic reticulum stress-induced apoptosis in cells treated with one or more (e.g., two or three) of a soluble MANF, apomorphine, and pioglitazone can be compared to a control population of pancreatic β-cells not treated with one or more (e.g., two or three) of a soluble MANF, apomorphine, and pioglitazone, but contacted with an agent that induces endoplasmic reticulum stress (e.g., thapsigargin).

Methods for detecting apoptotic cell death are well-known in the art and include, without limitation, the cleavage of cellular caspases (e.g., procaspase-3 and procaspase-4), Hoescht and 7-amino-actinomycin uptake, TdT-mediated dUTP nick end labeling assay, and annexin membrane staining A variety of kits for detecting apoptotic cell death are commercially available.

Pharmaceutical Compositions

Also provided herein are pharmaceutical compositions that contain at least one soluble MANF (e.g., any of the soluble MANF proteins described herein, e.g., a purified, isolated, or recombinant soluble MANF) and/or apomorphine, and at least one other treatment for a pancreatic β-cell disorder (e.g., one or more of any of the treatments of a pancreatic β-cell disorder described herein, e.g., pioglitazone, TUDCA, and any of the insulins described herein).

In some embodiments, the compositions are formulated with a pharmaceutically acceptable carrier. The pharmaceutical compositions and formulations can be administered parenterally, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The pharmaceutical compositions provided herein may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring, and perfuming agents, preservatives, and antioxidants can also be present in the compositions.

Formulations of the compositions of the invention include those suitable for intradermal, inhalation, oral/nasal, topical, and/or parenteral administration. The formulations may conveniently be presented in unit dosage form and may be prepared by any methods well known in the art of pharmacy. The amount of active ingredient (e.g., soluble MANF and/or apomorphine, and one or more additional therapeutic agents of a pancreatic β-cell disorder) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect (e.g., one or more of any of the therapeutic effects described herein).

Pharmaceutical formulations of this invention can be prepared according to any method known to the art for the manufacture of pharmaceuticals. Such drugs can contain sweetening agents, flavoring agents, coloring agents, and preserving agents. A formulation can be admixed with nontoxic pharmaceutically acceptable excipients which are suitable for manufacture. Formulations may comprise one or more diluents, emulsifiers, preservatives, buffers, excipients, etc., and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders, such as lactose or starches, lubricants, such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a soluble MANF and/or apomorphine, and one or more additional treatments of a pancreatic β-disorder) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth, and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long-chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame, or saccharin. Formulations can be adjusted for osmolarity.

In some embodiments, oil-based pharmaceuticals are used for administration. Oil-based suspensions can be formulated by suspending active agents in a vegetable oil, such as arachis oil, olive oil, sesame oil, or coconut oil, or in a mineral oil, such as liquid paraffin; or a mixture of these. See, e.g., U.S. Pat. No. 5,716,928, describing using essential oils or essential oil components for increasing bioavailability and reducing inter- and intra-individual variability of orally administered hydrophobic pharmaceutical compounds (see also, U.S. Pat. No. 5,858,401). The oil suspensions can contain a thickening agent, such as beeswax, hard paraffin, or cetyl alcohol. Sweetening agents can be added to provide a palatable oral preparation, such as glycerol, sorbitol, or sucrose. These formulations can be preserved by the addition of an antioxidant such as ascorbic acid. As an example of an injectable oil vehicle, see Minto, *J. Pharmacol. Exp. Ther.* 281:93-102, 1997.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally-occurring phosphatides, such as soybean lecithin, esters, or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate, and/or an ethoxylated sorbitan trioleate.

The pharmaceutical compounds can also be administered by in intranasal or intraocular routes including insufflation, powders, and aerosol formulations (for examples of steroid inhalants, see e.g., Rohatagi, *J. Clin. Pharmacol.* 35:1187-1193, 1995; Tjwa, *Ann. Allergy Asthma Immunol.* 75:107-111, 1995).

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao, J. *Biomater Sci. Polym. Ed.* 7:623-645, 1995; as biodegradable and injectable gel formulations, see, e.g., Gao, *Pharm. Res.* 12:857-863, 1995; or, as microspheres for oral administration, see, e.g., Eyles, *J. Pharm. Pharmacol.* 49:669-674, 1997.

In some embodiments, the pharmaceutical compounds can be parenterally administered, such as by intravenous (IV), intramuscular, intraperitoneal, or subcutaneous administration, or administration into a body cavity, a lumen of an organ, or into the cerebrospinal fluid of a subject. These formulations can comprise a solution of active agent dissolved in a pharmaceutically acceptable carrier. Acceptable vehicles and solvents that can be employed are water and Ringer's solution, or an isotonic sodium chloride. In addition, sterile fixed oils can be employed as a solvent or suspending medium. For this purpose any bland fixed oil can be employed including synthetic mono- or diglycerides. In addition, fatty acids, such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate, and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous (e.g., substantially uninterrupted introduction into a blood vessel for a specified period of time).

In some embodiments, the pharmaceutical compounds and formulations can be lyophilized. Stable lyophilized formulations comprising a soluble MANF and/or apomorphine, and one or more additional treatments of a pancreatic β-cell disorder can be made by lyophilizing a solution comprising a soluble MANF and/or apomorphine, and the one or more additional treatments and a bulking agent, e.g., mannitol, trehalose, raffinose, and sucrose, or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5, but less than 6.5. See, e.g., US2004/0028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400 and 6,007,839; Al-Muhammed, *J. Microencapsul.* 13:293-306, 1996; Chonn, *Curr. Opin. Biotechnol.* 6:698-708, 1995; and Ostro, *Am. J. Hosp. Pharm.* 46:1576-1587, 1989.

The formulations of the invention can be administered for prophylactic and/or therapeutic treatments. In some embodiments, for therapeutic applications, compositions are administered to a subject who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to reduce the number of symptoms or reduce the severity, duration, or frequency of one or more symptoms of a pancreatic β-cell disorder in a subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age, and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones, *J. Steroid Biochem. Mol. Biol.* 58:611-617, 1996; Groning, *Pharmazie* 51:337-341, 1996; Fotherby, *Contraception* 54:59-69, 1996; Johnson, *J. Pharm. Sci.* 84:1144-1146, 1995; Rohatagi, *Pharmazie* 50:610-613, 1995; Brophy, *Eur. J. Clin. Pharmacol.* 24:103-108, 1983; *Remington: The Science and Practice of Pharmacy*, 21st ed., 2005). The state of the art allows the clinician to determine the dosage regimen for each individual patient, the active agents, and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, and the like. The formulations should provide a sufficient quantity of the active agents to effectively treat, prevent or ameliorate conditions, diseases, or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray, or inhalation. Actual methods for preparing parenterally or non-parenterally administrable formulations will be known or apparent to those skilled in the art and are described in more detail in such publications as *Remington: The Science and Practice of Pharmacy*, 21st ed., 2005.

Kits

Also provided are kits that contain at least one antibody or antigen-binding antibody fragment (e.g., Fab, F(ab')$_2$, Fab', scFv, di-scFv, or sdAb) that specifically binds to a soluble MANF protein (e.g., any of the soluble MANF proteins described herein) and at least one (e.g., two, three, or four) antibody or antigen-binding antibody fragment that specifically binds to one other marker of a pancreatic β-cell disorder (e.g., insulin, C-protein, and TAPP). In some embodiments, the antibodies or antigen-binding antibody fragments included in the kits are localized on a substrate (e.g., an enzyme-linked immunosorbent assay). In some embodiments, the kits can further include an isolated, purified, or recombinant soluble MANF protein (e.g., any of the soluble MANF proteins described herein). In some embodiments, one or more of the antibodies or antigen-binding antibody fragments is/are labeled (e.g., a radioisotope, a fluorophore, or a binding protein (e.g., avidin)). These kits can be useful for, e.g., for diagnosing a pancreatic β-cell disorder, identifying a subject at risk of developing a pancreatic β-cell in a subject, or monitoring pancreatic β-cell function or pancreatic β-cell mass in a subject. In some embodiments, the kits can further contain instructions for performing any of the methods described herein.

Reporter Proteins

The methods provided herein use reporter proteins that contain a binding protein (BiP) signal sequence (e.g., a mouse or a human BiP signal sequence), a redox-sensitive fluorescent protein (e.g., a redox-sensitive green fluorescent protein and a redox-sensitive yellow fluorescent protein), and the amino acid sequence KDEL (Lys-Asp-Glu-Leu). In some embodiments, the BiP signal sequence is at the N-terminus, the redox-sensitive fluorescent protein is C-terminal to the BiP signal sequence, and the amino acid sequence KDEL is C-terminal to the redox-sensitive fluorescent protein. In some embodiments, there are 1 to 100 amino acids (e.g., 1 to 50, 1 to 40, 1 to 30, 1 to 25, 1 to 20, 1 to 15, and 1 to 10 amino acids) between two or more of the individual protein elements present in the reporter protein (e.g., BiP signal sequence, the redox-sensitive fluorescent protein, and the KDEL sequence). The amino acid sequence of a redox-sensitive green fluorescent protein is listed below.

```
Redox Sensitive Green Fluorescent Protein
                                (SEQ ID NO: 10)
MSKGEELFTG VVPILVELDG DVNGHKFSVS GEGEGDATYG

KLTLKFIVTT GKLPVPWPTL VTTFXLQCFA RYPDHMKRHD

FFKSAMPEGY VQERTIFFKD DGNYKTRAEV KFEGDTLVNR

IELKGIDFKE DGNILGHKLE YNYNSHCVYI VADKQKNGIK

VNFKIRHNIE DGSVQLADHY QQNTPIGDGP VLLPDNHYLC

YQSALSKDPN EKRDHMVLLE FVTAAGITHG MDELYK
```

The reporter proteins described herein can contain a sequence at least 80% identical (e.g., at least 85%, 90%, 91%, 92%, 93%, 94%, 95%, 96%, 97%, 98%, or 99%) to SEQ ID NO: 10 (as long as the resulting protein maintains its redox-sensitive fluorescence properties). For example, mutations introduced into a redox-sensitive green fluorescent protein or a redox-sensitive yellow fluorescent protein should not include mutations in the cysteines. In some embodiments, the redox-sensitive fluorescent protein is a redox-sensitive yellow fluorescent protein (e.g., rxYFP; described in Ostergaard et al., *EMBO J.* 20:5853-5862, 2001). Additional examples of redox-sensitive fluorescent proteins are described in Merksamer et al. (*Cell* 135:933-947, 2008) and Dooley et al. (*J. Biol. Chem.* 279:22284-22293, 2004).

Exemplary human and mouse BiP signal sequences that can be present in the reporter protein are shown below. The reporter proteins used in the methods described herein can contain any mammalian BiP signal sequence (e.g., a human or mouse BiP signal sequence).

In some embodiments, the reporter protein and nucleic acids encoding these reporter proteins provides a means for sensitive (e.g., significantly improved) detection of subtle fluctuations in the redox environment within an intact pancreatic β-cell.

```
Human BiP Signal Sequence
                              (SEQ ID NO: 12)
MKLSLVAAMLLLLSAARA Mouse BiP Signal Sequence
                              (SEQ ID NO: 13)
MMKFTVAAALLLLGAVRA
```

In some embodiments, the reporter protein contains a sequence that is at least 80% identical (e.g., at least 85%, 90%, 91%, 92% 93%, 94%, 95%, 96%, 97%, 98%, 99%, or 100% identical) to a reporter protein containing the sequence of SEQ ID NO: 14 (shown below). In some embodiments, the reporter protein is encoded by a nucleic acid containing a sequence that is at least 80% identical (e.g., at least 85%, 90%, 91%, 92%, 93%, 94%, 95%, 96%, 97%, 98%, 99%, or 100% identical) to SEQ ID NO: 15. For example, mutations in the reporter protein of SEQ ID NO: 14 should not include mutations in the cysteines. Different mutants of SEQ ID NO: 14 can be tested using any of the methods described herein to determine whether the mutants maintain their redox-dependent fluorescence properties. The specific redox-dependent fluorescence properties of a protein containing a sequence at least 80% identical to SEQ ID NO: 14 (MEROS-GFP) are described in detail in the Examples.

MEROS-GFP protein
(SEQ ID NO: 14)
MMKFTVVAAALLLLGAVRAEEEDPPVATMSKGEELFTGVVPILVELDGDV

NGHKFSVSGEGEGDATYGKLTLKFISTTGKLPVPWPTLVTTFSYGVQCFS

RYPDHMKRHDFFKSAMPEGYVQERTIFFKDDGNYKTRAEVKFEGDTLVNR

IELKGIDFKEDGNILGHKLEYNYNCHKVYIMADKQKNGIKVNFKIRHNIE

DGSVQLADHYQQNTPIGDGPVLLPDNHYLKTCSALSKDPNEKRDHMVLLE

RVTAAGITHGMDELYKTSGGPPPTGEEDTSEKDEL

MEROS-GFP mRNA
(SEQ ID NO: 15)
atgatgaagttcactgtggtggcggcggcgttgctgctgctgggcgcggt gcgggccgaggaggaggatccaccggtcgccaccatgagtaaaggagaag aactttcactggagttgtcccaattcttgttgaattagatggtgatgtt aatgggcacaaattttctgtcagtggagagggtgaaggtgatgcaacata cggaaaacttaccataaatttatttccactactggaaaactacctgttcc atggccaacacttgtcactactttcagttatggtgttcaatgatttcaag atacccagatcatatgaaacggcatgacttttcaagagtgccatgcccg aaggttatgtacaggaaagaactatattttcaaagatgacgggaactac aagacacgtgctgaagtcaagtttgaaggtgataccctttgttaatagaat cgagttaaaaggtattgattttaaagaagatggaaacattatggacacaa attggaatacaactataactgccacaaggtatacatcatggcagacaaac aaaagaatggaatcaaagttaacttcaaaattagacacaacattgaagat ggaagcgttcaactagcagaccattatcaacaaaatactccaattggcga tggccctgtccttttaccagacaaccattacctgaagacatgctctgccc tttcgaaagatcccaacgaaaagagagaccacatggtccttcttgagcgc gtaacagctgctgggattacacatggcatggatgaactatacaaaactag tggaggccctcccccaactggtgaagaggatacatcagaaaaagatgagt tgtag Methods of Screening for Candidate Agents Also provided are methods of screening for a candidate compound useful for one of more of the following: treating or delaying the onset of a pancreatic β-cell disorder in a subject, decreasing endoplasmic reticulum stress in a pancreatic β-cell, and reducing or delaying endoplasmic reticulum stress-induced apoptotic cell death in pancreatic β-cells. These methods include providing a pancreatic β-cell, contacting the pancreatic β-cell with a candidate compound, and determining the level of soluble MANF produced by the pancreatic β-cell in the presence of the candidate compound, and comparing the level of soluble MANF produced by the pancreatic β-cell to a reference level of soluble MANF. In these methods, an elevated level of soluble MANF produced by the pancreatic β-cell compared to the reference level indicates that the test compound may be useful for one or more of the following: treating or delaying the onset of a pancreatic β-cell disorder in a subject, decreasing endoplasmic reticulum stress in a pancreatic β-cell, and reducing or delaying endoplasmic reticulum stress-induced apoptotic cell death in pancreatic β-cells.

The pancreatic β-cell(s) used in these methods can be any of the pancreatic β-cells described herein (e.g., a pancreatic β-cell line (e.g., any of the pancreatic β-cell lines described herein) or primary pancreatic β-cells).

The levels of soluble MANF may be determined using standard molecular biology methods (e.g., any of the antibody-based methods described herein). The methods can be performed by any health care professional (e.g., a physician, a nurse, a physician's assistant, a laboratory technician, or a nurse's assistant) or a scientist.

In some embodiments, the reference level is a level of soluble MANF produced by a pancreatic β-cell in the absence of the candidate compound. In some embodiments, the reference level is a level of soluble MANF present in a subject that does not have a pancreatic β-cell disorder, does not have a symptom of a pancreatic β-cell disorder, or a family history of a pancreatic β-cell disorder. In some embodiments, the reference level is a level of soluble MANF produced in a primary pancreatic β-cell from a mammal or a mammalian pancreatic β-cell line. In some embodiments, the reference level is a threshold level of soluble MANF.

Also provided are methods of screening for a candidate compound useful for treating or delaying the onset of a pancreatic β-cell disorder in a subject, decreasing endoplasmic reticulum stress in a pancreatic β-cell, and/or reducing or delaying endoplasmic reticulum stress-induced apoptotic cell death in pancreatic β-cells. These methods include providing a mammalian cell (e.g., a mammalian pancreatic β-cell or pancreatic β-cell line) expressing a reporter protein containing from a BiP signal sequence, a redox-sensitive fluorescent protein, and the amino acid sequence KDEL; contacting the cell with a test compound; determining the amount of oxidized reporter protein present in the cell; and comparing the amount of oxidized reporter protein present in the cell compared to a reference level; where an elevated level of oxidized reporter protein in the cell compared to the reference level indicates that the candidate compound may be useful for treating or delaying the onset of a pancreatic β-cell disorder in a subject, decreasing endoplasmic reticulum stress in a pancreatic β-cell, and/or reducing or delaying endoplasmic reticulum stress-induced apoptotic cell death in pancreatic β-cells. In some embodiments, the reference level is the amount of the oxidized reporter protein present in a mammalian cell in the absence of the candidate agent. In some embodiments, the cell is contacted with both the candidate agent and an agent that induces ER stress and the reference level is a level of oxidized reporter protein present in a cell treated with the agent that induces ER stress alone. Non-limiting examples of agents that induce ER stress are described herein. Additional examples of agents that induce ER stress are known in the art. In some embodiments, the reference level is a threshold level of oxidized reporter protein. The cells used can be human, mouse, rat, pig, monkey, or bovine cells. The cells can be any pancreatic β-cell line described herein or known in the art. In some embodiments, the reporter protein is SEQ ID NO: 14, or a protein containing a sequence that is at least 80% (e.g., at least 85%, 90%, 95%, 96%, 97%, 98%, or 99% identical) to SEQ ID NO: 14.

Also provided are methods of screening for a candidate compound useful for treating or delaying the onset of a pancreatic β-cell disorder in a subject, decreasing endoplasmic reticulum stress in a pancreatic β-cell, and/or reducing or delaying endoplasmic reticulum stress-induced apoptotic cell death in pancreatic β-cells. The methods include providing a mammalian cell (e.g., a mammalian pancreatic β-cell) expressing a reporter protein containing from a BiP signal sequence, a redox-sensitive fluorescent protein, and the amino acid sequence KDEL; contacting the cell with a test compound; determining the amount of reduced reporter protein present in the cell; and comparing the amount of reduced reporter protein present in the cell compared to a reference level; where an increased level of reduced reporter protein in the cell compared to the reference level indicates that the candidate compound may be useful for treating or delaying the onset of a pancreatic β-cell disorder in a subject, decreasing endoplasmic reticulum stress in a pancreatic β-cell, and/or reducing or delaying endoplasmic reticulum stress-induced apoptotic cell death in pancreatic β-cells. In some embodiments, the reference level is the amount of the reduced reporter protein present in a mammalian cell in the absence of the candidate agent. In some embodiments, the cell is contacted with both the candidate agent and an agent that induces ER stress and the reference level is a level of reduced reporter protein present in a cell treated with the agent that induces ER stress alone. Non-limiting examples of agents that induce ER stress are described herein. Additional examples of agents that induce ER stress are known in the art. In some embodiments, the reference level is a threshold level of reduced reporter protein. The cells used can be human, mouse, rat, pig, monkey, or bovine cells. The cells can be any pancreatic β-cell line described herein or known in the art. In some embodiments, the reporter protein is SEQ ID NO: 14, or a protein containing a sequence that is at least 80% (e.g., at least 85%, 90%, 95%, 96%, 97%, 98%, or 99% identical) to SEQ ID NO: 14.

In some embodiments, the determining is performed by detecting one or more fluorescence properties of the reporter protein in the cell (e.g., detecting spectral features that are unique for the reduced or oxidized form of the reporter protein). In some embodiments, the level of the reduced or oxidized form of the reporter protein is determined using a fluorescent plate reader or using fluorescence-assisted cell sorting (FACS).

For example, pancreatic β-cells (e.g., INS-1 832/13) expressing the reporter protein can be plated into 6-well plates, contacted with a candidate compound, and then harvested by trypsinization. After washing with phosphate buffered saline, the cells can be suspended in a suitable medium (e.g., 11 mM glucose-Hanks buffered salt solution), and FACS performed with LSRII (BD) to determine the levels of the reduced or oxidized form of the reporter protein present in the cell.

In some embodiments, a fluorescent plate reader can be used to determine the level of the reduced or oxidized form of the reporter protein present in the cell. For example, a pancreatic β-cell line (e.g., INS-1 832/13 cells) can be plated into 96-well plates and treated with a candidate agent. The levels of the reduced or oxidized form of the reporter protein can be detected using the fluorescent plate reader. In such embodiments, the substraction of background signal should be performed prior to determining the level of the reduced or oxidized form of the reporter protein.

In some embodiments, the reporter protein contains SEQ ID NO: 14 or a protein containing a sequence that is at least 80% identical to SEQ ID NO: 14. In these embodiments, the reduced form of the reporter protein has an excitation wavelength of 473 nm and an emission wavelength of 510 nm, and the oxidized form of the reporter protein has an excitation wavelength of 394 nm and an emission wavelength of 510 nm.

In some embodiments of these methods, a ratio of the level of the reduced form of the reporter protein to the level of the oxidized form of the reporter protein in the cell can be determined. In these methods, the calculated ratio can be compared to a reference ratio. The reference ratio can be the ratio from a cell that is not treated with a candidate agent. The reference ratio can also be a threshold ratio. In some embodiments, the cell is contacted with a candidate agent and an agent that induces ER stress, the ratio of the level of the reduced form of the reporter protein to the level of the oxidized form of the reporter protein in the cell is determined, and the ratio in the cell is compared to a reference ratio from a cell treated with the agent that induces ER stress alone. In these methods, a candidate agent that decreases the ratio in the cell as compared to the reference ratio is identified as a candidate agent for treating a pancreatic β-cell disorder in a subject.

Some embodiments of the above methods further include testing the candidate compound in an animal model of a pancreatic β-cell disorder (e.g., determining whether administration of the candidate compound will treat (e.g., reduce the severity, frequency, or duration) one or more symptoms of a pancreatic β-cell disorder in an animal model or delay the onset of one or more symptoms of a pancreatic β-cell disorder in an animal model). Non-limiting animal models of type 2 diabetes include Zucker fatty rats (ZFR), ob/ob (obese) mice, cp (corpulent) rats, Zucker diabetic fatty (ZDF) rats, sand rats (*Psammomys obesus*), obsess rhesus monkeys, KK mice, and KK-A$^y$ mice (described in Srinivasan et al., *Indian J. Med. Res.* 125:451-472, 2007). Non-limiting animal models of type 1 diabetes include non-obese diabetic (NOD) mice and bio breeding (BB) rats (described in Rees et al., *Diabetic Med.* 22:359-370, 2005). The severity or onset of one or more symptoms of a pancreatic β-cell disorder can be determined or observed in these animals using the methods described herein or methods known in the art.

Some embodiments of the above methods further include testing whether the candidate compound will decrease or delay endoplasmic reticulum stress-induced apoptotic cell death in a population of pancreatic β-cells (e.g., a reduction or delay in endoplasmic reticulum stress-induced apoptotic cell death in a population of pancreatic β-cells treated with the candidate agent and an agent that induces endoplasmic reticulum stress compared to a population of pancreatic β-cells treated with the agent that induces endoplasmic reticulum stress in the absence of the candidate agent). Methods for detecting apoptotic cell death are well-known in the art and include, without limitation, the cleavage of cellular caspases (e.g., procaspase-3 and procaspase-4), Hoescht and 7-amino-actinomycin uptake, TdT-mediated dUTP nick end labeling assay, and annexin membrane staining. A variety of kits for detecting apoptotic cell death are commercially available.

Some embodiments of the above methods further include testing whether the candidate compound prevents or delays the induction of other markers of endoplasmic reticulum stress in a pancreatic β-cell (e.g., whether the candidate compound reduces the induction of grp78 (BiP) or bag-1 expression; reduces activation, Golgi translocation, protease cleavage, or nuclear translocation of ATF6; reduces PERK activation, oligomerization, or autohosphorylation; reduce activation of IRE1; decreases phosphorylation of eIF2α; reduces the intron processing of XBP1 mRNA; reduces activation of a JNK signaling pathway; prevents activation and cleavage of procaspase 4; and/or prevents or decrease the shift in the endoplasmic reticulum redox environment (e.g., measured using any of the reporter proteins described herein)). Expression levels of BiP and Bag-1 can be determined using quantitative real-time PCR with sets of primers that are designed to hybridize to portions of BiP or Bag-1. Expression levels or the processing, activation, phosphorylation, or cellular localization of BiP, Bag-1, PERK, IRE1, eIF2α, XBP1, and ATF6 can also be determined using antibodies that specifically bind to one BiP, Bag-1, PERK, IRE1, eIF2α, XBP1, or ATF6 using methods known in the art. In some embodiments, the prevention or delay in one or more markers of endoplasmic reticulum stress is cells treated with the candidate agent and an agent that induces endoplasmic reticulum stress is compared to pancreatic β-cell(s) treated with the agent that induces endoplasmic reticulum stress in the absence of the candidate agent.

Any type of candidate compound can used in the above methods. A candidate compound, e.g., can be a protein, a peptide, a nucleic acid (e.g., RNA or DNA), an inorganic compound, a lipid, an oligosaccharide, or any combination thereof. Libraries of candidate compounds that can be used in the above methods are commercially available. The candidate compounds to be screened, can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam, Anticancer Drug Des., 12:145, 1997).

Examples of methods for the synthesis of molecular libraries can be found in the literature, for example in: DeWitt et al., *Proc. Natl. Acad. Sci. U.S.A.,* 90:6909, 1993; Erb et al., *Proc. Natl. Acad. Sci. U.S.A.,* 91:11422, 1994; Zuckermann et al., *J. Med. Chem.,* 37:2678, 1994; Cho et al., *Science* 261:1303, 1993; Carrell et al., *Angew. Chem. Int. Ed. Engl.,* 33:2059, 1994; Carell et al., *Angew. Chem. Int. Ed. Engl.,* 33:2061, 1994; and Gallop et al., *J. Med. Chem.,* 37:1233, 1994.

Libraries of compounds may be presented in solution (e.g., Houghten, *Bio/Techniques,* 13:412-421, 1992), or on beads (Lam, *Nature,* 354:82-84, 1991), chips (Fodor, *Nature* 364:555-556, 1993), bacteria (U.S. Pat. No. 5,223,409), spores (U.S. Pat. Nos. 5,571,698; 5,403,484; and 5,223,409), plasmids (Cull et al., *Proc. Natl. Acad. Sci. U.S.A.,* 89:1865-1869, 1992) or phage (Scott and Smith, *Science,* 249:386-390, 1990; Devlin, *Science,* 249:404-406, 1990; Cwirla et al., *Proc. Natl. Acad. Sci. U.S.A.,* 87:6378-6382, 1990; and Felici, *J. Mol. Biol.,* 222:301-310, 1991).

EXAMPLES

Example 1

Soluble MANF Expression is Increased During ER Stress in Pancreatic β-Cells

Experiments were performed to determine if expression of soluble MANF is induced in pancreatic β-cells in response to endoplasmic reticulum stress. These experiments were performed using rodent pancreatic β-cell lines (INS-1 832/13 and MIN6), primary mouse and human islets, and two different chemical agents that induce endoplasmic reticulum stress (thapsigargin and tunicamycin). INS-1 832/13 cells were cultured in RPMI-1640 containing 10% fetal bovine serum, penicillin, streptomycin, sodium pyruvate, and 0.1% β-mercaptoethanol. Primary islets were obtained from Prodo, and plated into 6-well plates precoated with laminin V produced by 804G cells, and cultured in CMRL medium supplemented with fetal bovine serum, non-essential amino acids, sodium pyruvate, and antibiotics.

Figure 2:
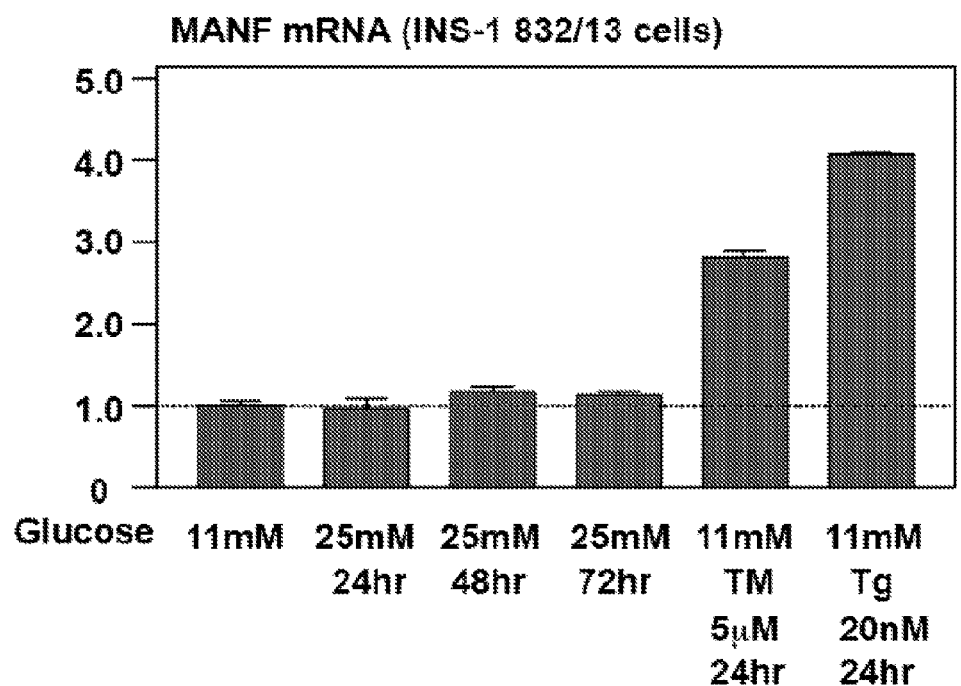
FIG. 2 is a graph showing the relative expression of MANF mRNA in a rat pancreatic β-cell line (INS-1 832/13) cultured under the following conditions: 11 mM glucose (24 hours); 25 mM glucose (24 hours); 25 mM glucose (48 hours); 25 mM glucose (72 hours); 11 mM glucose and 5 μM tunicamycin (TM) (24 hours); or 11 mM glucose and 20 nM thapsigargin (Tg) (24 hours). The data shown were generated using quantitative real-time PCR (n=3, S.D.).

Soluble MANF protein was detected in the medium of a cultured rat pancreatic β-cell line (INS-1 832/13) following treatment with thapsigargin (50 nM) (FIG. 1). Elevated levels of MANF mRNA were detected in the same cell line following treatment with either 5 µM tunicamycin or 20 nM thapsigargin for 24 hours (FIG. 2).

Figure 3:
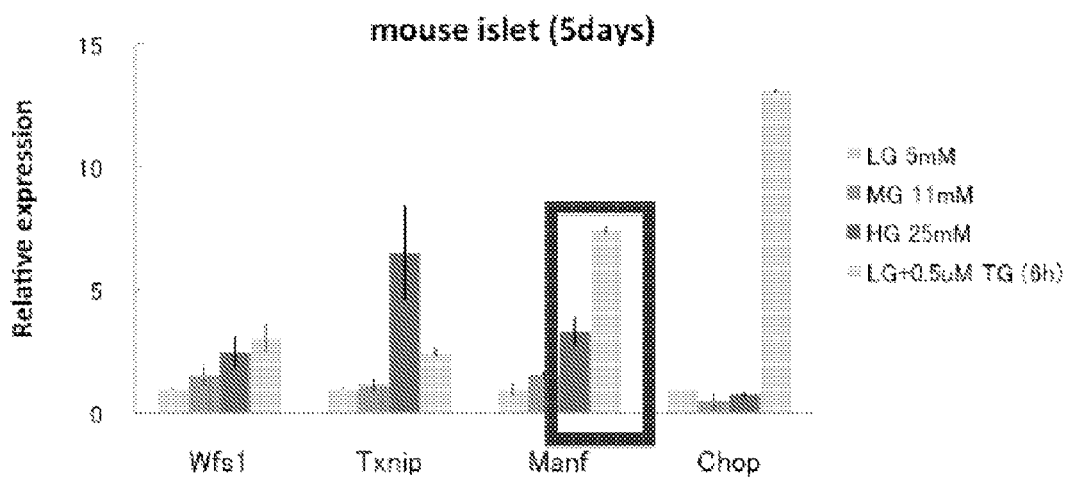
FIG. 3 is a graph showing the relative expression of MANF, WFS1, TXNIP, and CHOP mRNA in mouse primary islets cultured five days with 5 mM glucose (LG), 11 mM glucose (MG), or 25 mM glucose (HG), or five days with 5 mM glucose (LG) and 6 hours with 0.5 μM thapsigargin (TG). The data shown were generated using quantitative real-time PCR (n=3; S.D.).
Figure 4:
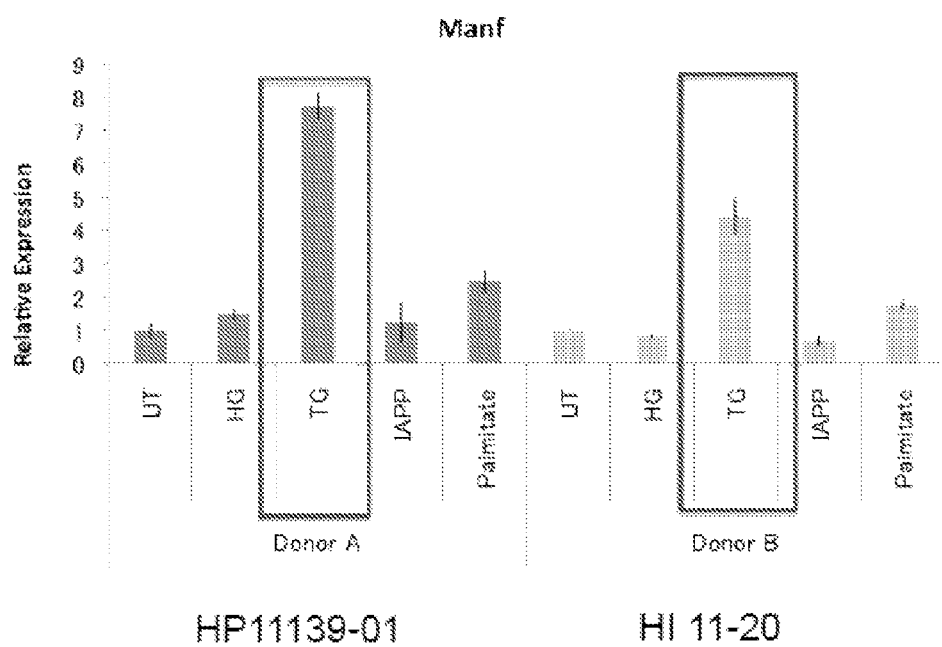
FIG. 4 is a graph showing the relative expression of MANF mRNA in human primary islets from two human donors (HP11139-01 and HI 11-20) following 24-hour treatment with 5.5 mM glucose (UT), 25 mM glucose (HG), 0.25 μM thapsigargin (TG), 10 μM islet amyloid polypeptide (IAPP), or 500 μM palmitate with bovine serum albumin (Palmitate). The data shown were generated using quantitative real-time PCR (n=3; S.D.).
Figure 5:
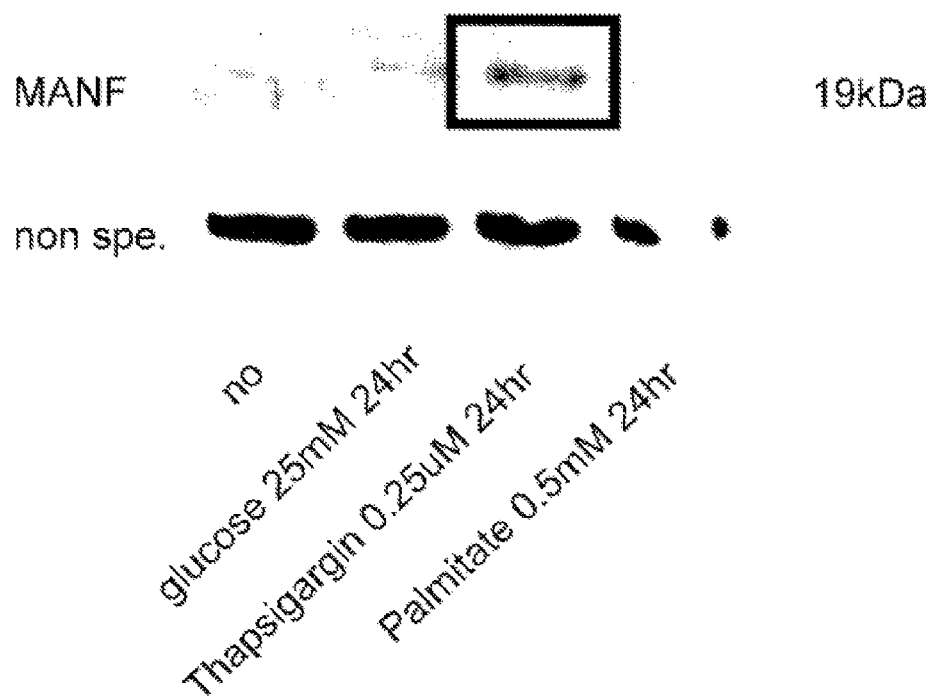
FIG. 5 is an immunoblot showing the level of soluble MANF in the medium of human primary islets following no additional treatment or treatment with 25 mM glucose (24 hours), 0.25 μM thapsigargin (24 hours), or 0.5 mM palmitate (24 hours).
Figure 6:
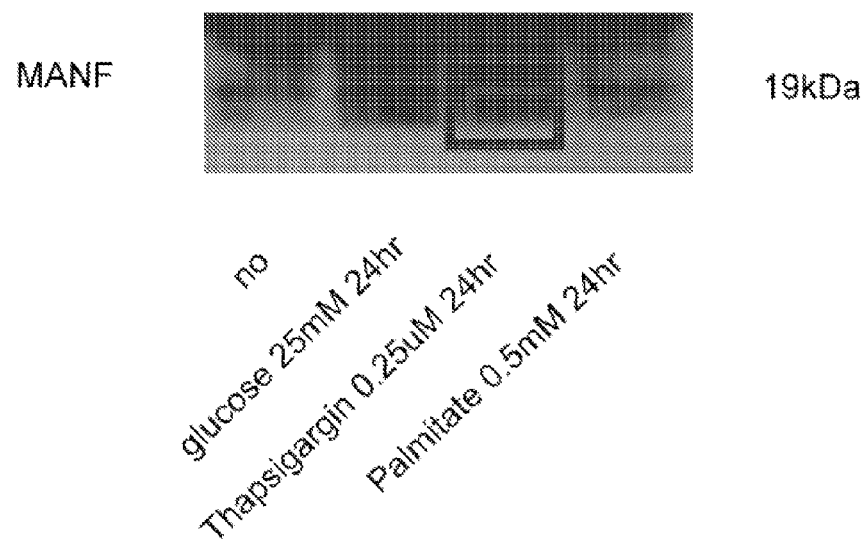
FIG. 6 is an immunoblot showing the level of soluble MANF immunoprecipitated from the medium of human primary islets following no additional treatment or treatment with 25 mM glucose (24 hours), 0.25 μM thapsigargin (24 hours), or 0.5 mM palmitate (24 hours). In this experiment, human MANF was immunoprecipitated using a rabbit anti-human MANF antibody (Proteintech), and the same antibody was used to develop the immunoblot.

The data from experiments performed using mouse primary islets further show that treatment of mouse islets with 0.5 µM thapsigargin for 6 hours results in a significant increase in MANF mRNA expression (FIG. 3). A second set of experiments were performed using human primary islets from two human donors. These data also show that treatment of human islets with thapsigargin (0.25 µM) results in a significant increase in MANF mRNA expression (FIG. 4), and the production and release of soluble MANF protein into the extracellular medium (FIGS. 5 and 6).

Figure 7:
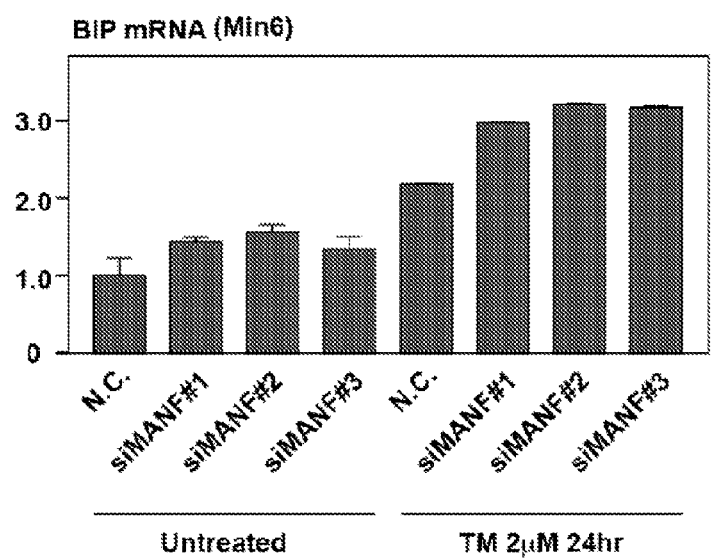
FIG. 7 is a graph showing the relative expression of BiP mRNA in a murine pancreatic β-cell line (MIN6) transfected with a negative control siRNA (NC) or one of three different siRNA molecules targeting MANF mRNA (siMANF#1, siMANF#2, or siMANF#3) following no treatment or treatment with 2 µM tunicamycin for 24 hours. These data were generated using quantitative real-time PCR (n=3; S.D.).

Experiments were performed to determine whether soluble MANF protects pancreatic β-cells from endoplasmic reticulum stress. In a first set of experiments, MANF expression was knocked down using one of three different siRNA constructs targeting MANF mRNA. Lipofectamine 2000 was used according to the manufacturer's protocol to perform the transfections. The data from these experiments show that knockdown of MANF expression results in increased endoplasmic reticulum stress (as indicated by an increase in BiP mRNA levels) when the cells are treated for 24-hours with tunicamycin (2 µM) compared to control cells transfected with a control siRNA and treated with the same level of tunicamycin (FIG. 7). These data indicate that soluble MANF plays a role in preventing or decreasing endoplasmic reticulum stress in pancreatic β-cells.

Figure 8:
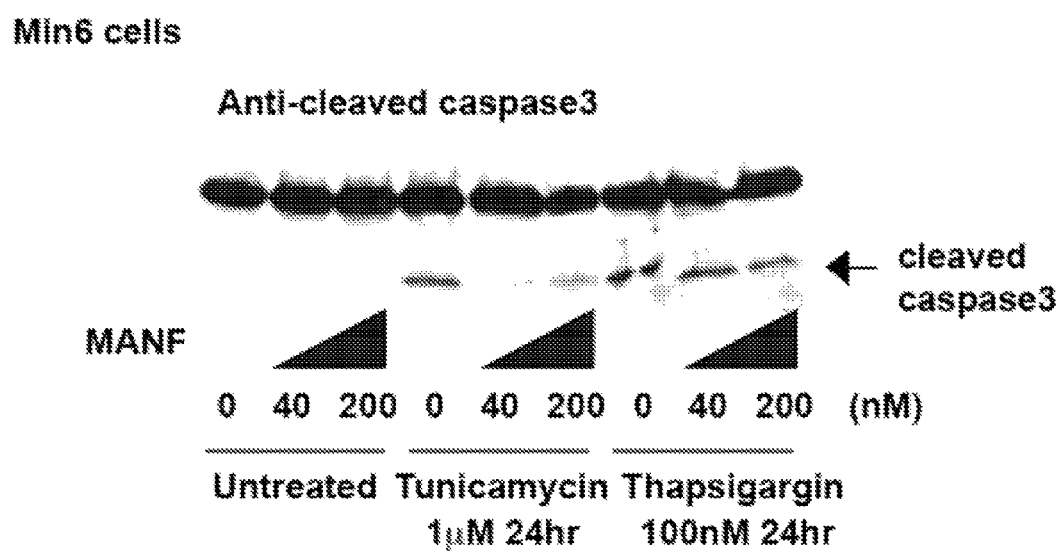
FIG. 8 is an immunoblot showing the levels of cleaved caspase-3 in a murine pancreatic β-cell line (MIN6) untreated or treated for 24-hours with 1 µM tunicamycin or 100 nM thapsigargin, and further treated with 0, 40, or 200 nM soluble MANF.

Additional experiments were performed to determine whether soluble MANF would decrease or delay endoplasmic reticulum stress-induced apoptosis in pancreatic β-cells treated with an endoplasmic reticulum stress-inducing chemical agent. The data from these experiments show that treatment of a mouse pancreatic β-cell line (MIN6) with soluble MANF significantly reduced the amount of caspase-3 cleavage observed in the cells following treatment with tunicamycin (1 nM, 24 hours) (FIG. 8). These data indicate that soluble MANF can prevent or delay endoplasmic reticulum stress-induced apoptotic cell death in pancreatic β-cells.

Example 2

System for Monitoring Redox States in the ER

Figure 9:
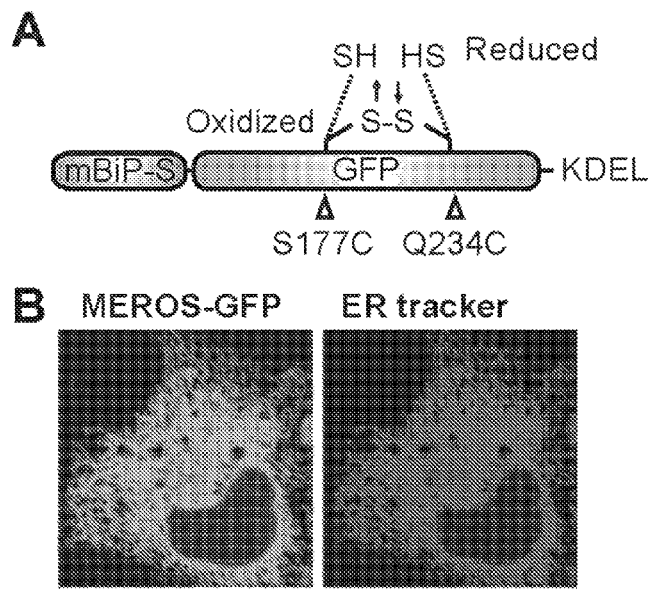
FIG. 9A is a diagram of Mammalian Endoplasmic Reticulum-Localized RedOx-Sensitive GFP (MEROS-GFP).
FIG. 9B is two confocal images of COS7 cells. The fluorescence of MEROS-GFP is shown in the left panel and the fluorescence of DsRed-ER tracker is shown in the right panel.

A new system to monitor the redox state of the ER in a cell was developed. In this system, the signal sequence of mouse BiP and the mammalian ER retrieval signal(KDEL), was appended to the N- and C-terminus of the redox-sensitive green fluorescent protein (GFP), respectively (FIG. 9A). The recombinant protein was named MEROS-GFP (Mammalian Endoplasmic Reticulum-Localized RedOx-Sensitive GFP).

Figure 10:
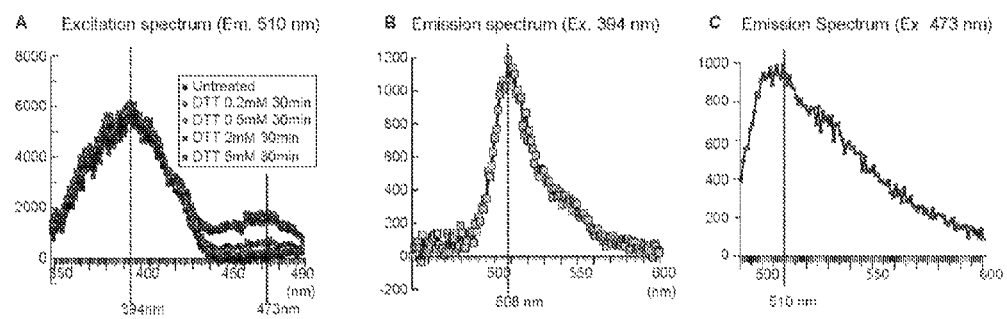
FIG. 10A is a set of excitation spectra of MEROS-GFP following no treatment or treatment with DTT at different concentrations (emission wavelength of 510 nm).
FIG. 10B is an emission spectrum of oxidized MEROS-GFP in untreated NSC34 cells (excitation wavelength of 394 nm).
FIG. 10C is an emission spectrum of reduced MEROS-GFP in NSC34 cells treated with 2 mM DTT (excitation wavelength of 473 nm).

Fluorescence microscopy was used to confirm that MEROS-GFP was localized to the ER (FIG. 9B). MEROS-GFP displayed distinct excitation spectra in the fully oxidized and reduced species in NSC34 cells, with maxima at 394 nm and 473 nm (FIG. 10A). NSC 34 cells were cultured in DMEM containing 10% fetal bovine serum, penicillin, and streptomycin.

Figure 11:
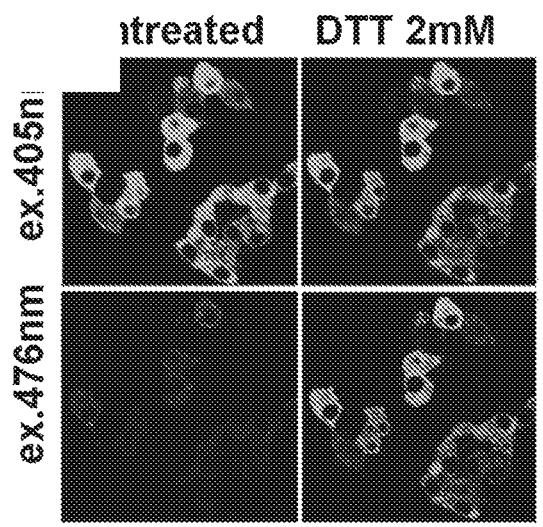
FIG. 11 is a set of four confocal microscopy images of MEROS-GFP gathered using a 476-nm excitation wavelength (bottom two panels) or a 405-nm excitation wavelength (top two panels) in INS-1 832/13 cells treated with (right two panels) or without (left two panels) 2 mM DTT.

The emission spectra from the two distinct excitation wavelengths, 508 nm and 510 nm, were comparable (FIGS. 10B and 10C). Confocal microscopy analysis confirmed that fluorescence from 476 nm excitation significantly increased, while fluorescence at 405 nm slightly decreased, in cells treated with the strong reducing agent dithiothreitol (DTT) (FIG. 11).

Figure 12:
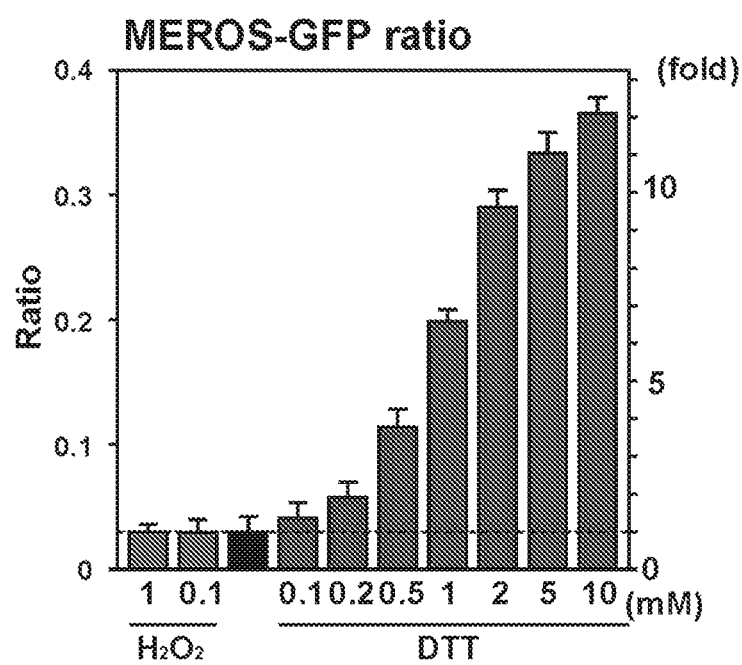
FIG. 12 is a graph of the MEROS-GFP ratio in INS-1 832/13 cells left untreated (no label), or treated with $H_2O_2$ (1 or 0.1 mM $H_2O_2$) or DTT (0.1, 0.2, 0.5, 1, 2, 5, or 10 mM DTT). The MEROS-GFP ratio was determined using a plate reader. The data shown are mean±S.D. (n=3).

The ratio between fluorescence from excitation 473 nm versus 394 nm normalized to wild-type untreated cells is called the MEROS-GFP ratio. The MEROS-GFP ratio was determined using a fluorescent plate reader. In these experiments, the INS-1 832/13 cells were plated onto a 96-well plate at 50,000 cells/well, the cells treated with $H_2O_2$ or DTT at various concentrations for 30 minutes, and the fluorescence at excitation wavelength 473 nm and emission wavelength 510 nm (for reduced MEROS-GFP) or at excitation wavelength 394 nm and emission wavelength 510 nm (for oxidized MEROS-GFP) was measured. The MEROS-GFP ratio was determined after substraction of background signal. The data show that an oxidizing agent, $H_2O_2$, did not change the MEROS-GFP ratio-indicating that MEROS-GFP is almost 100% oxidized in vivo (FIG. 12). In contrast, DTT treatment increased the MEROS-GFP ratio in a dose-dependent manner (FIG. 12).

Figure 13:
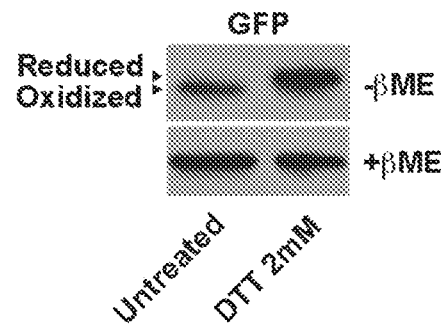
FIG. 13 is photograph of non-reducing polyacrylamide gel electrophoresis (PAGE) of 4-acetamido-4'-maleimidyl-stilbene-2,2'-disulfonic acid (AMS)-modified MEROS-GFP in lysate from cells left untreated (left lane) or treated with 2 mM DTT (right lane). The lysates were either left untreated (−βME) (top) or were treated with β-mercaptoethanol (+βME) (bottom) prior to electrophoresis.

Additional experiments were performed to confirm that the MEROS-GFP ratio reflected changes in its redox state in vivo. In these experiments, the redox state of MEROS-GFP was monitored using non-reducing SDS-PAGE in combination with the thiol-alkylating reagent, 4-acetamido-4'-maleimidylstilbene-2,2'-disulfonic acid (AMS). In these experiments, INS-1 832/13 cells left untreated or treated with 2 mM DTT, were lysed with 1×SDS-PAGE sample buffer containing 25 mM AMS with or without 2-β-mercaptoethanol, boiled at 95° C. for 10 minutes, electrophoresed using SDS-PAGE, and immunoblotted using an anti-GFP antibody. As expected, non-reducing SDS-PAGE of lysates from DTT-treated cells showed only one slower migrating form of MEROS-GFP, indicating that the DTT treatment fully reduced MEROS-GFP in vivo (FIG. 13).

Figure 14:
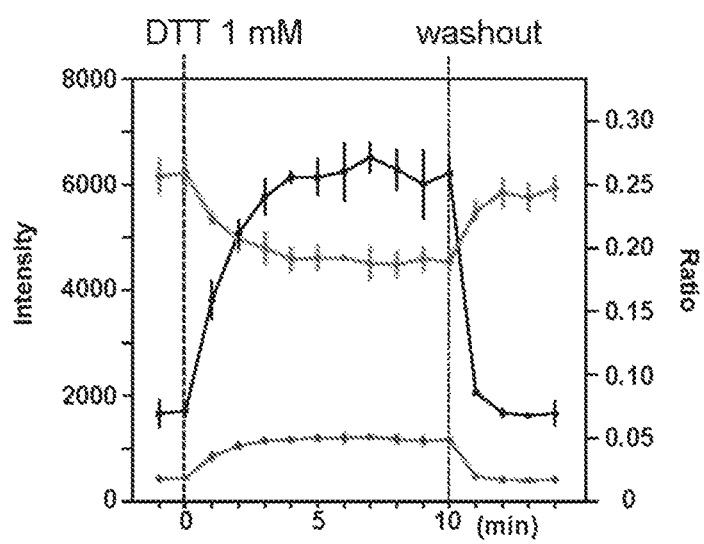
FIG. 14 is a graph showing a time course of the MEROS-GFP ratio in NSC34 cells that are treated with 1 mM DTT for 10 minutes, and then washed. The MEROS-GFP ratio was calculated at each minute interval between one minute prior to treatment to four minutes after the wash. The bottom line represents the fluorescence observed with excitation at 473 nm, the black line represents the MEROS-GFP ratio, and the light grey line represents the fluorescence with excitation at 394 nm (n=3; S.D.).

The MEROS-GFP ratio was also monitored in DTT-treated cells at different time points. FIG. 14 shows that the ER could be reduced within a few minutes of treatment of DTT, and return to an oxidized environment within a minute of DTT washout. These results indicate that MEROS-GFP can be used for real-time, live-monitoring of the redox state within the ER of mammalian cells.

Figure 15:
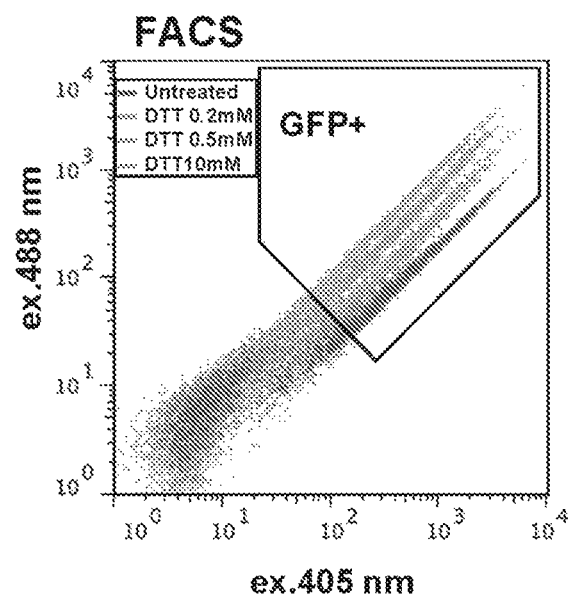
FIG. 15 is fluorescence-assisted cell sorting (FACS) data of INS-1 832/13 cells stably-transfected with MEROS-GFP following no treatment or treatment with DTT (0.2, 0.5, or 10 mM DTT). The data was collected using excitation wavelengths of 488 nm and 405 nm, and an emission spectrum of 510 nm. Going from bottom to top, the different sets of data are untreated, 0.2 mM DTT, 0.5 mM DTT, and 10 mM DTT (indicating a shift to a more reduced state following treatment with increasing concentrations of DTT).
Figure 16:
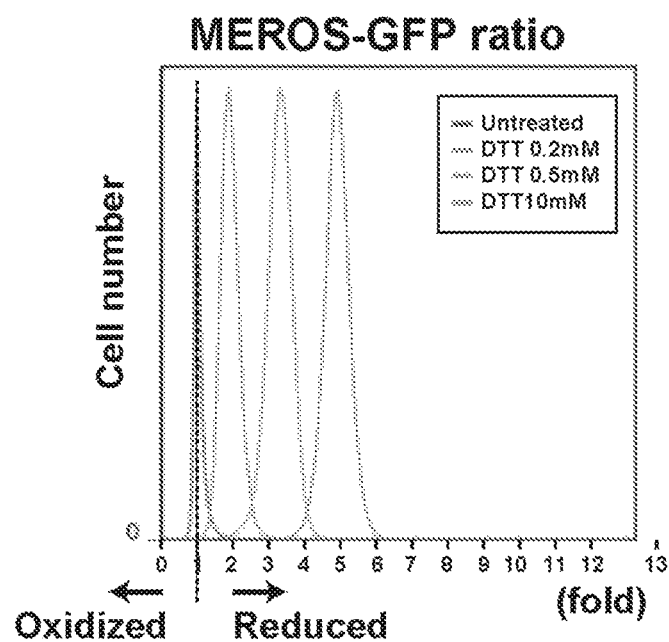
FIG. 16 is a histogram of FACS data of INS-1 832/13 cells stably-transfected with MEROS-GFP following no treatment or treatment with DTT (0.2 mM, 0.5 mM, or 10 mM DTT). The horizontal axis represents the MEROS-GFP ratio and the vertical axis represents the number of cells. The peaks from left to right represent cells left untreated, 0.2 mM DTT-treated, 0.5 mM DTT-treated, and 10 mM DTT-treated.
Figure 17:
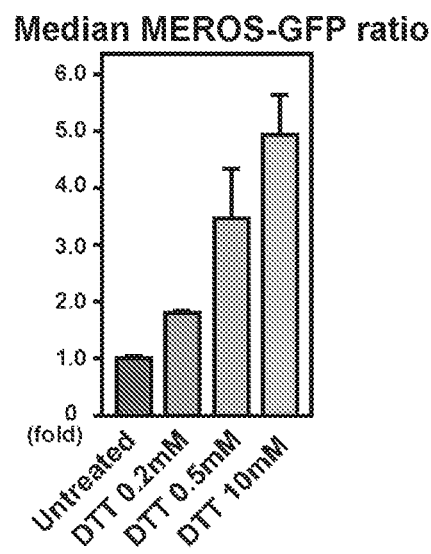
FIG. 17 is a graph of the median MEROS-GFP ratio in INS-1 832/13 cells stably-transfected with MEROS-GFP following no treatment or treatment with DTT (0.2, 0.5, or 10 mM DTT). The MEROS-GFP values shown are normalized to the untreated values.
Figure 18:
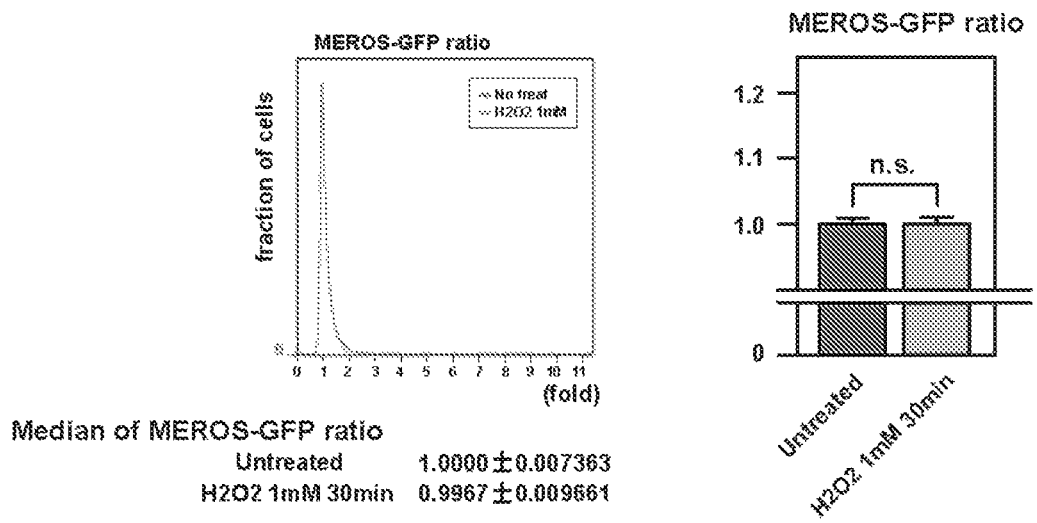
FIG. 18 is two graphs showing data from FACS analysis of INS-1 832/13 cells stably-transfected with MEROS-GFP following no treatment or treatment with 1 mM $H_2O_2$ for 30 minutes. The right graph is a histogram of the MEROS-GFP ratio in INS-1 832/13 cells not treated or treated with 1 mM $H_2O_2$. The left graph shows the median MEROS-GFP ratio in INS-1 832/13 cells not treated (left) or treated with 1 mM $H_2O_2$ for 30 minutes.
Figure 19:
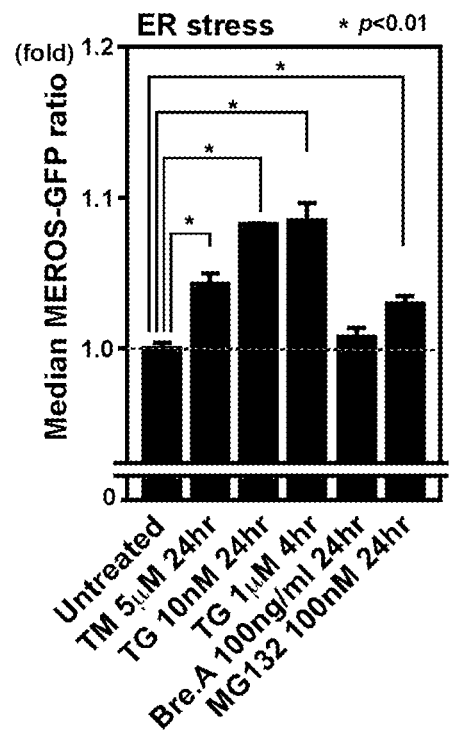
FIG. 19 is a graph of the median MEROS-GFP ratio calculated in INS-1 832/13 cells using FACS analysis following no treatment or treatment with tunicamycin (TM) (5 µM; 24 hours), thapsigargin (TG) (10 nM; 24 hours), TG (1 µM; 4 hours), brefeldin A (BreA) (100 ng/mL; 24 hours), or MG132 (100 nm; 24 hours). The error bars represent ±S.D. (* p<0.01). The data are normalized to the median MEROS-GFP ratio calculated for the untreated cells.
Figure 20:
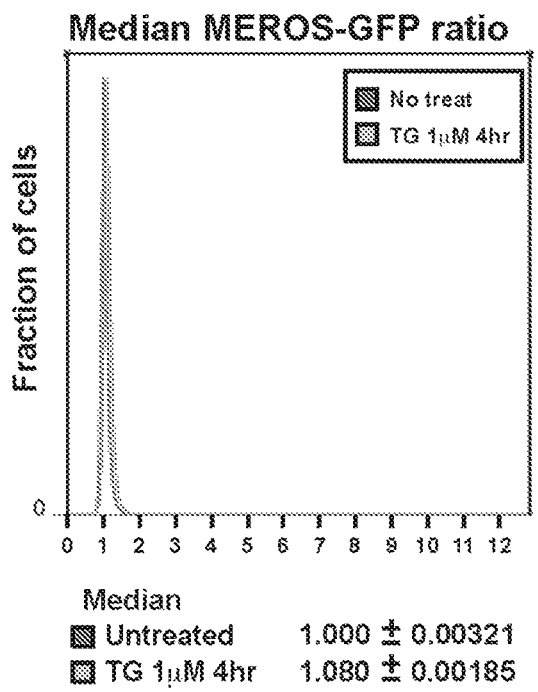
FIG. 20 is a histogram showing the MEROS-GFP ratio in INS-1 832/13 cells left untreated or treated with 1 µM thapsigargin (TG) for 4 hours.
Figure 21:
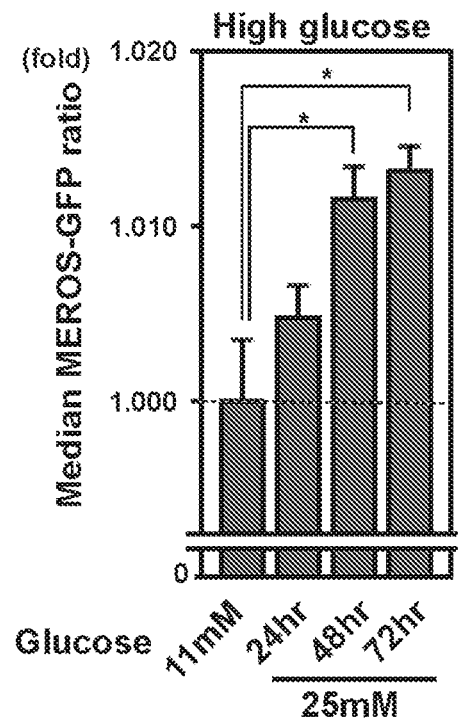
FIG. 21 is a graph of the median MEROS-GFP ratio calculated in INS-1 832/13 cells using FACS analysis following treatment with 11 mM glucose (24 hours) or 25 mM glucose for 24, 48, or 72 hours. The error bars represent ±S.D. The data are normalized to the median MEROS-GFP ratio calculated for the cells treated with 11 mM glucose for 24 hours.
Figure 22:
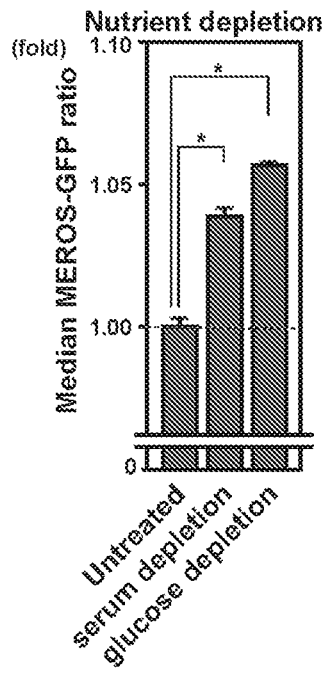
FIG. 22 is a graph of the median MEROS-GFP ratio calculated in INS-1 832/13 cells using FACS analysis following no treatment, serum depletion, or glucose depletion. The error bars represent ±S.D. (* p<0.01). The data are normalized to the median MEROS-GFP ratio calculated for the untreated cells.
Figure 23:
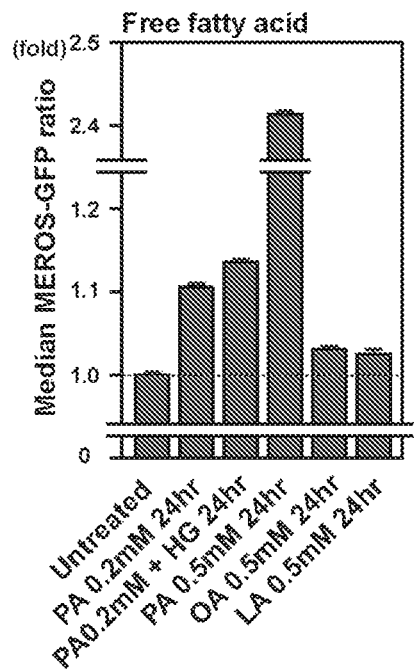
FIG. 23 is a graph of the median MEROS-GFP ratio in INS-1 832/13 cells left untreated or treatment with palmitic acid (0.2 mM; 24 hours), palmitic acid (0.2 mM) and high glucose (25 mM) (24 hours), palmitic acid (0.5 mM; 24 hours), oleic acid (0.5 mM; 24 hours), or linoleic acid (0.5 mM; 24 hours). The error bars represent ±S.D. The data are normalized to the median MEROS-GFP ratio calculated for the untreated cells.
Figure 24:
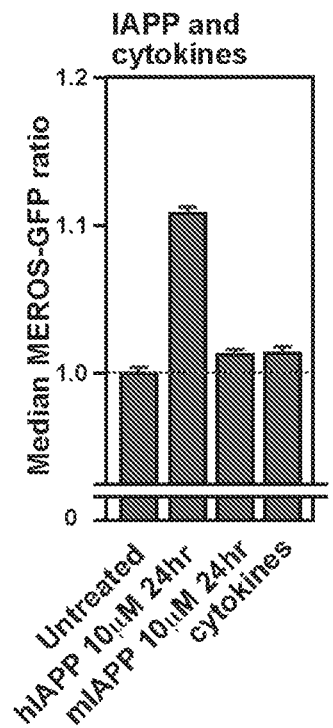
FIG. 24 is a graph of the median MEROS-GFP ratio in INS-1 832/13 cells left untreated or treatment with human islet amyloid polypeptide (IAPP) (10 µM; 24 hours), mouse IAPP (10 µM; 24 hours), or cytokines (interleukin-1β (5 ng/mL), IFNγ (100 ng/mL), and TNFα (25 ng/mL); 24 hours)). The error bars represent ±S.D. The data are normalized to the median MEROS-GFP ratio calculated for the untreated cells.

Flow cytometry was used to precisely monitor the MEROS-GFP ratio in vivo. These data show that treatment of the pancreatic β-cell line, INS-1 832/13, with DTT resulted in a dose dependent increase in the ratio of fluorescence from excitation at 488 nm versus 405 nm (FIGS. 15 and 16). To further analyze this observation, the median MEROS-GFP ratio was examined in DTT-treated cells. The data show that DTT treatment increased the median MEROS-GFP ratio in a dose-dependent manner (FIG. 17). However, $H_2O_2$ treatment did not change the MEROS-GFP ratio (FIG. 18), indicating that MEROS-GFP was almost fully oxidized in the ER at basal levels. The median MEROS-GFP ratio was also increased by both experimental and physiological inducers of ER stress, including tunicamycin, thapsigargin, brefeldin A, MG 132 (FIGS. 19 and 20), chronic high glucose (FIG. 21), serum depletion, glucose deprivation (FIG. 22), palmitate, human islet amyloid polypeptide (hIAPP), and inflammatory cytokines (FIGS. 23 and 24).

Example 3

Heterogeneity in ER Redox States in ER Stressed Cells

Figure 25:
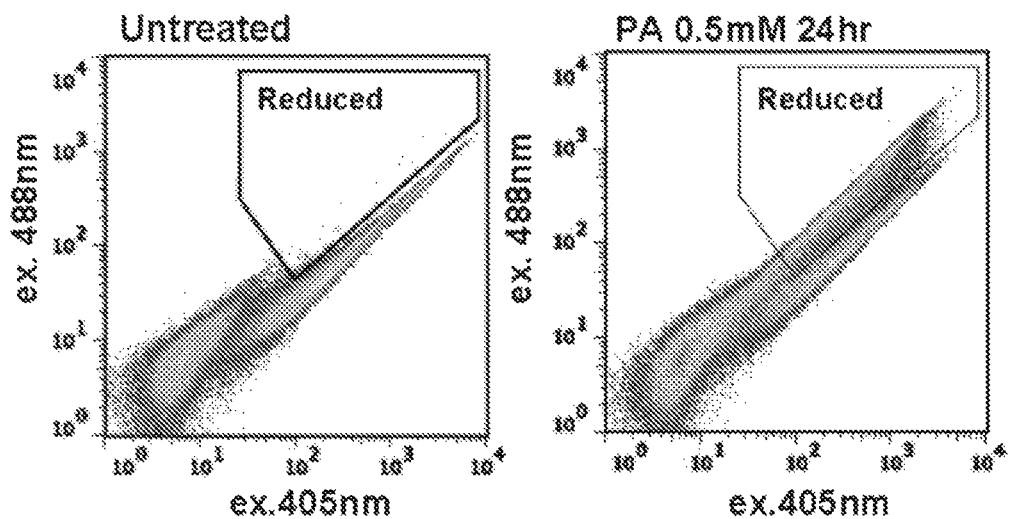
FIG. 25 is two graphs of FACS data from INS-1 832/13 cells left untreated (left) or treated with 0.5 mM palmitate (PA) for 24 hours. The y-axis represents fluorescence following excitation using 488 nm and the x-axis represents fluorescence following excitation using 405 nm.
Figure 26:
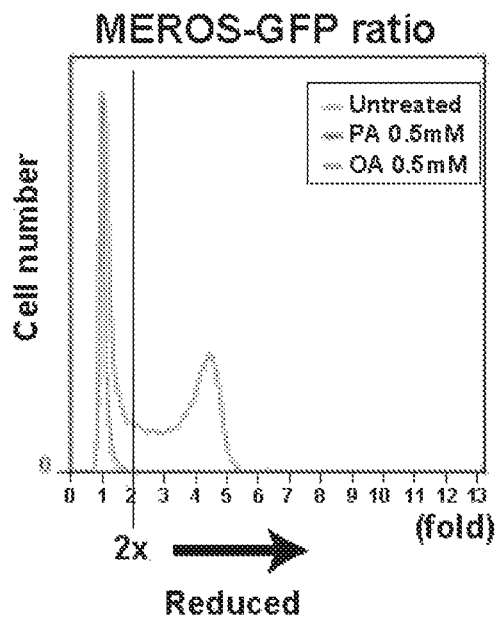
FIG. 26 is a graph showing the MEROS-GFP ratio calculated using FACS analysis in INS-1 832/13 cells following no treatment or treatment with 0.5 mM palmitate (PA) or 0.5 mM oleic acid (OA) for 24 hours. The data for cells treated with palmitate is shifted to the right.
Figure 27:
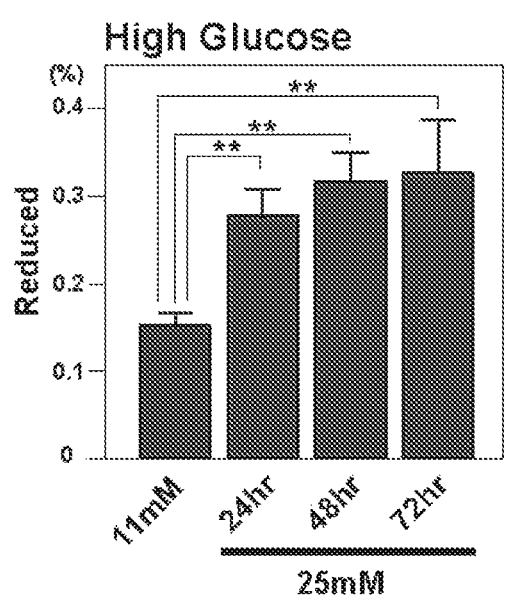
FIG. 27 is a graph showing the percentage of reduced cells in a population of INS-1 832/13 cells following treatment with 11 mM glucose for 24 hours or 25 mM glucose for 24, 48, or 72 hours. The error bars indicate ±standard deviation (** p<0.01).
Figure 28:
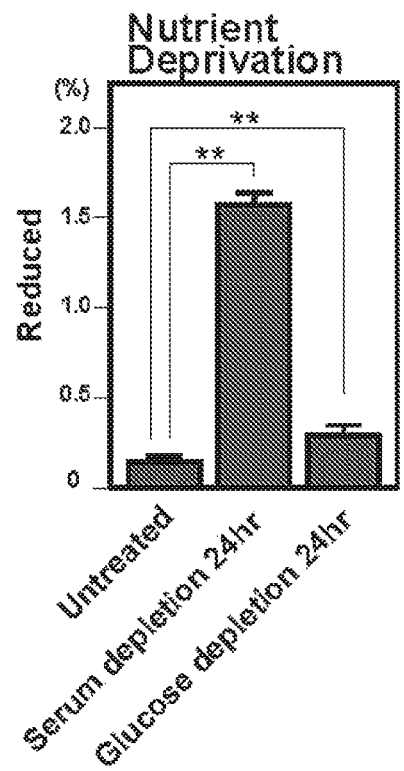
FIG. 28 is a graph showing the percentage of reduced cells in a population of INS-1 832/13 cells following no treatment, serum depletion for 24 hours, or glucose depletion for 24 hours. The error bars indicate ±standard deviation (** $p<0.01$).
Figure 29:
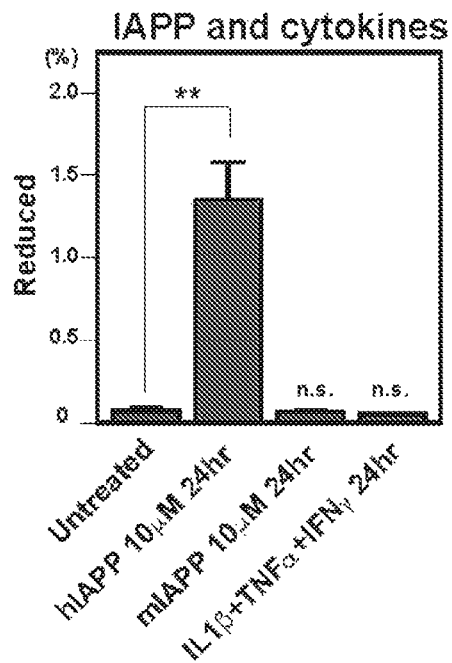
FIG. 29 is a graph showing the percentage of reduced cells in a population of INS-1 832/13 cells following no treatment or treatment with 10 μM human IAPP, 10 μM mouse IAPP, or a combination of interleukin-1β (5 ng/mL), IFNγ (100 ng/mL), and TNFα (25 ng/mL) for 24 hours. The error bars indicate ±standard deviation (** $p<0.01$).
Figure 30:
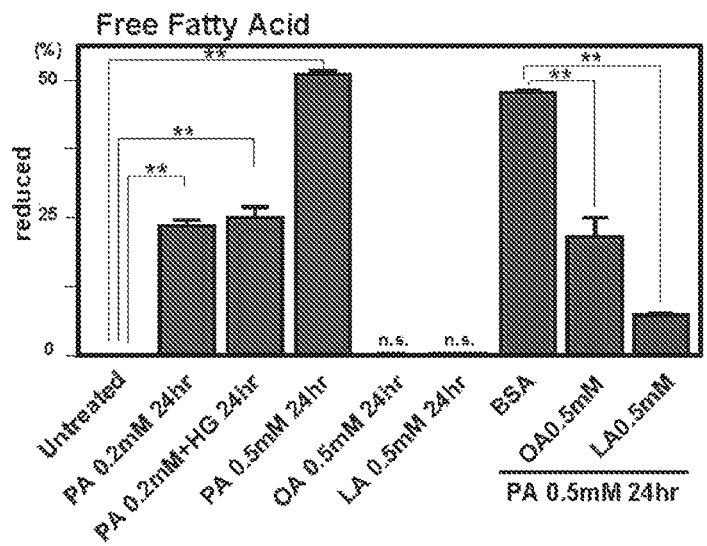
FIG. 30 is a graph showing the percentage of reduced cells in a population of INS-1 832/13 cells following no treatment or treatment for 24 hours with 0.2 mM palmitate, 0.2 mM palmitate and 25 mM glucose, 0.5 mM palmitate, 0.5 mM oleic acid, 0.5 mM linoleic acid, bovine serum albumin and 0.5 mM palmitate, 0.5 mM palmitate and 0.5 mM oleic acid, and 0.5 mM palmitate and 0.5 mM linoleic acid. The error bars indicate ±standard deviation (** $p<0.01$).

Two distinct cell populations were observed by flow cytometry following the treatment of INS-1 832/13 cells with palmitate (a strong ER inducer for pancreatic β cells): one that could maintain an oxidized ER state, and another that had a highly reduced ER (FIGS. 25 and 26). In order to further study these heterogenous populations of cells, the cells that had a MEROS-GFP ratio of greater than 2 were categorized as "reduced cells." These two different populations of cells were also observed following treatment with other known ER stress inducers for pancreatic β-cells, including chronic high glucose (FIG. 27), serum depletion, glucose deprivation (FIG. 28), and human IAPP (FIG. 29). Among the stress inducers, palmitate treatment leads to the greatest increase in cell population with highly reduced ER. Interestingly, the unsaturated fatty acids, oleic and linoleic acid, which have previously been shown to be protective against palmitate-induced cell dysfunction, significantly suppressed the ability of palmitate to create a reduced ER (FIG. 30). These data indicate that ER-stressed cells are heterogenous in their redox state.

Example 4

Activation of the Unfolded Protein Response (UPR) in Cells with a Reduced ER

Figure 31:
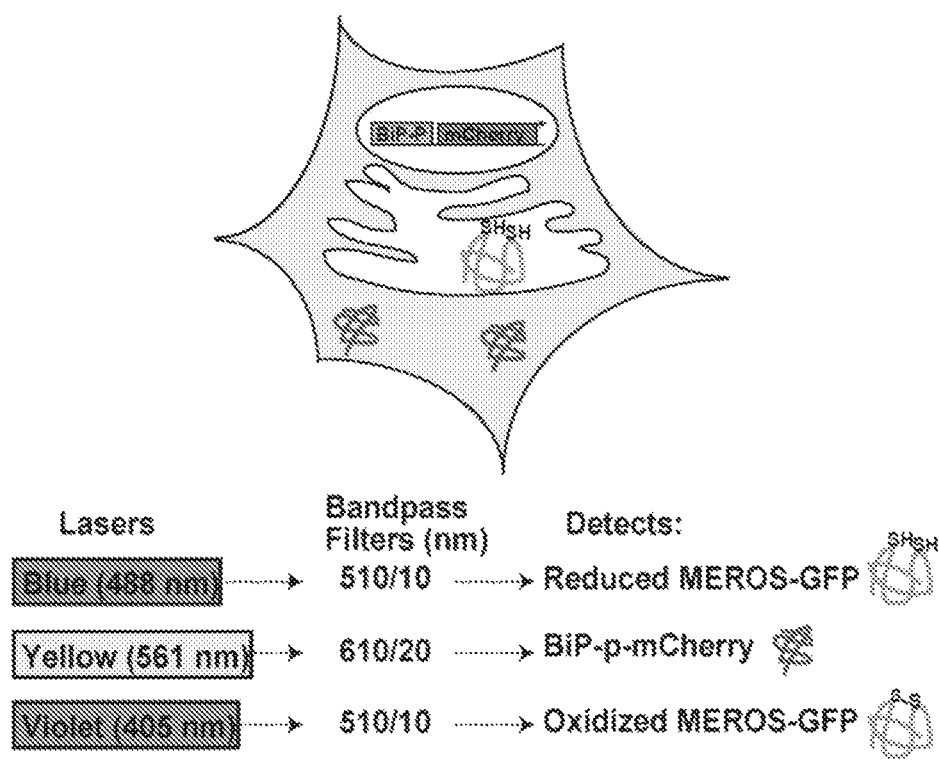
FIG. 31 is a diagram of cells transfected with BiP-P-mCherry and a diagram showing the configuration of flow cytometer laser lines and filters.

Experiments were performed to study the relationship between the UPR and the heterogeneity of the redox state. In these experiments, both the redox state and the activation levels of the UPR were monitored in the same cells. To achieve this, a UPR reporter gene encoding the red fluorescent protein, mCherry, driven by the human BiP promoter was constructed. The BiP promoter contains three unfolded protein response elements (UPRE) and has been shown to efficiently reflect the activation levels of the UPR. This BiP-mCherry reporter plasmid was transfected into INS-1 832/13 cells expressing MEROS-GFP, and FACS analysis was used to monitor the MEROS-GFP ratio and the activation levels of the UPR via BiP-mCherry in the same cells (FIG. 31). The activation levels of BiP-mCherry and the MEROS-GFP ratio were monitored following the induction of ER stress. In these experiments, INS-1 832/13 cells expressing MEROS-GFP were plated onto 6-well plates, treated with each compound for indicated times, and then harvested by trypsinization. After washing with phosphate buffered saline, cells were resuspended in the 11 mM glucose-Hanks buffered salt solution. Flow cytometry analyses were performed with LSRII (BD).

Figure 32:
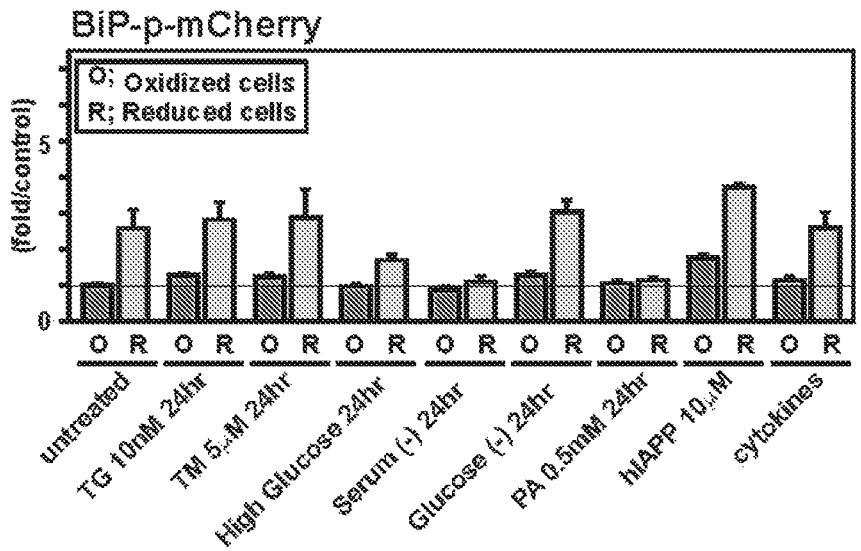
FIG. 32 is a graph of the median BiP-P-mCherry expression in oxidized or reduced INS-1 832/13 cells. The cells were either left untreated or were treated for 24 hours with 10 nM thapsigargin, 5 μM tunicamycin, 25 mM glucose, serum deprivation, glucose deprivation, 0.5 mM palmitate, 10 μM human IAPP, or a combination of interleukin-1β (5 ng/mL), IFNγ (100 ng/mL), and TNFα (25 ng/mL). The BiP-P-mCherry expression was determined using FACS analysis. The error bars indicate ±standard deviation.
Figure 33:
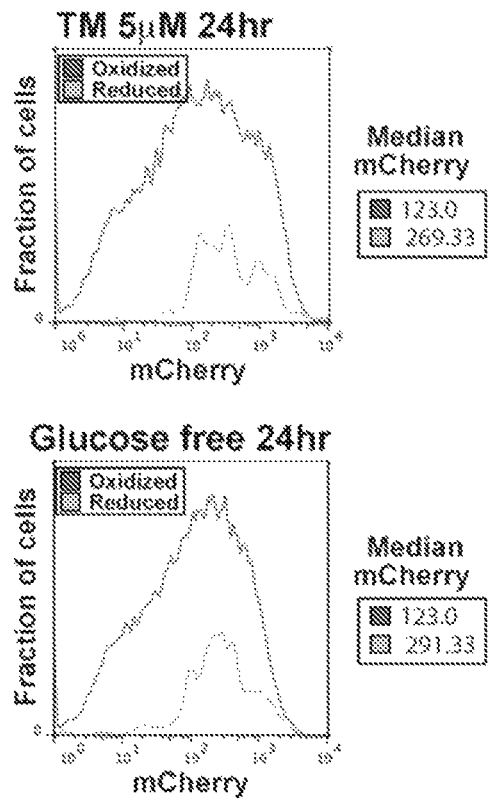
FIG. 33 is two histograms showing oxidized and reduced INS-1 832/13 cells treated with 5 μM tunicamycin (TM, upper histogram) or glucose deprivation (lower histogram) for 24 hours. The x-axis indicates the expression level of mCherry driven by human BiP promoter.

The data show that the cell population with reduced ER (the MEROS-GFP ratio>2.0) had higher activation levels of BiP-mCherry as compared to the cells that could maintain an oxidized ER, signifying activation of the UPR in the highly reduced ER cell population (FIGS. 32 and 33).

Figure 34:
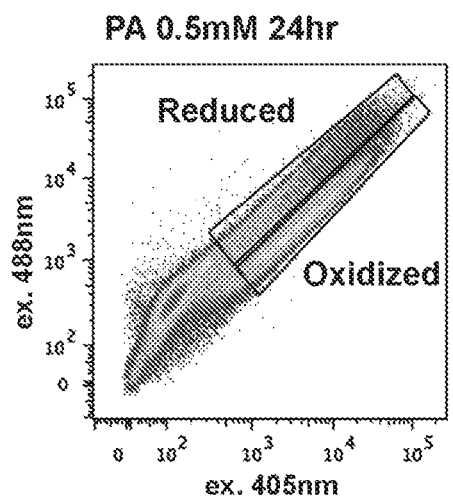
FIG. 34 is a histogram of the FACS data from INS-1 832/13 cells treated with 0.5 mM of palmitate for 24 hours.
Figure 35:
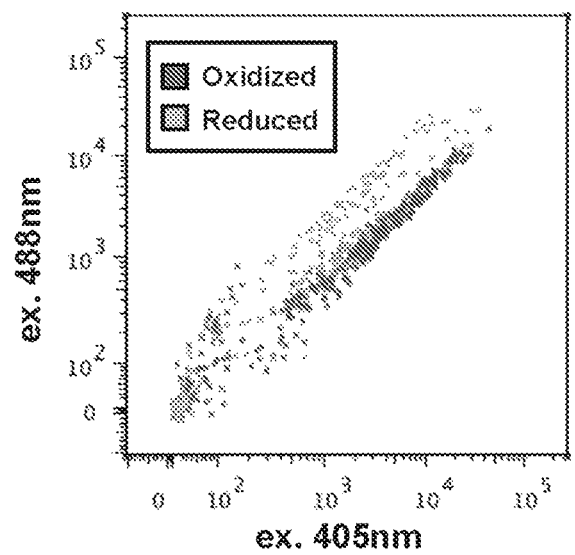
FIG. 35 is histogram showing the purity of FACS-separated oxidized and reduced INS-1 832/13 cells.

Additional experiments were performed to confirm these data. In these experiments, cells with oxidized ER and highly reduced ER were sorted by FACS following treatment with palmitate (FIGS. 34 and 35), and the expression of the UPR markers BiP and spliced XBP-1 were measured using real-time PCR. In these experiments, the reduced and oxidized cells were sorted by FACS and total RNA was extracted by RNeasy kit (Qiagen). Reverse-transcriptase and quantitative PCR was performed using BioRad iQ5 using SYBR green dye.

Figures 36, 37:
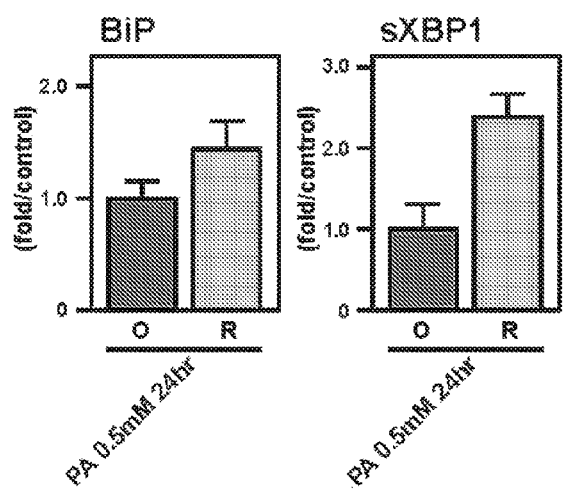
FIG. 36 is two graphs showing the expression levels of BiP (left graph) and spliced XBP1 (sXBP) (right graph) in INS-1 832/13 cells treated with 0.5 mM palmitate for 24 hours. The expression levels of BiP and sXBP were measured using real-time PCR. The error bars indicate ±standard deviation.
FIG. 37 is a table showing the expression levels of Derlin3, BiP, Hem, and PDla5 in endoplasmic reticulum purified from oxidized or reduced INS-1 832/13 cells. The expression data was gathered using DNA microarray analysis.

The data show that expression levels of BiP and spliced XBP-1 were increased in the cells with highly reduced ER as compared to the levels in the cells with an oxidized ER (FIG. 36). These data were further confirmed by expression profiling in cells with reduced ER and oxidized ER (FIG. 37). These experiments were performed using FACS-sorted INS-1 832/13 cells treated with 0.5 mM palmitate for 24 hours. The total RNA was extracted with an RNAeasy kit (Qiagen). The purified RNA was then applied to GeneChip Rat Gene 1.0 ST Array (Affymetrix) according to the manufacturer's protocol. These data indicate that cells harboring highly reduced ER also have highly activated UPR, possibly as a regulatory mechanism.

Example 5

Figure 38:
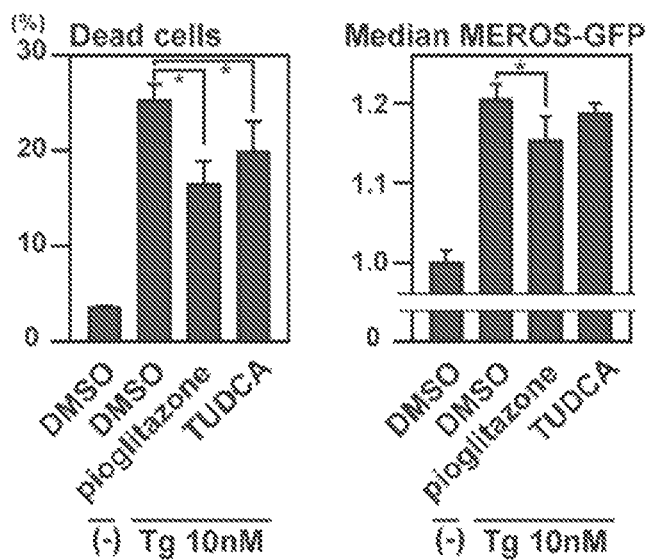
FIG. 38 is two graphs showing the percentage of dead cells (left graph) or the median MEROS-GFP ratio (right graph) of INS-1 832/13 cells treated with DMSO alone, 10 nM thapsigargin (Tg), 10 nM Tg and 10 μM pioglitazone, or 10 nM Tg and 500 mg/mL tauroursodeoxycholic acid (TUDCA).

A Small Molecule Screen for Compounds that Shift ER from a Reducing to an Oxidizing Environment The data described above indicate that chemical compounds and biologics that shift the ER towards an oxidizing environment might be effective for the treatment of diseases related to ER stress and ER dysfunction. To investigate this possibility, two FDA-approved drugs, pioglitazone (Actos) and tauroursodeoxycholic acid (TUDCA), could affect the ER redox state and ameliorate cell death in cellular models of ER diseases. Pioglitazone is approved for treating patients with type 2 diabetes and has been shown to preserve pancreatic β-cell function in a mouse model of Wolfram syndrome. Pioglitazone was shown to shift the ER to an oxidizing environment in pancreatic β-cells treated with thapsigargin (FIG. 38, right panel) and protect these cells from cell death (FIG. 38, left panel). Another small molecule, TUDCA, has been used for treatment of gallstones and biliary cirrhosis and shown to mitigate ER stress in mouse models of diabetes. TUDCA was shown to also shift the ER towards an oxidizing environment (FIG. 38, right panel) and to protect cells from death under ER stress conditions (FIG. 38, left panel).

Figure 39:
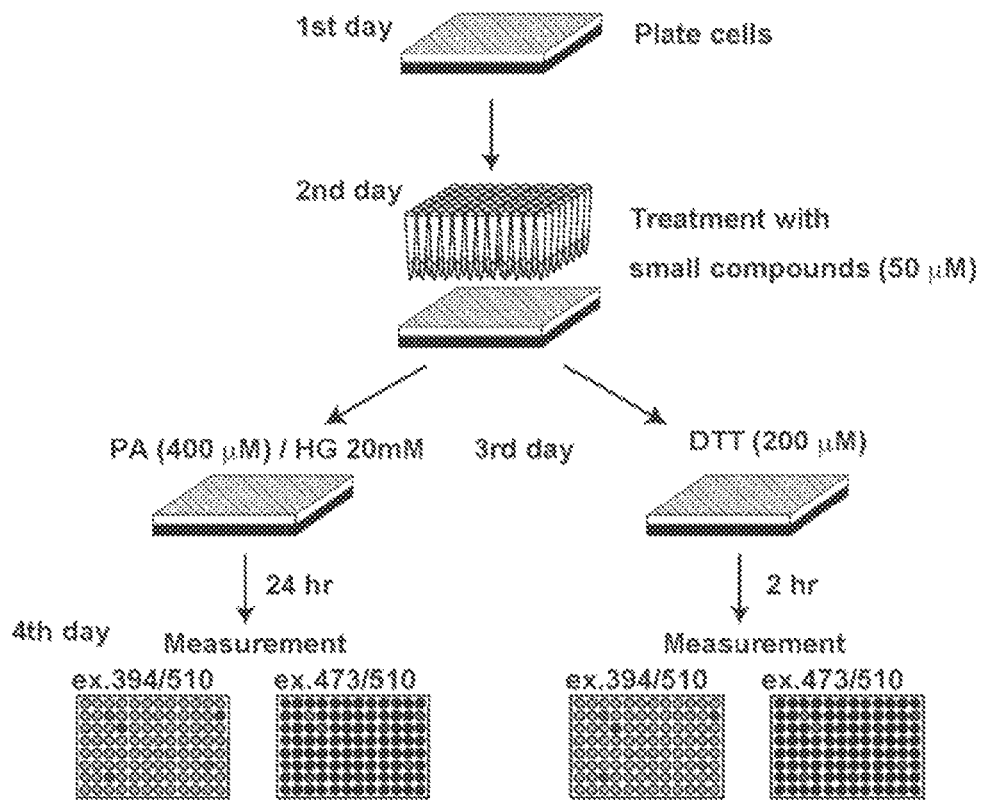
FIG. 39 is a diagram showing the screening system that uses the MEROS-GFP system.

The finding that agents shifting the ER towards an oxidizing environment can confer protection against ER stress allows for the development of a new screening assay to identify novel small molecule suppressors of reduced ER using a high-throughput approach. A pilot screen of a 1280-compound library (MicroSource), a collection of 1,040 U.S. drugs and 240 international drugs (FIG. 39) was performed. In this experiment, INS-1 832/13 cells stably-expressing MEROS-GFP were seeded (20,000 cells/well) in black optical 96-well plates. After 24 hours, 2 μL of each compound was added using the TeMo liquid handling robot. After another 24 hours, cells were challenged with 0.2 mM DTT, a strong reducing agent, for 2 hours, and then the MEROS-GFP ratio was calculated. The average ratio of untreated cells was 0.037 (S.D.=0.003) and that of DTT-treated cells was 0.069 (S.D.=0.006). Positive compounds were those that could maintain the MEROS-GFP ratio lower than 0.05. Using this criterion, 20 positive compounds were identified in the screen.

A second screen was performed using 0.4 mM palmitate in combination with 20 mM glucose to induce ER stress. Between both screens, 9 common positive compounds were identified, of which 5 were eliminated due to autofluorescence. To further eliminate false positives, INS-1 832/13 cells stably-expressing MEROS-GFP were pretreated with the remaining 4 common compounds, challenged with 0.5 mM palmitate for 24 hours, and the MEROS-GFP ratio measured using FACS. This additional step removed two compounds as false positives. The remaining two compounds were the clinically used agents apomorphine and griseofulvin. Although positively identified in the screening assays, griseofulvin had strong toxic effects on INS-1 832/13 cells.

Example 6

Figure 40:
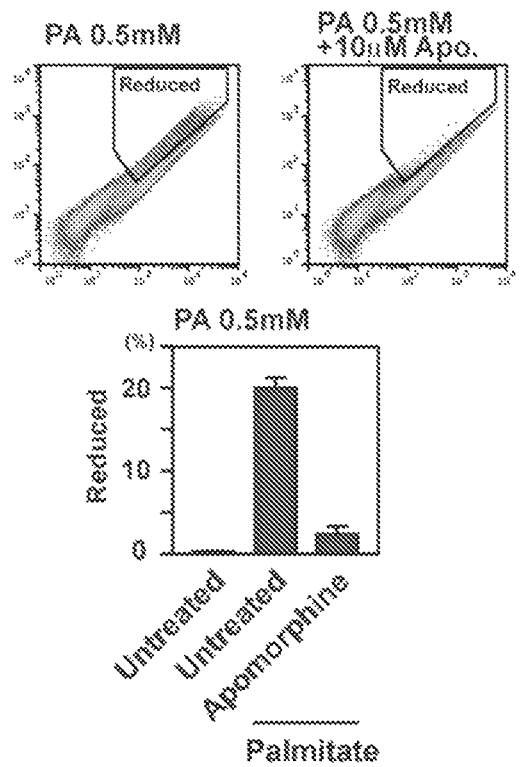
FIG. 40 are two histograms showing the FACS data gathered from INS-1 832/13-MEROS-GFP cells following treatment with 0.5 mM palmitate in the absence (top left graph) or presence (top right graph) of 10 μM apomorphine (Apo), and a graph showing the percentage of reduced cells in INS-1 832/13 MEROS-GFP cells following no treatment, or treatment with 0.5 mM palmitate in the absence or presence of 10 μM apomorphine. The error bars indicate ±standard deviation.
Figure 41:
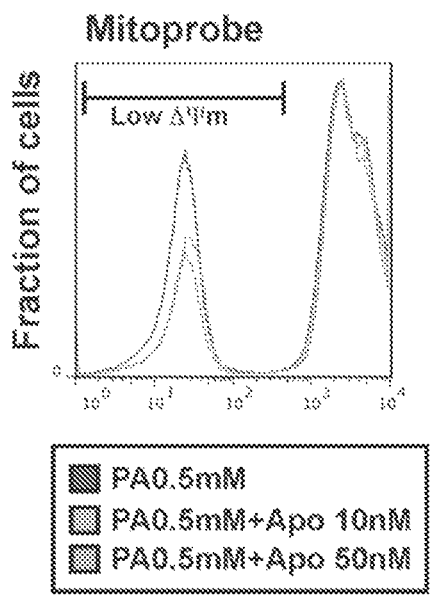
FIG. 41 is a histogram of FACS data gathered from INS-1 832/13-MEROS-GFP cells stained with Mitoprobe dye after treatment with 0.5 mM palmitate (PA) in combination with or without 10 nM or 50 nM apomorphine (Apo).
Figure 42:
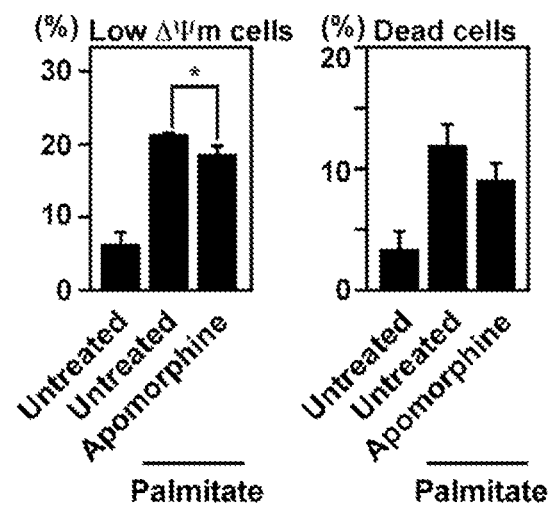
FIG. 42 is two graphs showing the percentage of low Δψm cells (left graph) and percentage of dead cells (right graph) fractionated by FACS analysis following no treatment or treatment with 0.5 mM palmitate alone or 0.5 mM palmitate and 10 nM apomorphine.
Figure 43:
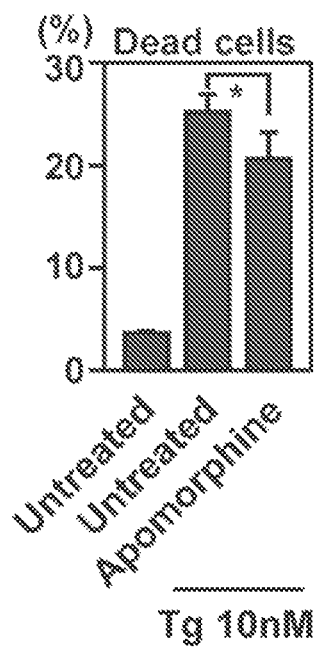
FIG. 43 is a graph of the percentage of dead cells following no treatment or treatment with 10 nM thapsigargin (Tg) or treatment with 10 nM Tg and 10 nM apomorphine.

Apomorphine Shifts the ER Toward an Oxidizing Environment and Confers Protection Against ER Stress Additional experiments were performed to confirm that apomorphine could shift the ER from a reducing to an oxidizing environment. In these experiments, INS-1 832/13 cells expressing MEROS-GFP were treated with apomorphine for 24 hours, and then challenged with palmitate for 24 hours. The data show that apomorphine treatment decreased the population of cells that had reduced ER (FIG. 40). Cell viability and mitochondrial membrane potential in INS-1 832/13 cells treated with palmitate was measured using propidium iodide (PI) and MitoProbe (Invitrogen) staining, respectively. Apomorphine decreased the population with lower mitochondrial membrane potential (FIG. 41) and suppressed ER stress-induced cell death (FIG. 42). Apomorphine also protected INS-1 832/13 cells from ER stress-mediated cell death induced by a strong ER stress inducer, thapsigargin (FIG. 43). Collectively, these data show that apomorphine shifts the ER toward an oxidizing environment and confers protection against ER stress.

Example 7

Figure 44:
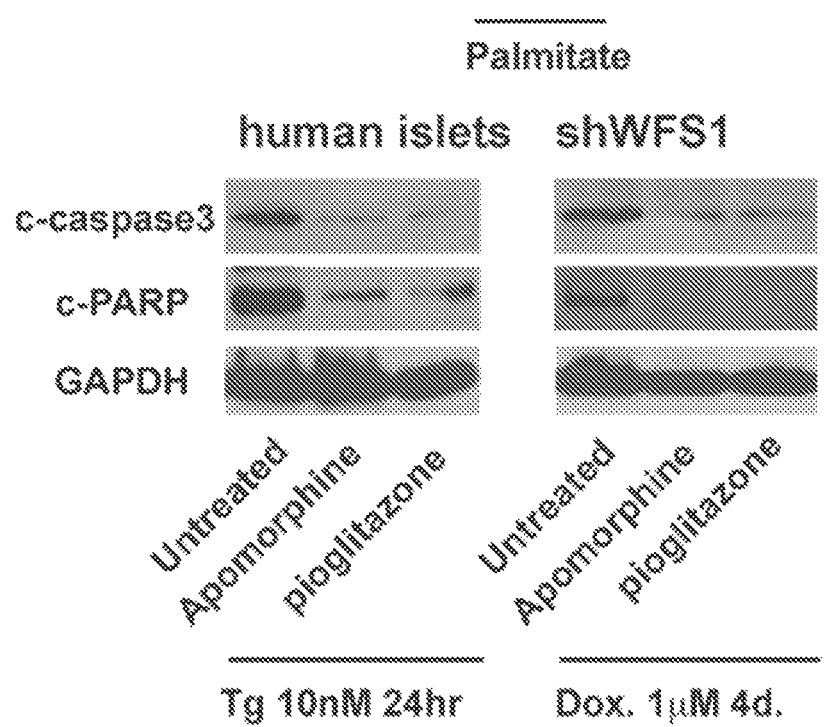
FIG. 44 are two immunoblots showing the amount of cleaved caspase 3 (c-caspase3) and cleaved PARP (c-PARP) present in 10 nM thapsigargin-treated primary human islets (right immunoblot) and 2 μM doxycycline-treated WFS1 knockdown INS-1 832/13 cells (shWFS1) (left immunoblot) treated with 10 nM apomorphine or 10 μM pioglitazone.

Small Molecules Shifting the ER Towards an Oxidizing Environment can Alleviate the Pathology of Cellular Models of ER Stress The data above show that apomorphine and pioglitazone have the ability to shift the ER towards an oxidizing environment and conferred protection against ER stress. Additional experiments were performed to determine whether apomorphine and pioglitazone can protect human islets from ER stress-mediated cell death. The data show that both apomorphine and pioglitazone could protect human islets from thapsigargin-mediated cell death (FIG. 44, left panel).

Additional experiments were performed using INS-1 832/13-derived doxycycline-inducible WFS1 knockdown cells, a cellular model of Wolfram syndrome. This model was used to test whether apomorphine and pioglitazone could prevent cell death. As previously reported, shRNA-mediated WFS1 knockdown resulted in cell death, accompanied by cleavage of caspase-3 (Riggs et al., *Diabetologia* 48:2313-2321, 2005). In this model, both apomorphine and pioglitazone suppressed cleavage of caspase 3 and cleavage of a caspase 3 substrate, poly(ADP)-ribosylating enzyme (PARP), and could protect WFS1-knockdown β-cells from cell death (FIG. 44, right panel). Taken together, these data show that small molecules that shift the ER towards an oxidizing environment can alleviate pathology of cellular models of ER diseases.

Example 8

Figure 45:
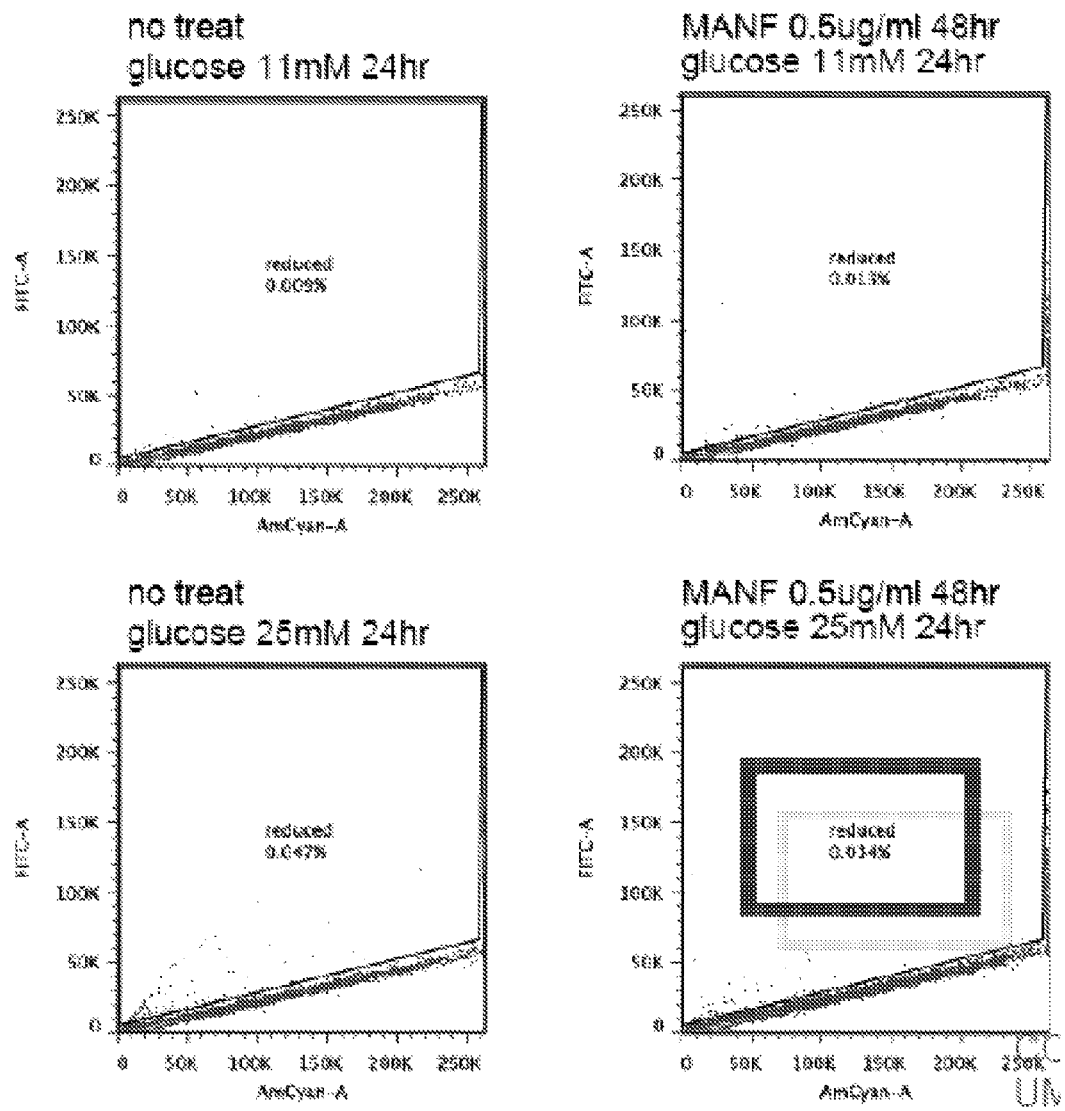
FIG. 45 is a graph of fluorescence-assisted cell sorting data showing the percentage of INS1 832/13 cells (pancreatic β cell line) containing the reduced form of EroGFP in the endoplasmic reticulum following culture in 11 mM glucose or 25 mM glucose (24 hours) (top panels and bottom panels, respectively), and treatment with 0 or 0.5 mg/mL soluble MANF for 48 hours (left panels and right panels, respectively). The cells were excited using a wavelength at 473 nm and an emission spectrum of 510 nm.

Soluble MANF Protects Pancreatic β-Cells from ER Stress and ER Stress-Induced Apoptotic Cell Death Further experiments were performed to determine whether soluble MANF can prevent fluctuations in the redox environment in the endoplasmic reticulum of pancreatic β-cells upon exposure to an agent that induces endoplasmic reticulum stress. Experiments were performed using INS-1 832/13 cells (a pancreatic β-cell line) transfected with a lentivirus vector expressing MEROS-GFP. The cells were cultured in 11 mM or 25 mM glucose, and either left untreated or treated with 0.5 µg/mL soluble MANF. The cells were then analyzed using FACS analysis using an excitation spectrum between 460-495 nm and an emission spectrum of between 520-570 nm (FITC-A optical filter) which allows for the specific detection of fluorescent emission from reduced EroGFP in the transfected cells. The data show that treatment with soluble MANF results in a decrease in the number of cells containing a detectable level of reduced MEROS-GFP (FIG. 45; lower right panel vs. lower left panel). Consistent with the data above, these data show that treatment of pancreatic β-cells with soluble MANF can shift the ER towards an oxidizing environment and may be used to treat or prevent the development of a pancreatic β cell disorder in a subject.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

The invention claimed is:

1. A method of treating or delaying an onset of a pancreatic β-cell disorder in a subject in need thereof, comprising administering to the subject an effective amount of a soluble mesencephalic astrocyte-derived neurotrophic factor (MANF) that is at least 80% identical to SEQ ID NO: 2.

2. The method of claim 1, wherein the subject is a human.

3. The method of claim 1, wherein the soluble MANF is at least 90% identical to SEQ ID NO: 2.

4. The method of claim 1, wherein the soluble MANF is at least 95% identical to SEQ ID NO: 2.

5. The method of claim 1, wherein the soluble MANF is SEQ ID NO: 2.

6. The method of claim 1, wherein the pancreatic β-cell disorder is type 1 diabetes.

7. The method of claim 1, wherein the pancreatic β-cell disorder is type 2 diabetes.

8. The method of claim 1, wherein the MANF is administered orally, intravenously, intraarterially, subcutaneously, intramuscularly, intracranially, or via injection into the cerebrospinal fluid.

9. The method of claim 1, wherein the MANF is administered intravenously.

10. The method of claim 1, wherein the MANF is administered intraarterially.

11. The method of claim 1, wherein the MANF is formulated in a physiologically acceptable liquid carrier.

12. The method of claim 11, wherein the physiologically acceptable liquid carrier is saline.

13. The method of claim 1, further comprising administering an effective amount of apomorphine to the subject.

14. The method of claim 13, wherein the subject is administered a pharmaceutical composition comprising MANF and apomorphine.

15. The method of claim 13, wherein the subject is administered a pharmaceutical composition comprising MANF and a pharmaceutical composition comprising apomorphine.

16. The method of claim 1, wherein the subject has an increased risk of developing a pancreatic β-cell disorder.

17. The method of claim 1, wherein the subject has a pancreatic β-cell disorder.

* * * * *

SEQUENCE LISTING

```
<160> NUMBER OF SEQ ID NOS: 15

<210> SEQ ID NO 1
<211> LENGTH: 182
<212> TYPE: PRT
<213> ORGANISM: Homo sapiens

<400> SEQUENCE: 1

Met Arg Arg Met Trp Ala Thr Gln Gly Leu Ala Val Ala Leu Ala Leu
 1               5                  10                  15

Ser Val Leu Pro Gly Ser Arg Ala Leu Arg Pro Gly Asp Cys Glu Val
            20                  25                  30

Cys Ile Ser Tyr Leu Gly Arg Phe Tyr Gln Asp Leu Lys Asp Arg Asp
        35                  40                  45

Val Thr Phe Ser Pro Ala Thr Ile Glu Asn Glu Leu Ile Lys Phe Cys
    50                  55                  60

Arg Glu Ala Arg Gly Lys Glu Asn Arg Leu Cys Tyr Tyr Ile Gly Ala
65                  70                  75                  80

Thr Asp Asp Ala Ala Thr Lys Ile Ile Asn Glu Val Ser Lys Pro Leu
                85                  90                  95

Ala His His Ile Pro Val Glu Lys Ile Cys Glu Lys Leu Lys Lys Lys
            100                 105                 110

Asp Ser Gln Ile Cys Glu Leu Lys Tyr Asp Lys Gln Ile Asp Leu Ser
        115                 120                 125

Thr Val Asp Leu Lys Lys Leu Arg Val Lys Glu Leu Lys Lys Ile Leu
    130                 135                 140

Asp Asp Trp Gly Glu Thr Cys Lys Gly Cys Ala Glu Lys Ser Asp Tyr
145                 150                 155                 160

Ile Arg Lys Ile Asn Glu Leu Met Pro Lys Tyr Ala Pro Lys Ala Ala
                165                 170                 175

Ser Ala Arg Thr Asp Leu
            180

<210> SEQ ID NO 2
<211> LENGTH: 158
<212> TYPE: PRT
<213> ORGANISM: Homo sapiens

<400> SEQUENCE: 2
```

Leu Arg Pro Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Thr Ile
            20                  25                  30

Glu Asn Glu Leu Ile Lys Phe Cys Arg Glu Ala Arg Gly Lys Glu Asn
        35                  40                  45

Arg Leu Cys Tyr Tyr Ile Gly Ala Thr Asp Asp Ala Ala Thr Lys Ile
    50                  55                  60

Ile Asn Glu Val Ser Lys Pro Leu Ala His His Ile Pro Val Glu Lys
65                  70                  75                  80

Ile Cys Glu Lys Leu Lys Lys Lys Asp Ser Gln Ile Cys Glu Leu Lys
                85                  90                  95

Tyr Asp Lys Gln Ile Asp Leu Ser Thr Val Asp Leu Lys Lys Leu Arg
            100                 105                 110

Val Lys Glu Leu Lys Lys Ile Leu Asp Asp Trp Gly Glu Thr Cys Lys
        115                 120                 125

Gly Cys Ala Glu Lys Ser Asp Tyr Ile Arg Lys Ile Asn Glu Leu Met
    130                 135                 140

Pro Lys Tyr Ala Pro Lys Ala Ala Ser Ala Arg Thr Asp Leu
145                 150                 155

<210> SEQ ID NO 3
<211> LENGTH: 969
<212> TYPE: DNA
<213> ORGANISM: Homo sapiens

<400> SEQUENCE: 3
ggaggcggtg cggcgcggcg ggtgcggttc agtcggtcgg cggcggcagc ggaggaggag     60
gaggaggagg aggaggagga ggatgaggag gatgtgggcc acgcagggc tggcggtggc    120 gctggctctg agcgtgctgc cgggcagccg ggcgctgcgg ccgggcgact gcgaagtttg    180
tatttcttat ctgggaagat tttaccagga cctcaaagac agagatgtca cattctcacc    240
agccactatt gaaaacgaac ttataaagtt ctgccgggaa gcaagaggca agagaatcg    300 gttgtgctac tatatcgggg ccacagatga tgcagccacc aaaatcatca atgaggtatc    360
aaagcctctg gcccaccaca tccctgtgga aagatctgt gagaagctta agaagaagga    420
cagccagata tgtgagctta gtatgacaa gcagatcgac ctgagcacag tggacctgaa    480
gaagctccga gttaaagagc tgaagaagat tctggatgac tgggggggaga catgcaaagg    540 ctgtgcagaa aagtctgact acatccggaa gataaatgaa ctgatgccta aatatgcccc    600
caaggcagcc agtgcacgga ccgatttgta gtctgctcaa tctctgttgc acctgagggg    660
gaaaaaacag ttcaactgct tactcccaaa acagcctttt tgtaatttat tttttaagtg    720
ggctcctgac aatactgtat cagatgtgaa gcctggagct ttcctgatga tgctggccct    780
acagtacccc catgagggga ttccttcct tctgttgctg gtgtactcta ggacttcaaa    840
gtgtgtctgg gatttttta ttaaagaaaa aaaatttcta gctgtccttg cagaattata    900
gtgaatacca aatggggtt ttgccccagg aggctcctaa aaaaaaaaa aaaaaaaaa    960 aaaaaaaaa                                                            969

<210> SEQ ID NO 4
<211> LENGTH: 158
<212> TYPE: PRT
<213> ORGANISM: Bos taurus

<400> SEQUENCE: 4

-continued

Leu Arg Gln Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Ser Ile
            20                  25                  30

Glu Lys Glu Leu Ile Lys Phe Cys Arg Glu Ala Arg Gly Lys Glu Asn
        35                  40                  45

Arg Leu Cys Tyr Tyr Ile Gly Ala Thr Glu Asp Ala Ala Thr Lys Ile
    50                  55                  60

Ile Asn Glu Val Ser Lys Pro Leu Ser His His Ile Pro Val Glu Lys
65              70                  75                  80

Ile Cys Glu Lys Leu Lys Lys Lys Asp Ser Gln Ile Cys Glu Leu Lys
                85                  90                  95

Tyr Asp Lys Gln Ile Asp Leu Ser Thr Val Asp Leu Lys Lys Leu Arg
            100                 105                 110

Val Lys Glu Leu Lys Lys Ile Leu Asp Asp Trp Gly Glu Thr Cys Lys
            115                 120                 125

Gly Cys Ala Glu Lys Ser Asp Tyr Ile Arg Lys Ile Asn Glu Leu Met
            130                 135                 140

Pro Lys Tyr Ala Pro Lys Ala Ala Ser Ser Arg Thr Asp Leu
145             150                 155

<210> SEQ ID NO 5
<211> LENGTH: 101
<212> TYPE: PRT
<213> ORGANISM: Rattus norvegicus

<400> SEQUENCE: 5

Leu Arg Pro Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Thr Ile
            20                  25                  30

Glu Glu Glu Leu Ile Lys Phe Cys Arg Glu Ala Arg Gly Lys Glu Asn
        35                  40                  45

Arg Leu Cys Tyr Tyr Ile Gly Ala Thr Asp Asp Ala Ala Thr Lys Ile
    50                  55                  60

Ile Asn Glu Val Ser Lys Pro Leu Ala His His Ile Pro Val Glu Lys
65              70                  75                  80

Ile Cys Glu Lys Leu Lys Lys Lys Asp Ser Gln Ile Cys Glu Leu Lys
                85                  90                  95

Tyr Gly Glu Cys Asp
            100

<210> SEQ ID NO 6
<211> LENGTH: 158
<212> TYPE: PRT
<213> ORGANISM: Mus musculus

<400> SEQUENCE: 6

Leu Arg Pro Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Thr Ile
            20                  25                  30

Glu Glu Glu Leu Ile Lys Phe Cys Arg Glu Ala Arg Gly Lys Glu Asn
        35                  40                  45

Arg Leu Cys Tyr Tyr Ile Gly Ala Thr Asp Asp Ala Ala Thr Lys Ile
    50                  55                  60

```
Ile Asn Glu Val Ser Lys Pro Leu Ala His His Ile Pro Val Glu Lys
 65                  70                  75                  80

Ile Cys Glu Lys Leu Lys Lys Asp Ser Gln Ile Cys Glu Leu Lys
                 85                  90                  95

Tyr Asp Lys Gln Ile Asp Leu Ser Thr Val Asp Leu Lys Leu Arg
            100                 105                 110

Val Lys Glu Leu Lys Lys Ile Leu Asp Asp Trp Gly Glu Met Cys Lys
        115                 120                 125

Gly Cys Ala Glu Lys Ser Asp Tyr Ile Arg Lys Ile Asn Glu Leu Met
    130                 135                 140

Pro Lys Tyr Ala Pro Lys Ala Ala Ser Ala Arg Thr Asp Leu
145                 150                 155

<210> SEQ ID NO 7
<211> LENGTH: 157
<212> TYPE: PRT
<213> ORGANISM: Sus scrofa

<400> SEQUENCE: 7

Leu Arg Pro Gly Asp Cys Glu Val Cys Ile Ser Tyr Leu Gly Arg Phe
  1               5                  10                  15

Tyr Gln Asp Leu Lys Asp Arg Asp Val Thr Phe Ser Pro Ala Ser Ile
             20                  25                  30

Glu Lys Glu Leu Thr Lys Phe Cys Arg Glu Ala Arg Gly Lys Glu Asn
         35                  40                  45

Arg Leu Cys Tyr Tyr Ile Gly Ala Thr Asp Asp Ala Ala Thr Lys Ile
 50                  55                  60

Ile Asn Glu Val Ser Lys Pro Leu Ala His His Ile Pro Val Glu Lys
 65                  70                  75                  80

Ile Cys Glu Lys Leu Lys Lys Asp Ser Gln Ile Cys Glu Leu Lys
                 85                  90                  95

Tyr Asp Lys Gln Ile Asp Leu Ser Thr Val Asp Leu Lys Leu Arg
            100                 105                 110

Val Lys Glu Leu Lys Lys Ile Leu Asp Asp Trp Gly Glu Thr Cys Lys
        115                 120                 125

Gly Cys Ala Glu Lys Ser Asp Tyr Ile Arg Lys Ile Asn Glu Leu Met
    130                 135                 140

Pro Lys Tyr Ala Pro Lys Ala Ala Ser Ser Arg Thr Asp
145                 150                 155

<210> SEQ ID NO 8
<211> LENGTH: 151
<212> TYPE: PRT
<213> ORGANISM: Drosophila melanogaster

<400> SEQUENCE: 8

Leu Lys Glu Glu Asp Cys Glu Val Cys Val Lys Thr Val Arg Arg Phe
  1               5                  10                  15

Ala Asp Ser Leu Asp Asp Ser Thr Lys Lys Asp Tyr Lys Gln Ile Glu
             20                  25                  30

Thr Ala Phe Lys Lys Phe Cys Lys Ala Gln Lys Asn Lys Glu His Arg
         35                  40                  45

Phe Cys Tyr Tyr Leu Gly Gly Leu Glu Glu Ser Ala Thr Gly Ile Leu
 50                  55                  60

Asn Glu Leu Ser Lys Pro Leu Ser Trp Ser Met Pro Ala Glu Lys Ile
 65                  70                  75                  80
```

Cys Glu Lys Leu Lys Lys Asp Ala Gln Ile Cys Asp Leu Arg Tyr
                85                  90                  95

Glu Lys Gln Ile Asp Leu Asn Ser Val Asp Leu Lys Lys Leu Lys Val
            100                 105                 110

Arg Asp Leu Lys Lys Ile Leu Asn Asp Trp Asp Glu Ser Cys Asp Gly
        115                 120                 125

Cys Leu Glu Lys Gly Asp Phe Ile Lys Arg Ile Glu Glu Leu Lys Pro
    130                 135                 140

Lys Tyr Ser Arg Ser Glu Leu
145                 150

<210> SEQ ID NO 9
<211> LENGTH: 158
<212> TYPE: PRT
<213> ORGANISM: Danio rerio

<400> SEQUENCE: 9

Leu Lys Asp Gly Glu Cys Glu Val Cys Val Gly Phe Leu Gln Arg Leu
1               5                   10                  15

Tyr Gln Thr Ile Gln Glu Asn Asn Val Lys Phe Asp Ser Asp Ser Ile
            20                  25                  30

Glu Lys Ala Leu Leu Lys Ser Cys Lys Asp Ala Lys Gly Lys Glu Asn
        35                  40                  45

Arg Phe Cys Tyr Tyr Ile Gly Ala Thr Ser Asp Ala Ala Thr Lys Ile
    50                  55                  60

Thr Asn Glu Val Ser Lys Pro Met Ser Tyr His Val Pro Val Glu Lys
65                  70                  75                  80

Ile Cys Glu Lys Leu Lys Lys Asp Ser Gln Ile Cys Glu Leu Lys
                85                  90                  95

Tyr Asp Lys Gln Val Asp Leu Ser Ser Val Asp Leu Lys Lys Leu Lys
            100                 105                 110

Val Lys Asp Leu Lys Lys Ile Leu Glu Glu Trp Gly Glu Ser Cys Lys
        115                 120                 125

Gly Cys Val Glu Lys Ser Asp Phe Ile Arg Lys Ile Asn Glu Leu Met
    130                 135                 140

Pro Lys Tyr Ala Pro Ser Ala Ala Lys Ala Arg Thr Asp Leu
145                 150                 155

<210> SEQ ID NO 10
<211> LENGTH: 236
<212> TYPE: PRT
<213> ORGANISM: Artificial Sequence
<220> FEATURE:
<223> OTHER INFORMATION: Redox-Sensitive Green Fluorescent Protein
<220> FEATURE:
<221> NAME/KEY: VARIANT
<222> LOCATION: 65
<223> OTHER INFORMATION: Xaa can be any naturally occurring amino acid

<400> SEQUENCE: 10

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Val
        35                  40                  45

Thr Thr Gly Lys Leu Pro Val Pro Trp Pro Thr Leu Val Thr Thr Phe
    50                  55                  60

```
Xaa Leu Gln Cys Phe Ala Arg Tyr Pro Asp His Met Lys Arg His Asp
 65                  70                  75                  80

Phe Phe Lys Ser Ala Met Pro Glu Gly Tyr Val Gln Glu Arg Thr Ile
                 85                  90                  95

Phe Phe Lys Asp Asp Gly Asn Tyr Lys Thr Arg Ala Glu Val Lys Phe
            100                 105                 110

Glu Gly Asp Thr Leu Val Asn Arg Ile Glu Leu Lys Gly Ile Asp Phe
        115                 120                 125

Lys Glu Asp Gly Asn Ile Leu Gly His Lys Leu Glu Tyr Asn Tyr Asn
130                 135                 140

Ser His Cys Val Tyr Ile Val Ala Asp Lys Gln Lys Asn Gly Ile Lys
145                 150                 155                 160

Val Asn Phe Lys Ile Arg His Asn Ile Glu Asp Gly Ser Val Gln Leu
                165                 170                 175

Ala Asp His Tyr Gln Gln Asn Thr Pro Ile Gly Asp Gly Pro Val Leu
            180                 185                 190

Leu Pro Asp Asn His Tyr Leu Cys Tyr Gln Ser Ala Leu Ser Lys Asp
        195                 200                 205

Pro Asn Glu Lys Arg Asp His Met Val Leu Leu Glu Phe Val Thr Ala
    210                 215                 220

Ala Gly Ile Thr His Gly Met Asp Glu Leu Tyr Lys
225                 230                 235
```

<210> SEQ ID NO 11

<400> SEQUENCE: 11

000

<210> SEQ ID NO 12
<211> LENGTH: 18
<212> TYPE: PRT
<213> ORGANISM: Homo sapiens

<400> SEQUENCE: 12

```
Met Lys Leu Ser Leu Val Ala Ala Met Leu Leu Leu Leu Ser Ala Ala
 1               5                  10                  15

Arg Ala
```

<210> SEQ ID NO 13
<211> LENGTH: 18
<212> TYPE: PRT
<213> ORGANISM: Mus musculus

<400> SEQUENCE: 13

```
Met Met Lys Phe Thr Val Ala Ala Ala Leu Leu Leu Leu Gly Ala Val
 1               5                  10                  15

Arg Ala
```

<210> SEQ ID NO 14
<211> LENGTH: 285
<212> TYPE: PRT
<213> ORGANISM: Artificial Sequence
<220> FEATURE:
<223> OTHER INFORMATION: MEROS-Green Fluorescent Protein

<400> SEQUENCE: 14

```
Met Met Lys Phe Thr Val Val Ala Ala Ala Leu Leu Leu Leu Gly Ala
 1               5                  10                  15
```

```
Val Arg Ala Glu Glu Asp Pro Val Ala Thr Met Ser Lys Gly
         20                  25                  30

Glu Glu Leu Phe Thr Gly Val Val Pro Ile Leu Val Glu Leu Asp Gly
         35                  40                  45

Asp Val Asn Gly His Lys Phe Ser Val Ser Gly Glu Gly Glu Gly Asp
 50                  55                  60

Ala Thr Tyr Gly Lys Leu Thr Leu Lys Phe Ile Ser Thr Thr Gly Lys
 65                  70                  75                  80

Leu Pro Val Pro Trp Pro Thr Leu Val Thr Thr Phe Ser Tyr Gly Val
                 85                  90                  95

Gln Cys Phe Ser Arg Tyr Pro Asp His Met Lys Arg His Asp Phe Phe
             100                 105                 110

Lys Ser Ala Met Pro Glu Gly Tyr Val Gln Glu Arg Thr Ile Phe Phe
         115                 120                 125

Lys Asp Asp Gly Asn Tyr Lys Thr Arg Ala Glu Val Lys Phe Glu Gly
 130                 135                 140

Asp Thr Leu Val Asn Arg Ile Glu Leu Lys Gly Ile Asp Phe Lys Glu
145                 150                 155                 160

Asp Gly Asn Ile Leu Gly His Lys Leu Glu Tyr Asn Tyr Asn Cys His
                165                 170                 175

Lys Val Tyr Ile Met Ala Asp Lys Gln Lys Asn Gly Ile Lys Val Asn
            180                 185                 190

Phe Lys Ile Arg His Asn Ile Glu Asp Gly Ser Val Gln Leu Ala Asp
        195                 200                 205

His Tyr Gln Gln Asn Thr Pro Ile Gly Asp Gly Pro Val Leu Leu Pro
    210                 215                 220

Asp Asn His Tyr Leu Lys Thr Cys Ser Ala Leu Ser Lys Asp Pro Asn
225                 230                 235                 240

Glu Lys Arg Asp His Met Val Leu Leu Glu Arg Val Thr Ala Ala Gly
                245                 250                 255

Ile Thr His Gly Met Asp Glu Leu Tyr Lys Thr Ser Gly Gly Pro Pro
            260                 265                 270

Pro Thr Gly Glu Glu Asp Thr Ser Glu Lys Asp Glu Leu
        275                 280                 285

<210> SEQ ID NO 15
<211> LENGTH: 858
<212> TYPE: DNA
<213> ORGANISM: Artificial Sequence
<220> FEATURE:
<223> OTHER INFORMATION: MEROS-Green Fluorescent Protein

<400> SEQUENCE: 15
atgatgaagt tcactgtggt ggcggcggcg ttgctgctgc tgggcgcggt gcgggccgag      60
gaggaggatc caccggtcgc caccatgagt aaaggagaag aacttttcac tggagttgtc     120
ccaattcttg ttgaattaga tggtgatgtt aatgggcaca attttctgt cagtggagag      180 ggtgaaggtg atgcaacata cggaaaactt acccttaaat ttatttccac tactggaaaa    240
ctacctgttc catggccaac acttgtcact actttcagtt atggtgttca atgcttttca    300
agatacccag atcatatgaa acggcatgac tttttcaaga gtgccatgcc cgaaggttat    360
gtacaggaaa gaactatatt tttcaaagat gacgggaact acaagacacg tgctgaagtc    420
aagtttgaag gtgatacccct tgttaataga atcgagttaa aaggtattga ttttaaagaa    480
gatggaaaca ttcttggaca caaattggaa tacaactata actgccacaa ggtatacatc    540
```

```
atggcagaca aacaaaagaa tggaatcaaa gttaacttca aaattagaca caacattgaa      600
gatggaagcg ttcaactagc agaccattat caacaaaata ctccaattgg cgatggccct     660
gtccttttac cagacaacca ttacctgaag acatgctctg ccctttcgaa agatcccaac     720
gaaaagagag accacatggt ccttcttgag cgcgtaacag ctgctgggat tacacatggc    780
atggatgaac tatacaaaac tagtggaggc cctcccccaa ctggtgaaga ggatacatca    840
gaaaaagatg agttgtag                                                    858
```